(12) United States Patent
Cohen

(10) Patent No.: US 9,949,004 B2
(45) Date of Patent: Apr. 17, 2018

(54) SOUND AND VIBRATION TRANSMISSION DEVICE

(71) Applicant: Daniel E. Cohen, Eden Prairie, MN (US)

(72) Inventor: Daniel E. Cohen, Eden Prairie, MN (US)

( * ) Notice: Subject to any disclaimer, the term of this patent is extended or adjusted under 35 U.S.C. 154(b) by 0 days.

(21) Appl. No.: 13/936,154

(22) Filed: Jul. 6, 2013

(65) Prior Publication Data

US 2014/0010387 A1  Jan. 9, 2014

Related U.S. Application Data

(63) Continuation-in-part of application No. PCT/US2012/020503, filed on Jan. 6, 2012, which is
(Continued)

(51) Int. Cl.
*H04R 1/02* (2006.01)
*A61H 23/02* (2006.01)
(Continued)

(52) U.S. Cl.
CPC ......... *H04R 1/025* (2013.01); *A61H 23/0236* (2013.01); *H04R 1/028* (2013.01); *H04R 5/023* (2013.01); *H04R 5/04* (2013.01); *A61H 2201/0138* (2013.01); *A61H 2201/0149* (2013.01); *A61H 2201/10* (2013.01);
(Continued)

(58) Field of Classification Search
CPC ........ H04R 1/025; H04R 1/028; H04R 5/023; A61H 23/0218; A61H 23/0236; A61H 39/007; B60N 2/4876

USPC ......... 381/333, 86, 301, 302, 151, 152, 386, 381/388, 389, 395; 297/217.4, 217.5; 600/27, 28; 601/46–66

See application file for complete search history.

(56) References Cited

U.S. PATENT DOCUMENTS 3,085,568 A * 4/1963 Harry .............................. 601/55
4,023,566 A * 5/1977 Martinmaas .................... 601/47
(Continued)

FOREIGN PATENT DOCUMENTS

WO 2004082325 A2  9/2004
WO 2012094607 A1  7/2012

OTHER PUBLICATIONS

International Search Report and Written Opinion of PCT/US2012/020503, dated May 11, 2012.
(Continued)

*Primary Examiner* — Joshua Kaufman
(74) *Attorney, Agent, or Firm* — Briggs and Morgan, P.A.; Audrey J. Babcock

(57) ABSTRACT

An apparatus capable of transmitting sound and vibrations to a user is described. The apparatus may also generate an electromagnetic field sufficient to stimulate the user's energy system. The apparatus includes a support structure configured to support at least a part of the user's body; a transducer coupled to the frame of the support structure in a manner which allows the transducer to move in relation to the frame; and an audio signal source for transmitting audio signals to the transducer. The transducer is capable of receiving and responding to audio signals having a wide range of audio frequencies when the apparatus is in use.

13 Claims, 9 Drawing Sheets

Related U.S. Application Data a continuation-in-part of application No. 13/079,812, filed on Apr. 4, 2011, now Pat. No. 8,668,045, which is a continuation-in-part of application No. 12/746,415, filed as application No. PCT/US2008/085776 on Dec. 6, 2008, now abandoned, said application No. 13/079,812 is a continuation-in-part of application No. 12/465,501, filed on May 13, 2009, now Pat. No. 7,918,308, which is a continuation of application No. 10/943,186, filed on Sep. 16, 2004, now Pat. No. 7,553,288, which is a continuation-in-part of application No. PCT/US2004/007354, filed on Mar. 10, 2004.

(60) Provisional application No. 61/430,378, filed on Jan. 6, 2011, provisional application No. 61/430,392, filed on Jan. 6, 2011, provisional application No. 61/534,770, filed on Sep. 14, 2011, provisional application No. 61/048,188, filed on Apr. 26, 2008, provisional application No. 61/012,050, filed on Dec. 6, 2007, provisional application No. 60/453,549, filed on Mar. 10, 2003, provisional application No. 60/493,645, filed on Aug. 7, 2003, provisional application No. 60/518,973, filed on Nov. 10, 2003.

(51) Int. Cl.
  *H04R 5/02* (2006.01)
  *H04R 5/04* (2006.01)
  *A61N 2/00* (2006.01)
  *A61N 2/06* (2006.01)

(52) U.S. Cl.
  CPC .......... *A61H 2201/1654* (2013.01); *A61H 2201/5005* (2013.01); *A61H 2203/0425* (2013.01); *A61H 2203/0443* (2013.01); *A61H 2205/062* (2013.01); *A61H 2205/086* (2013.01); *A61N 2/002* (2013.01); *A61N 2/008* (2013.01); *A61N 2/06* (2013.01)

(56) References Cited

U.S. PATENT DOCUMENTS

| | | | | |
|---|---|---|---|---|
| 4,038,499 A * | 7/1977 | Yeaple | ............ | 381/301 |
| 4,055,170 A * | 10/1977 | Nohmura | ............ | 601/47 |
| 4,064,376 A * | 12/1977 | Yamada | ............ | 381/152 |
| 4,354,067 A * | 10/1982 | Yamada | ............ | A61H 23/0236 381/301 |
| 4,507,816 A * | 4/1985 | Smith, Jr. | ............ | 5/666 |
| 4,680,492 A * | 7/1987 | Tamura | ............ | 310/15 |
| 4,778,027 A * | 10/1988 | Taylor | ............ | 181/175 |
| 5,076,260 A * | 12/1991 | Komatsu | ............ | 601/59 |
| 5,086,755 A * | 2/1992 | Schmid-Eilber | ............ | 601/47 |
| 5,086,769 A * | 2/1992 | Vianello et al. | ............ | 607/94 |
| 5,097,821 A * | 3/1992 | Eakin | ............ | 601/47 |
| 5,101,810 A * | 4/1992 | Skille et al. | ............ | 601/47 |
| 5,113,852 A * | 5/1992 | Murtonen | ............ | 601/47 |
| 5,133,017 A * | 7/1992 | Cain et al. | ............ | 381/71.6 |
| 5,143,055 A * | 9/1992 | Eakin | ............ | 601/47 |
| 5,314,403 A * | 5/1994 | Shaw | ............ | 601/148 |
| 5,368,359 A * | 11/1994 | Eakin | ............ | 297/217.4 |
| 5,387,026 A * | 2/1995 | Matsuhashi et al. | ............ | 297/217.4 |
| 5,604,816 A * | 2/1997 | Totani | ............ | 381/412 |
| 5,865,771 A * | 2/1999 | Shuto et al. | ............ | 601/47 |
| 5,887,071 A * | 3/1999 | House | ............ | 381/386 |
| 5,895,348 A * | 4/1999 | Hosaka | ............ | 600/27 |
| 6,027,463 A * | 2/2000 | Moriyasu | ............ | 601/46 |
| 6,215,885 B1 * | 4/2001 | Geiger | ............ | 381/386 |
| 6,369,312 B1 * | 4/2002 | Komatsu | ............ | 84/723 |
| 6,505,705 B1 | 1/2003 | Espiritu et al. | | |
| 6,544,165 B1 * | 4/2003 | McNew | ............ | 600/27 |
| 6,656,137 B1 * | 12/2003 | Tyldsley et al. | ............ | 601/15 |
| 6,702,767 B1 * | 3/2004 | Douglas et al. | ............ | 601/15 |
| 7,141,028 B2 * | 11/2006 | McNew | ............ | 601/15 |
| 7,553,288 B2 * | 6/2009 | Cohen | ............ | 601/47 |
| 7,846,084 B2 * | 12/2010 | McNew | ............ | 600/27 |
| 8,061,210 B2 * | 11/2011 | Crowson, II | ............ | 73/668 |
| 8,337,385 B1 * | 12/2012 | Cornell | ............ | 600/28 |
| 8,622,471 B2 * | 1/2014 | Porter et al. | ............ | 297/217.4 |
| 2002/0018576 A1 * | 2/2002 | Shima | ............ | 381/396 |
| 2003/0123679 A1 * | 7/2003 | Dudleston et al. | ............ | 381/87 |
| 2004/0021351 A1 * | 2/2004 | House | ............ | 297/217.4 |
| 2005/0038313 A1 | 2/2005 | Ardizzone | | |
| 2005/0053252 A1 * | 3/2005 | Cohen | ............ | 381/333 |
| 2006/0030907 A1 * | 2/2006 | McNew | ............ | 607/88 |
| 2006/0106313 A1 | 5/2006 | Hobson | | |
| 2010/0320819 A1 * | 12/2010 | Cohen et al. | ............ | 297/217.4 |
| 2011/0251535 A1 * | 10/2011 | Bender | ............ | 601/49 |
| 2012/0051579 A1 * | 3/2012 | Cohen | ............ | 381/388 |

OTHER PUBLICATIONS

International Search Report and Written Opinion of PCT/US2014/045425, dated Nov. 3, 2014.

Extended European Search Report of EP 14822745.7, dated Apr. 4, 2016.

\* cited by examiner

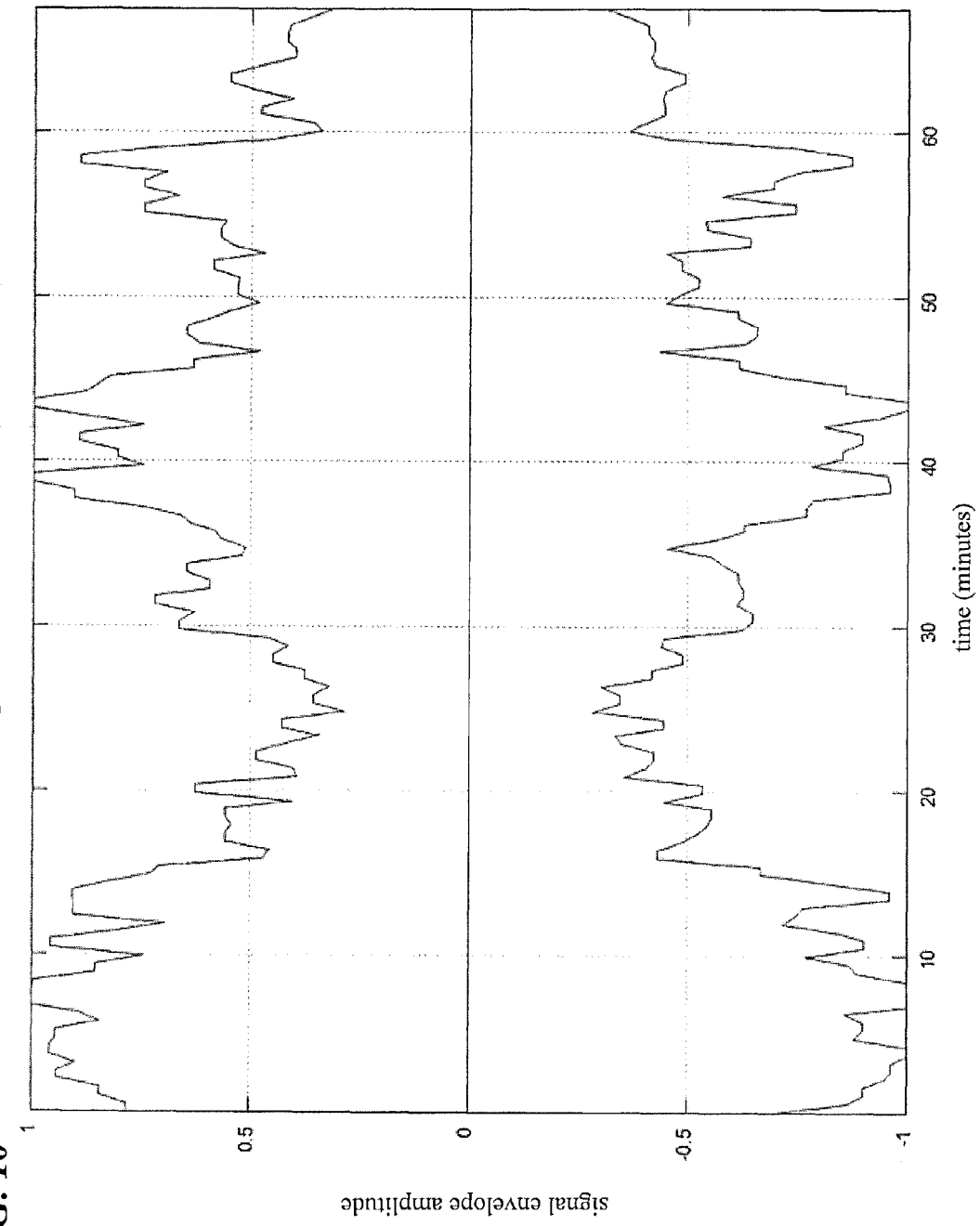

SOUND AND VIBRATION TRANSMISSION DEVICE

RELATED APPLICATIONS

This application is a continuation-in-part of International Patent Application No. PCT/US2012/020503, filed on Jan. 6, 2012, which claims the benefit of priority of U.S. Provisional Patent Application No. 61/430,378, filed on Jan. 6, 2011, U.S. Provisional Patent Application No. 61/430,392, filed on Jan. 6, 2011, and U.S. Provisional Patent Application No. 61/534,770, filed on Sep. 14, 2011, which applications are incorporated by reference herein in their entireties. International Patent Application No. PCT/US2012/020503 is a continuation-in-part of U.S. patent application Ser. No. 13/079,812, filed on Apr. 4, 2011, which is a continuation-in-part of U.S. patent application Ser. No. 12/746,415, which has a 35 U.S.C. §371(c) date of Sep. 7, 2010 and is a national stage application of PCT Application No. PCT/US2008/085,776, filed on Dec. 6, 2008, which claims the benefit of priority of U.S. Provisional Patent Application No. 61/048,188, filed on Apr. 26, 2008, and U.S. Provisional Patent Application No. 61/012,050, filed on Dec. 6, 2007, which applications are incorporated by reference herein in their entireties. U.S. patent application Ser. No. 13/079,812 is also a continuation-in-part of U.S. patent application Ser. No. 12/465,501, filed on May 13, 2009, now U.S. Pat. No. 7,918,308, which is a continuation of U.S. patent application Ser. No. 10/943,186, filed on Sep. 16, 2004, now U.S. Pat. No. 7,553,288, which is a continuation-in-part of International Application No. PCT/US2004/007,354, filed on Mar. 10, 2004, which claims the benefit of priority of U.S. Provisional Patent Application No. 60/453,549, filed on Mar. 10, 2003, U.S. Provisional Patent Application No. 60/493,645, filed on Aug. 7, 2003, and U.S. Provisional Patent Application No. 60/518,973, filed on Nov. 10, 2003, which applications are incorporated by reference herein in their entireties.

BACKGROUND OF THE INVENTION

Meditation or relaxation states counter the pathologic effects of stress on the body and the mind, and relaxation techniques and meditation have become complementary treatment modalities used in the therapy of many illnesses. Learning how to relax physically requires that a person become more aware of how his or her body feels. Most people are not well grounded in the physical (they do not derive their awareness from all aspects of themselves, including their bodies) and therefore, they do not feel their bodies very well. They generally become more aware of their physical bodies only when they experience discomfort or pain or when they have a physical illness. When they are not in distress their focus is generally external to themselves, perceiving the outer world almost exclusively with their physical senses, most notably with their eyes and ears. This is why people are generally not very body-centered and why more subtle bodily sensations tend to be ignored.

In a state of reduced bodily awareness, it is difficult to perceive the degree to which one is physically relaxed. Therefore, to become more physically relaxed, one must develop a greater appreciation of how his or her body feels. Greater intensity of stimulation causes greater neuronal recruitment along the neurologic pathways and at the neocortex of the brain, enabling greater perception. This is especially important for those areas of the body that have less dense neuronal supply, such as the back of the torso.

Just as music that is heard stimulates the auditory cortex directly, music that is felt directly by the person's body stimulates the much larger somatosensory cortex, thereby simultaneously impacting more of the brain's primary sensory cortex.

Sound therapy is a procedure which may be used to promote relaxation or meditation. Practitioners of sound therapy play pre-recorded music, instruments and/or create music and sound vocally for patients, or have the patients participate directly by playing instruments, singing, humming, toning or chanting. When patients sing, hum, tone or chant, they expose their bodies more directly to the sound waves since the body itself is generating the various frequencies or sound waves internally. Many people, however, are unwilling or unable to create sounds for themselves and must rely on sound sources external to their bodies.

Consequently, there is a need for a device and method for transmitting sound and vibrations to a user to promote relaxation, meditation, and healing.

BRIEF SUMMARY OF THE INVENTION

The present invention relates to a device and method for administering sounds and vibrations to a user's body in order to provide health benefits to the user. The sounds and vibrations are preferably administered in the presence of a magnetic field.

The present invention is directed to a device comprising an audio signal source, such as but not limited to a CD player or MP3 device, adapted to play music through one or more electromagnetic drivers that generate synchronized sound and vibration, affecting the central nervous system. The electromagnetic drivers may be, but are not limited to, transducers. The device further comprises a strategically placed dynamically fluctuating electromagnetic field affecting the human energy system, particularly the chakras at the base of the spine and under the feet. The synchronized sound and vibration and the electromagnetic field synergistically produce a very potent neuro-psychological relaxation response and an energetic effect to both counteract stress and also aid in spiritual development.

The present invention is also directed to an apparatus capable of transmitting vibrations to a user, including a support structure configured to support at least part of the user's body; a transducer coupled to the frame of the support structure such that the transducer is capable of movement in relation the frame; and an audio signal source, wherein the transducer receives audio signals having a wide range of audio frequencies from the audio signal source when the apparatus is in use. The audio signals may be transmitted from the audio signal source to the transducer without filtering out any frequencies, thereby allowing all audio frequencies transmitted from the audio signal source to pass through to the transducer. For example, when the apparatus is in use, the transducer may receive audio signals in a range of from about 20 Hz to about 20,000 Hz. The transducer may move up to about 0.1 inch in relation to the frame, in a direction parallel to a mass-loaded cone of the transducer, when the apparatus is in use. In some embodiments, the transducer may move in an amount greater than about 0.1 inch in relation the frame. For example, the transducer may move up to about 0.2 inch or more, depending on the degree of coupling of the transducer to the frame, and on the compressibility of materials used in the support structure.

The present invention is further directed to a method of transmitting vibrations to a user, including generating vibrations of sufficient magnitude to mechanically vibrate molecules, cellular structures, cells, structural components of organs, or organs of the user's body. The vibrations may be administered at a frequency to resonate a targeted organ, organ sub-structure, tissue, or cavity of the user's body. The vibrations may also induce mild vibrations throughout the user's body to facilitate movement of interstitial fluid into a vascular space.

The present invention is also directed to a method of transmitting vibrations to a user which includes both providing a magnetic field in close proximity to the user, and generating vibrations of sufficient magnitude to mechanically vibrate molecules, cellular structures, cells, structural components of organs, or organs of the user's body. If the magnetic field is a static magnetic field, the combination of the magnetic field and the vibrations may induce electromechanical forces to facilitate preferential chemical reactions within the user's body. If the magnetic field is an oscillating magnetic field, the magnetic field alone may be sufficient to generate an electromotive force to facilitate preferential chemical reactions within the user's body.

The present invention is further directed to an apparatus capable of transmitting vibrations to a user, including a support structure configured to support at least a part of the user's body; an audio signal source for generating audio signals of layered music, wherein the layered music is created by simultaneously playing a plurality of different musical selections; and a driver disposed within the support structure and adapted to receive the audio signals from the audio signal source, wherein the driver is adapted to convert said audio signals into organ specific vibrations of sufficient magnitude to resonate an organ, organ sub-structure, tissue, or cavity of the user's body. The apparatus may further include a filter capable of removing frequencies other than the resonant frequencies of the organ, organ sub-structure, tissue, or cavity of the user's body. The apparatus may also include a processor capable of regulating the vibrations such that at least some of the vibrations are at an amplitude and/or a frequency selected to facilitate the movement of interstitial fluid into a vascular space of the user's body.

The present invention is also directed to an apparatus capable of transmitting vibrations to a user, including a support structure configured to support at least a part of the user's body; an audio signal source for generating audio signals of layered music, wherein the layered music is created by simultaneously playing a plurality of different musical selections; and a driver disposed within the support structure and adapted to receive the audio signals from the audio signal source, wherein the driver is adapted to generate an electromotive force sufficient to trigger chemical reactions in the user's body. The apparatus may include both a magnet capable of generating a magnetic field and a driver capable of producing vibrations of sufficient magnitude to mechanically vibrate molecules, cellular structures, cells, structural components of organs, or organs of a user's body. The magnet capable of generating the magnetic field may also be a part of the driver. The magnetic field may be either a static magnetic field or an oscillating magnetic field. Alternatively, both a static magnetic field and an oscillating magnetic field may be present. If an oscillating magnetic field is present, it may be of sufficient strength to generate an electromotive force within the user's body. If an oscillating magnetic field is not present, or is not of sufficient strength, then a static magnetic field in combination with the vibrations produced by the driver may generate an electromotive force with the user's body.

The present invention is also directed to an apparatus capable of transmitting vibrations to a user, including a support structure configured to support at least a part of the user's body; an audio signal source for generating audio signals of layered music, wherein the layered music is created by simultaneously playing a plurality of different musical selections; and a driver disposed within the support structure and adapted to receive the audio signals from the audio signal source, wherein the driver is adapted to induce mild vibrations throughout the user's body to facilitate movement of interstitial fluid into a vascular space.

The foregoing has outlined rather broadly the features and technical advantages of the present invention in order that the detailed description of the invention that follows may be better understood. Additional features of the invention which form the subject of the claims of the invention will be described hereinafter. It should be appreciated by those skilled in the art that the specific embodiments disclosed may be readily utilized as a basis for modifying or designing other methods or structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description.

BRIEF DESCRIPTION OF THE DRAWINGS

FIG. 10 is a graph of the signal envelope of the layered music of FIG. 8 over time.

DETAILED DESCRIPTION OF THE INVENTION

Figure 1:
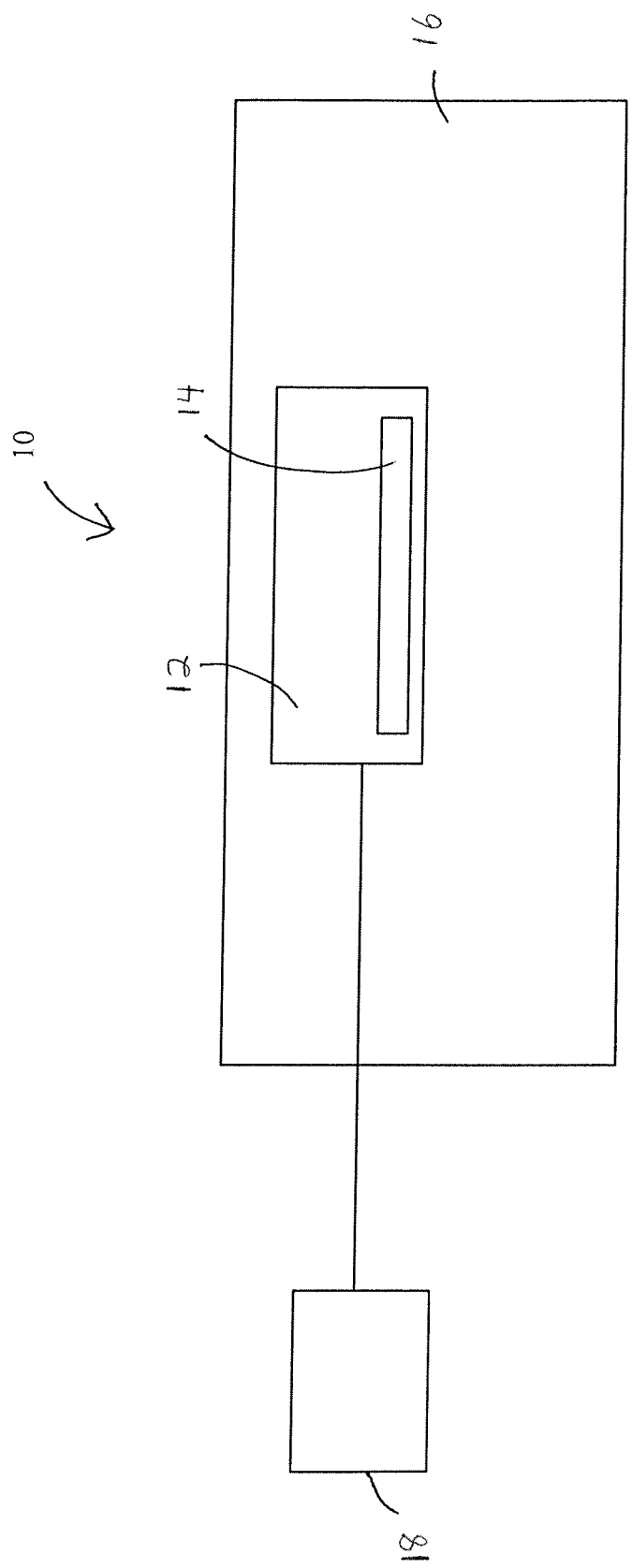
FIG. 1 is a block diagram representing one embodiment of a device in accordance with the present invention.

The present invention is directed to a method of employing sounds, vibrations, and electromagnetism, singly or in combination, to confer healing, disease prevention, and wellness. While not intending to be bound by theory, the health benefits provided by the method of the present invention are believed to result from one or more of the following five mechanisms:

1. Administering sounds and vibrations to induce profound therapeutic relaxation and meditation-like mind conditioning to normalize autonomic nervous system, neuro-endocrine, and immune system functioning and reduce the harmful effects of adrenaline and cortisol (profound therapeutic relaxation/anti-stress response);

2. Using a dynamically fluctuating electromagnetic field to stimulate a person's energy system;

3. Inducing electro-mechanical forces within and around cells to facilitate preferential chemical reactions;

4. Administering organ specific vibrations to resonate organs, organ sub-structures, tissues, and cavities; and 5. Inducing mild vibrations throughout the body to facilitate movement of interstitial fluid into the vascular space, promoting increased glomerular filtration and diuresis and improved micro-vascular blood flow.

When more than one of these five mechanisms are employed in accordance with the present invention, the employed mechanisms may work synergistically to provide health benefits to the user. Each of these five mechanisms is discussed further in the discussion provided below.

In some embodiments of the present invention, sounds, vibrations, and electromagnetism are administered using electromagnetically produced vibration and sound (hereinafter referred to as "EPVS"). For example, some electromagnetic drivers, such as speakers, containing magnets may be used to administer EPVS in accordance with the present invention. Examples of devices which may be used to administer EPVS are described in U.S. Patent Application Publication No. 2006/0036201, U.S. Pat. No. 7,553,288, and U.S. Patent Application Publication No. 2010/0320819, each of which documents is incorporated by reference herein in its entirety.

In one embodiment, the present invention is a device using one or more electromagnetic drivers containing or in close proximity to one or more magnets, wherein the magnetic field provided by one or more of the magnets is sufficiently strong to generate an electromotive force within a user's body. In this embodiment, if the magnetic field is a stationary magnetic field, then the mechanical effects of the audio drivers must generate sufficient movement in and around the cells of the user to generate an electromotive force. Alternatively, an oscillating magnetic field may be used. The device of this embodiment is capable of producing audible sounds. The device may also be capable of producing vibrations outside of the audible range. The device of this embodiment is also capable of producing specific and non-specific vibrations of sufficient magnitude to mechanically vibrate molecules, cellular structures, cells, and larger structural components of organs within the body of interest. As used herein, "specific vibrations" are vibrations at a frequency which resonates an organ, organ sub-structure, tissue, or cavity of a user's body that has been targeted for treatment. This device, when operated in close proximity to a user's body or to a tissue of interest of the user's body, may confer healing, disease prevention, and wellness to the user as a result of all five mechanisms listed above.

In some embodiments, a device in accordance with the present invention may support all or part of a user's body. The device may be a body-supporting apparatus for sitting on, reclining on or lying upon. Examples of forms which the device may take include, but are not limited to, a chair, a table, a bed, a pad, and a combination of pads.

An embodiment of the present invention comprises an audio signal source (i.e. a sound source), such as but not limited to a CD player or MP3 device, adapted to play amplified, layered music or music containing much of the audio frequency range (20 Hz to 20,000 Hz) through one or more electromagnetic drivers that generate synchronized sound and vibration, affecting the central nervous system. The electromagnetic drivers may be, but are not limited to, transducers. This embodiment of the present invention further comprises a strategically placed dynamically fluctuating electromagnetic field affecting the human energy system, particularly the chakras at the base of the spine and under the feet.

In a preferred embodiment of the present invention, the dynamically fluctuating electromagnetic field is generated by one or more transducers, which may also generate the synchronized sound and vibration. Transducers which may be used in connection with the present invention are further discussed below.

FIG. 1 is a block diagram representing one embodiment of a device 10 in accordance with the present invention. As shown in FIG. 1, a driver 12 which is capable of producing vibrations contains a magnet 14. Driver 12, which may be a speaker or transducer, is located in a support structure 16 adapted to support at least a part of the user's body. Support structure 16 may be, for example, a chair, a couch, a table, a bed, a pad, or a combination of pads. An audio signal source 18 generates audio signals received by driver 12. The audio signal source may be, for example, a VCR, DVD, CD or MP3 player, or another electronic device that has audio signal output capabilities. The audio signal source may include more than one device having audio signal output capabilities. For example, the audio signal source may include a plurality of CD players, with each CD player playing a CD of a different musical selection or title. In this manner, the audio signal source may generate audio signals of layered music, which is created by simultaneously playing a plurality of different musical selections, as discussed below. The audio signal source may also generate audio signals of layered music by, for example, accessing a storage device such as a CD or DVD on which layered music is stored.

Figure 2:
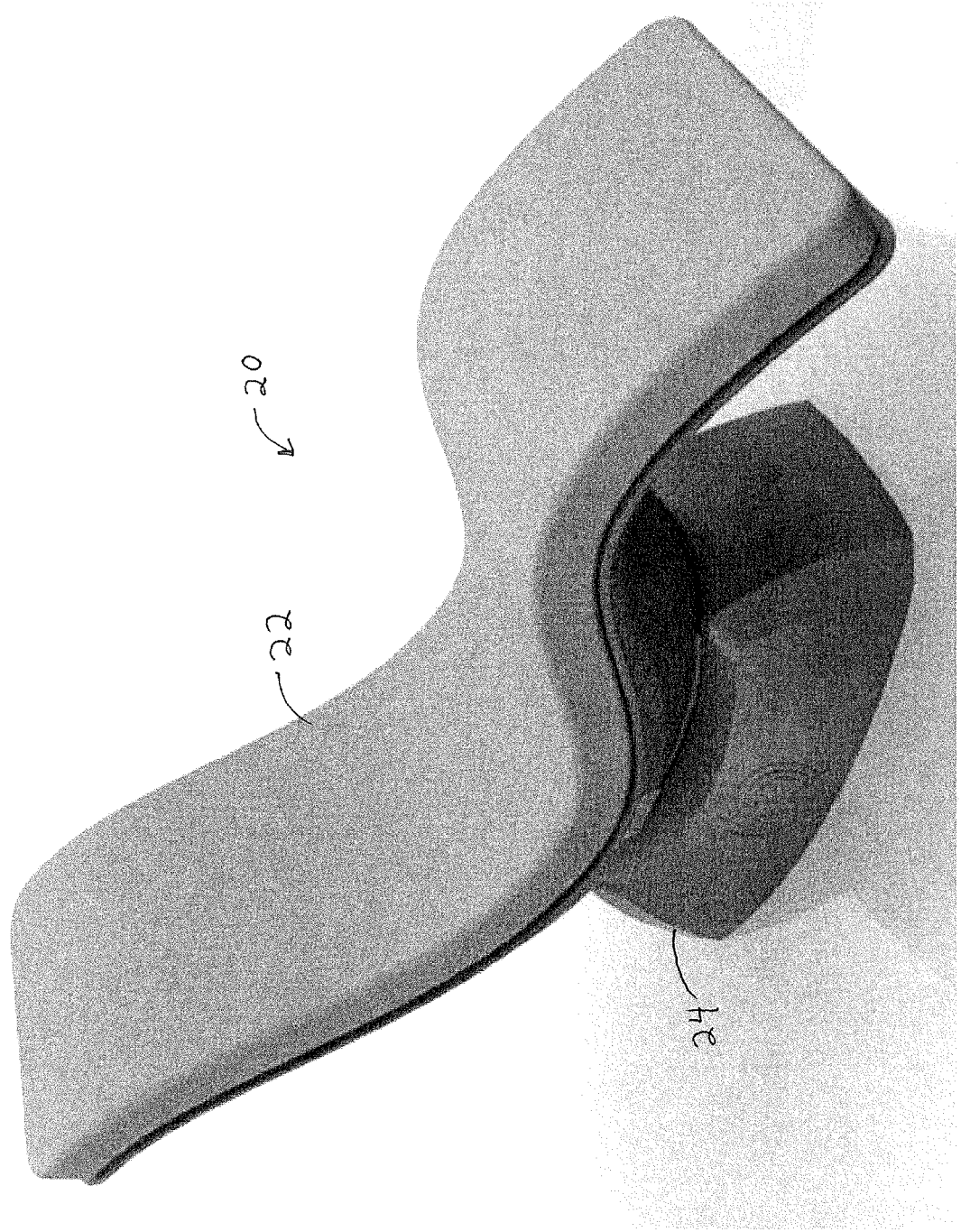
FIG. 2 is a perspective view of an embodiment of a chair of the present invention.

FIG. 2 shows an embodiment of a device of the present invention. In this embodiment, the device is in the form of a chair 20 in the style of a chaise lounge. The chair 20 includes a body-supporting structure 22 and a base 24. The device also includes an audio signal source 18 (depicted in FIG. 1), such as a CD or MP3 player.

Figures 3, 4:
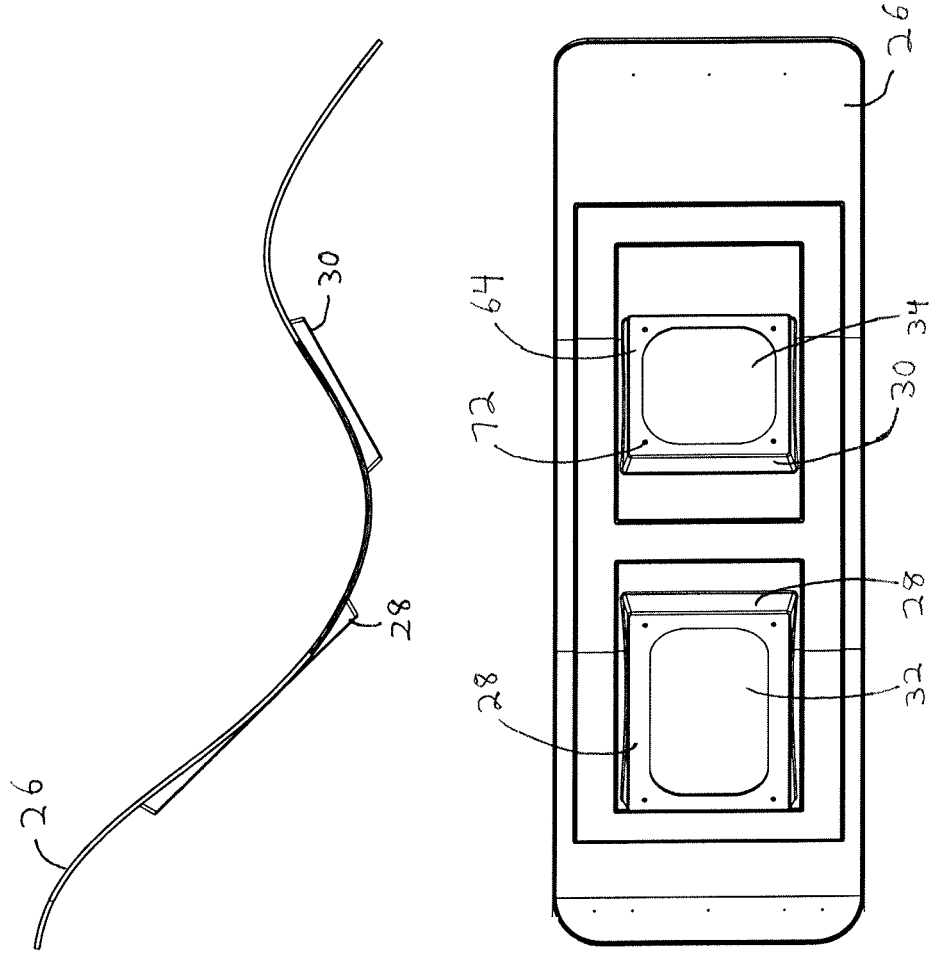
FIG. 3 is a side view of the frame of the chair of FIG. 2.
FIG. 4 is a top view of the frame of the chair of FIG. 2.

FIG. 3 is a side view of the frame 26 of body-supporting structure 22. FIG. 4 is a top view of frame 26. In one embodiment, the frame 26 is made from fiberglass. However, the frame may be made from various materials, such as but not limited to plastic and resin materials. The frame 26 includes a well 28, which includes an aperture 32 for audio speakers, and a well 30, which includes an aperture 34 for a transducer including a mass-loaded cone. Each well is approximately one inch deep.

Figure 5:
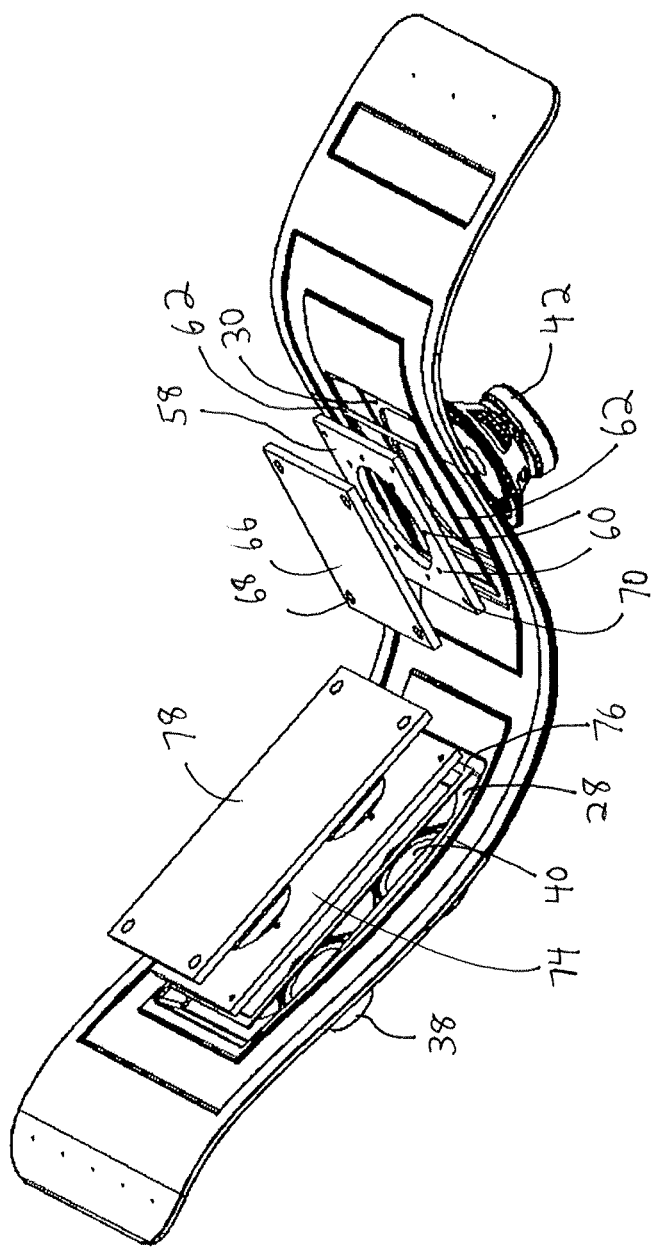
FIG. 5 is an exploded perspective view of the body-supporting structure of the chair of FIG. 2.
Figure 6:
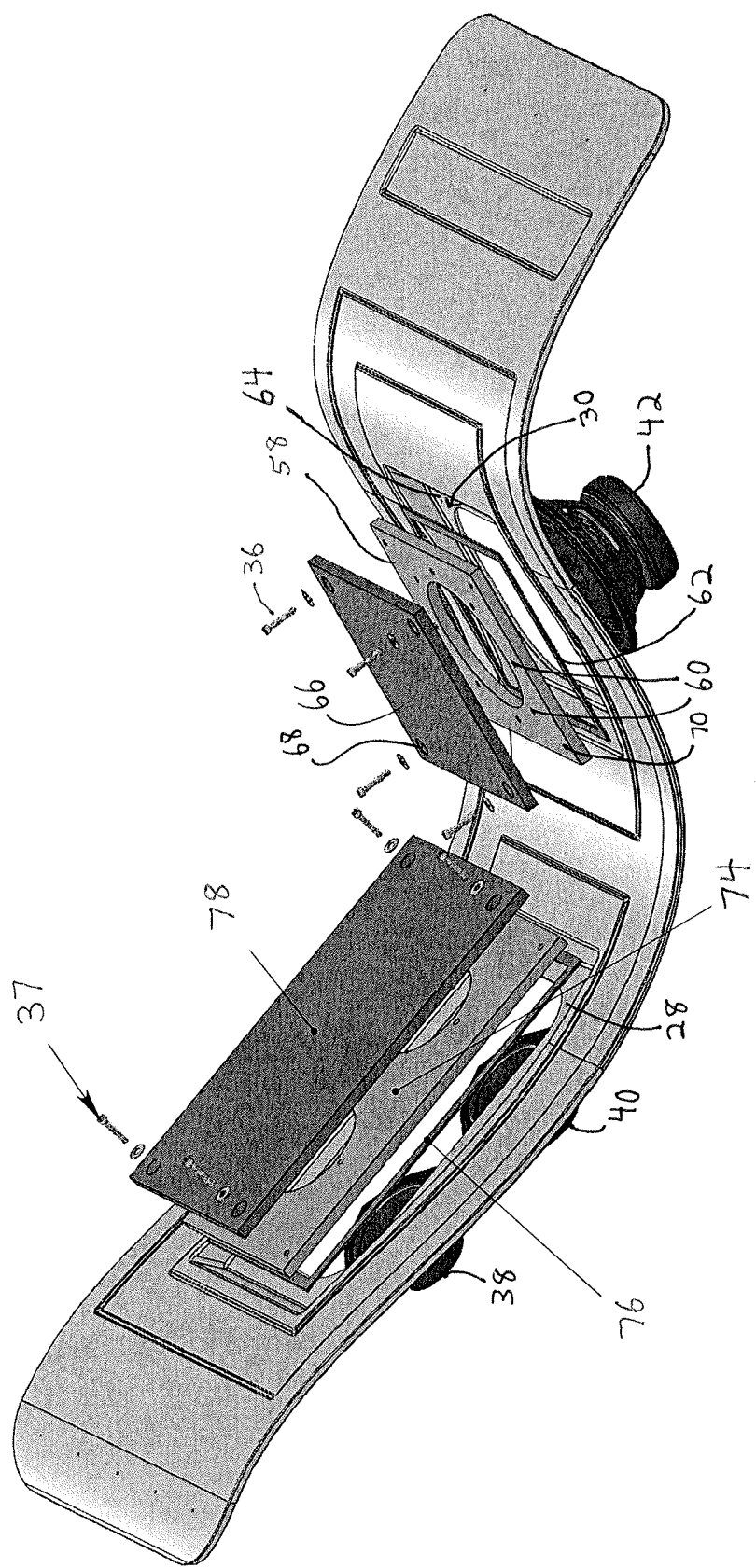
FIG. 6 is an exploded perspective view of the body-supporting structure of the chair of FIG. 2.

FIGS. 5 and 6 show exploded perspective views of the body-supporting structure 22 of the chair 20, after the upholstery is removed. The upholstery provides approximately 3 inches of foam padding on top of the frame 26. FIG. 6 shows fasteners 36 and 37 which are not shown in FIG. 5. As shown in both FIGS. 5 and 6, audio speakers 38 and 40 are positioned underneath aperture 32 of well 28, and a transducer 42 including a mass-loaded cone is positioned underneath the aperture 34 of well 30. Audio signals from the audio signal source 18 are transmitted through the audio speakers 38 and 40 and the transducer 42, thereby generating sound and vibration. The speakers 38 and 40 are positioned in the back of the chair 20, while the transducer 42 including a mass-loaded cone is positioned in the seat of the chair 20. Although the embodiment depicted in FIGS. 5 and 6 includes two speakers and one transducer including a mass-loaded cone, other embodiments of the present invention may include different numbers of speakers and/or transducers.

Figure 7:
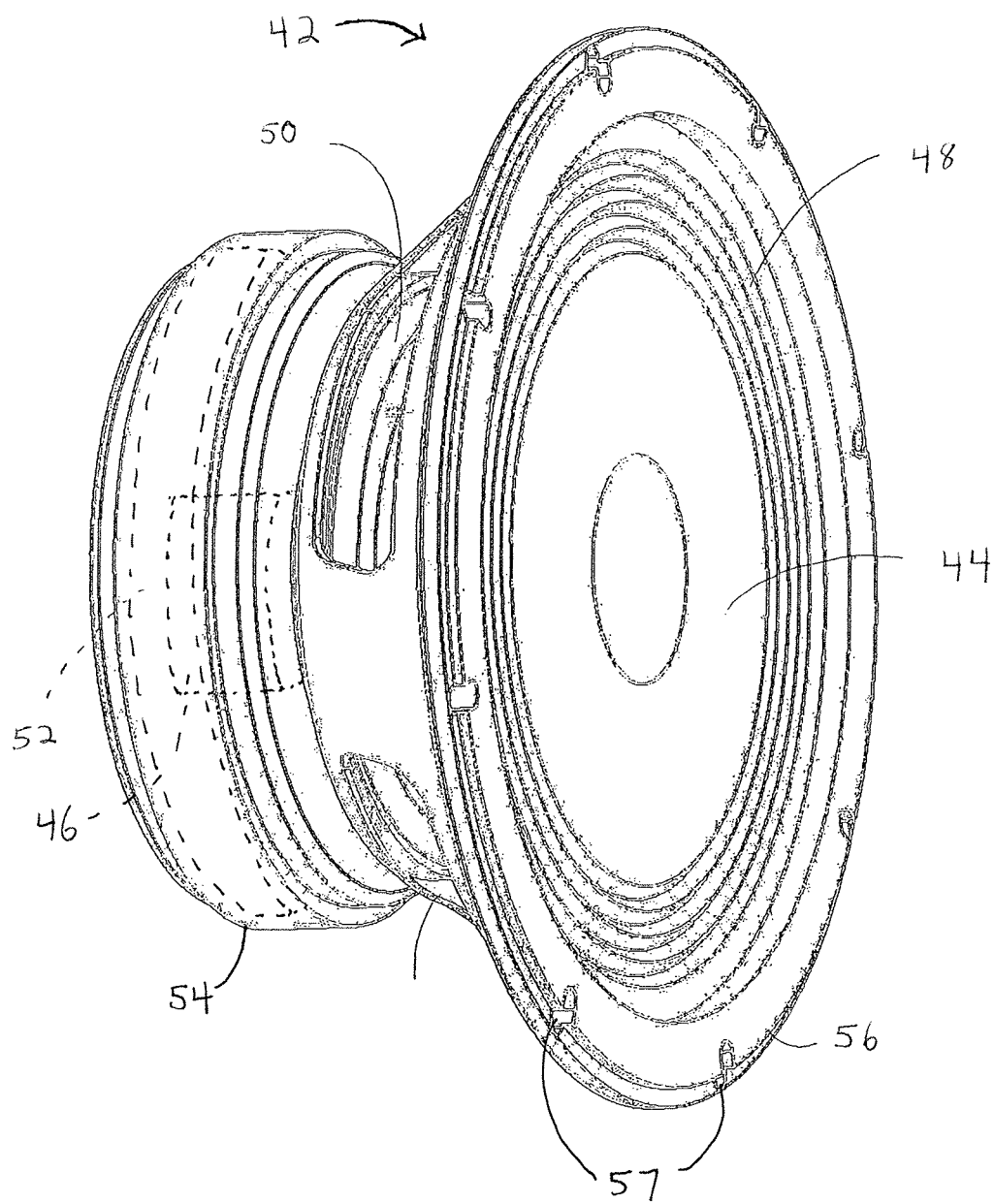
FIG. 7 is a perspective view of a transducer used in the chair of FIG. 2.

FIG. 7 is a perspective view of transducer 42. In the embodiment shown in FIGS. 5 and 6, the transducer 42 is approximately 8 inches in diameter. It does not include a traditional speaker cone. Instead of a traditional speaker cone, the transducer 42 includes a mass-loaded cone 44, which moves when the transducer is operating. In one embodiment, the mass-loaded cone 44 comprises approximately one pound of aluminum. The mass-loaded cone 44 is attached to the voice coil 46 of the transducer 42 using a double spider suspension. The transducer 42 includes an upper spider 48 and a lower spider 50. The spider suspension may be made from a cloth that has been stiffened with epoxy. The transducer also includes a permanent magnet 52 and a speaker basket 54. The rim 56 of the speaker basket 54 includes apertures 57. In one embodiment, the peak to peak power of the transducer is 150 watts. The transducer is capable of producing vibrational frequencies from approximately 0.5 Hz to approximately 1,000 Hz, and has a crossover frequency of approximately 14 Hz to 75 Hz. The transducer is also capable of producing sound frequencies from approximately 20 Hz to approximately 8,000 Hz.

Standard transducers, such as audio speakers, used to produce sound do not create a dynamically fluctuating electromagnetic field of sufficient magnitude to stimulate the human energy system. This is because the larger magnet, or permanent magnet, in such a transducer is fixed in position and produces only a weak static electromagnetic field that does not dynamically fluctuate in frequency as a result of the incoming varying voltage from the amplified sound source. A dynamic electromagnetic field capable of producing the full range of audio frequencies is generated by the voice coil of a traditional speaker, but that field in isolation is too small to stimulate the human energy system.

In order for the transducer's larger magnet, or permanent magnet, to produce a stronger dynamically fluctuating electromagnetic field and thereby stimulate the human energy system to provide optimal benefits, the transducer must have four capabilities. First, the permanent magnet must be large enough to generate a significant magnetic field when it is set into motion. Second, the permanent magnet must have the freedom to move in space. Third, the permanent magnet or the assembly that contains the magnet must be propelled to move in response to the varying voltage of the amplified sound source. Fourth, the transducer must receive and respond to a wide range of audio frequencies. If the frequencies which the transducer receives and responds to are limited, such as by filtering out high frequencies so they do not pass through the transducer, benefits of EPVS can still be attained. However, allowing the transducer to receive and respond to a wide range of audio frequencies, including frequencies up to approximately 20,000 Hz, provides a greater degree of stimulation to a user's energy system.

When the permanent magnet 52 of a transducer 42 suitable for use in the present invention is set in motion, creating a relatively large dynamic magnetic field, the smaller dynamic (and with broader frequency content) magnetic field associated with the voice coil 46, and contained within the larger field and slightly more proximal to the subject, is capable of interacting with the larger field. It is important to note that this smaller magnetic field contains all of the audio frequencies that are generated by the sound source. As such, an interaction between the two fields produces additional higher frequency content in the larger field capable of stimulating the human energy system. The interaction is not likely to produce frequency cancellation as there is a phase delay of the larger field associated with the time it takes for the force-counterforce effect to result in physical motion of the permanent magnet 52, because the process is instigated by movement of the voice coil 46 followed by movement of the mass-loaded cone 44 and then resulting in movement of the permanent magnet 52. In addition, the larger dynamic field, due to the mechanical damping effects of the mass-loaded cone 44 and the resistance to motion of the permanent magnet 52 or structure containing it, filters out some of the higher frequencies.

In order for the transducer 42 to also synchronously produce sound and vibration, its mass-loaded cone 44 must be able to move air and to impart some of the force-counterforce effect upon a structure that makes contact with the subject.

As mentioned, the voice coil attached to the cone of a typical sound-emitting transducer produces only a very small dynamically fluctuating electromagnetic field in response to the amplified sound source. This small electromagnetic field interacts with the static electromagnetic field of the large or permanent magnet, in a typical sound-emitting transducer, propelling the cone up and down based upon the varying voltage of the amplified sound source.

Transducers that produce mainly sound have lightweight cones constructed of paper or plastic to move the air in response to the varying voltage. Transducers that produce mainly vibration may employ a mass-loaded cone in order to create a force-counterforce effect on whatever structure the transducer is attached to, resulting from the varying voltage from the amplified sound source. Typically the transducer, in order to impart vibration to the attached structure, will be firmly attached, so as to maximize energy transfer to the attached structure in the form of vibration.

In the present invention, to allow for movement of the assembly that contains the permanent magnet, the transducer is not firmly attached to the structure of the delivery platform (chair, bed frame, etc.). Instead, in order to create a larger, dynamically fluctuating electromagnetic field, the assembly is loosely coupled to the structure of the delivery platform or coupled to a flexible aspect of the structure that allows it to have some freedom of motion.

In the embodiment shown in FIGS. 2-7, loose coupling of the transducer 42 to the frame 26 allows movement of the permanent magnet 52. Additionally, the cone 44 of the transducer is mass-loaded with one pound of aluminum to provide enough force-counterforce to propel movement of the permanent magnet 52, or the structure (speaker basket 54) containing that magnet, in response to the motion of the cone 44. In this manner, the normally small, static magnetic field of the permanent magnet 52 becomes larger and dynamically active by virtue of its motion.

Since the mechanical receptors of the human body (Pacinian corpuscles) can typically only register vibrations below approximately 400 Hz, typical transducers used to create vibration are designed to only produce vibration below this threshold. The varying voltage supplied to these transducers is generally filtered so that higher frequencies (typically over 100 Hz) are not supplied to the transducer. However, the human energy system responds to frequencies that are beyond this threshold. In the course of developing the present invention, it has been found that supplying frequencies up to 20,000 Hz achieves the unexpected result of stimulation of the human energy system, with the higher frequencies adding significant stimulation. When frequencies up to approximately 20,000 Hz (i.e. all audio frequencies) are not filtered out and, instead, are allowed to pass through to the transducer 42, the voice coil 46 receives the audio frequencies. As a result, a magnetic field containing frequencies up to approximately 20,000 Hz is generated around the voice coil 46. The higher frequencies (above approximately 1,000 Hz) are not of sufficient magnitude to noticeably move the transducer assembly. Therefore, because there is no movement of the permanent magnet 52 at these higher frequencies, the permanent magnet 52 does not produce these higher frequencies in its magnetic field. Instead, the voice coil 46 creates a smaller magnetic field that contains higher frequency magnetic waves. This smaller field interacts with the lower frequency magnetic field that is produced by the permanent magnet 52. The lower frequency magnetic field surrounds and permeates the smaller field and is thereby changed by it. Accordingly, although not intending to be bound by theory, it is believed that higher frequencies from the magnetic field generated around the voice coil 46 are imparted to the larger magnetic field generated by the permanent magnet 52, and are transmitted by the larger magnetic field to impact the human energy system.

With reference to FIGS. 5-7, motion of the transducer 42 is allowed by the manner in which the transducer 42 is coupled to the frame 26. The transducer 42 is attached to a board 58, using fasteners such as bolts which pass through apertures 57 in the transducer 42 and apertures 60 in the board 58. In the embodiment shown in FIGS. 5 and 6, the board 58 is made from wood, but in other embodiments it may be made from other materials, such as plastics. A foam gasket 62 is placed between the board 58 and the base 64 of the well 30. A foam layer 66 is placed on top of the board 58. Fasteners 36, which are bolts in the embodiment shown in FIG. 6, pass through apertures 68 in the foam layer 66, apertures 70 in board 58, and apertures 72 in the base 64 of the well 30 (shown in FIG. 4). The board 58 is not tightly bolted to the base 64 of the well 30. Instead, the board 58 is loosely coupled to the base 64 of the well 30, so that the board 58 and transducer 42 are able to move in a direction perpendicular to the plane of the board 58. The foam gasket 62 prevents the board 58 from making noise when the board 58 moves toward base 64 of the well 30. The compression of the foam gasket 62, which is approximately 3/16 of an inch (0.1875 inch) thick, allows room for the board 58 to move closer to the base 64 of the well 30, due to the motion of the transducer 42. The transducer subassembly (i.e. the transducer 42 and board 58) is able to move approximately 1/8 of an inch (0.125 inch) perpendicular to the plane of the board 58. A greater amount of movement may be allowed through the use of compressible foam for the foam layer 66. Moreover, in other embodiments of the present invention, a different amount of motion of the transducer subassembly may be allowed by, for example, using a foam gasket 62 of a different thickness.

Even though the transducer 42 is only loosely coupled to the frame 26, sufficient vibration is still imparted to the structure of the chair 20, and the vibration is able to be distributed throughout the frame 26, as the entire frame is made from fiberglass. However, materials other than fiberglass may also be used to create a frame that would allow vibrations to be distributed throughout the structure. For example, in other embodiments of the present invention, the frame may be made from materials other than fiberglass, such as but not limited to plastic and resin materials. Moreover, in other embodiments, the frame may have a different form from that shown in FIGS. 2-6.

The audio speakers 38 and 40 are also coupled to the frame 26. With reference to FIGS. 5 and 6, the audio speakers 38, 40 are attached to board 74 using fasteners such as bolts. Board 74 may be made from materials such as wood or various plastics. A foam gasket 76 rests between the base of the well 28 and the board 74, and a foam layer 78 rests on top of the board 74. Fasteners 37 such as bolts pass through apertures in the foam layer 78, board 74, and the base of the well 28, thereby coupling the audio speakers 38, 40 to the frame 26.

In some embodiments, a device in accordance with the present invention may also include an electromagnetic driver positioned in close proximity to a user's abdomen. The driver contains a magnet and is capable of producing vibrations. This driver may be a speaker or a transducer, and may be used alone or in conjunction with a driver located in a body-supporting apparatus. A driver that straps to a user's abdomen may aid in producing sufficient vibrations to penetrate the user's abdominal fat.

The five mechanisms through which health benefits are believed to be provided, through the use of the present invention, are discussed below.

Mechanism 1: Neuropsychological Mechanism: Administering Sounds and Vibrations to Induce Profound Therapeutic Relaxation and Meditation-Like Mind Conditioning to Normalize Autonomic Nervous System, Neuro-Endocrine, and Immune System Functioning and Reduce the Harmful Effects of Adrenaline and Cortisol (Profound Therapeutic Relaxation/Anti-Stress Response).

Chronic stress and the inability to relax and reset the body's normal homeostatic balance is known to cause and/or worsen many disease states ranging from insomnia, anxiety and depression, obesity, autoimmune diseases, and high blood pressure (leading to heart disease and stroke) to even the spread of cancer. The medical and anti-aging benefits of relaxation and meditation have been scientifically documented.

Since the days of our early ancestors we have been endowed with a nervous system that has a built-in, hard-wired survival mechanism. With this mechanism we are always scanning our environment, consciously and subconsciously, for potential danger. This mechanism is supported primarily by three of our senses: sight, hearing, and touch.

We use our senses of sight (visual), hearing (auditory), and touch (somatosensory), in that order, to survey our environment for danger. These three sensory inputs provide information to our nervous system, which allow our survival instinct and our defense mechanisms in general to manifest. Everyday stressors trigger this neurologic system which initiates the output of adrenaline and cortisol, the two hormones that support the fight or flight response (sympathetic division of the autonomic nervous system). When this system is overused, as results from chronic stress, disease states ensue due to the harmful effects of prolonged exposure to these hormones.

Sight provides the earliest possible warning, followed by sound and then touch. This hierarchy reflects the physical properties of the stimuli and the distance from the person required to stimulate the specific sense. Signals from the primary sensory nerves (optic, auditory, and peripheral somatic nerves) connect to the amygdala (more primitive area of the brain). These signals are registered there even before they are transmitted to their respective target areas of the cerebral cortex (the thinking brain). Due to the nature of the amygdala and its connections within the nervous system, the individual can more rapidly and instinctively determine if the stimulus received is similar to any stimulus received in the individual's past that is considered dangerous. The person is then able to initiate whatever action is necessary to avoid harm, even before the signal registers in the person's conscious awareness.

It is the function of the nervous system and in particular, the amygdala and related structures that manifest our survival instinct and defense mechanisms. These structures and the activation level within the nervous system at large that they cause and maintain, give rise to our level of alertness and arousal or when excessive, our level of stress. When this system is over-used or over-attended to, as in the case of chronic stress, the person tends to have an imbalance in their autonomic nervous system functioning, with greater sympathetic than parasympathetic activation resulting in exposure to the harmful effects of chronic stress mediated by adrenaline and cortisol and direct sympathetic nervous system stimulation. The relaxation response is intended to reset this system and readjust the body's homeostatic balance in order to reduce the stress imposed on the body.

While in a session in which EPVS is administered in accordance with the present invention, there is no need for the subject to worry about survival, so the subject's survival mechanism may be turned off. This is accomplished by systematically turning off the senses of sight, hearing and touch, as discussed below.

In an embodiment of a method of the present invention, in a session in which EPVS is administered to a subject, the room is darkened and the subject is instructed to close his or her eyes and fall asleep. As a result, his or her visual system receives no stimulus (i.e. visual stimuli are turned off). With regard to the sense of hearing, the auditory stimulus used during the EPVS session is typically layered music/sounds or music that is not very engaging. The auditory stimulus is generally perceived as pleasurable to the subject. In layered music, multiple melodies are played simultaneously so it is difficult for the subject's brain to follow the music. The psychoacoustic properties of the layered sound result in listening fatigue causing the user to mentally disengage. Therefore, the user stops listening. With regard to the sense of touch, the music contains bass and mid-range frequency content which the transducers turn into vibration. The music contains an amount of bass and mid-range frequency content that is sufficient to cause the subject to feel vibration throughout the session. Due to the high density of low frequencies that can be felt, the user's nervous system habituates to the feeling experience thereby "shutting off" the sensory modality of touch in addition to the auditory and visual modalities.

With standard (non-EPVS) relaxation response practices, the sense of touch is left in its normal state, poised to sense danger. Given its hierarchical level of importance (the closest-in warning sense) and with the other senses turned off, it has the ability to produce an even more heightened level of arousal. However, using EPVS in accordance with the present invention, all of the subject's senses associated with maintaining a vigilant state are turned off. The relatively constant sound and vibration cause the neural circuitry associated with hearing and touch to stop attending to the stimuli—the sensory systems become habituated. As a result, these portions of the nervous system become inhibited. Turning off all of the circuitry related to sight, hearing, and touch, which supports the survival mechanism causes subjects to become far less vigilant or tense and as a result they drift toward sleep. Moreover, in an embodiment of the method of the present invention, the subjects are instructed to fall asleep. Therefore, when beginning to attend EPVS sessions, subjects generally fall asleep.

However, two of the stimuli provided, vibration and sound, which stimulate the senses of touch and hearing, are the most effective at waking the subject. As a result, within a few EPVS sessions, subjects find themselves floating between sleep and reduced wakefulness. In this manner the subjects can easily learn to become aware of their sleeping bodies. In that state subjects feel extremely relaxed because a body at sleep is at its most physiologically relaxed state. With practice, subjects learn to recreate this feeling state at will, thereby creating a profoundly relaxed state whenever they choose.

Psychologically, with the use of EPVS in accordance with the present invention, the subject has been moved from a state of subconscious surveillance to one of welcome and willing sensory engagement. This state is diametrically opposed to that associated with the state of surveillance associated with one's survival instinct and other defense mechanisms. As a result, the individual automatically becomes less aroused and more relaxed.

Therefore, most subjects using EPVS-based therapy in accordance with the present invention experience, on an involuntary basis, a profound state of relaxation, often with a significant reduction in conscious awareness simulating a very deep meditative state. Fortunately, there is little if anything required of the user to initiate this state. It is in this state that the body's natural healing best occurs as the autonomic nervous system is shifted from sympathetic to parasympathetic activation, which promotes healing rather than fight or flight and a dramatic reduction in adrenaline and cortisol and direct sympathetic nervous system stimulation.

In some embodiments of the present invention, the music/sound that is used to accomplish the above mechanism of action is unlike music that people listen to for pleasure. Specifically, the sound/music content is typically a layered compilation of two or more selections or titles of what is considered to be music (typically instrumentals) with or without sounds (nature sounds for example). To create a layered compilation of music selections (hereinafter referred to as "layered music"), the multiple music selections with or without sounds are played simultaneously.

The music and sounds are preferably composed and compiled in a manner that produces a relatively constant exposure of lower frequencies (under 400 Hz). Since our sensory ability to feel vibrations are sensitive at these levels (peak responsiveness of vibratory sensors in the skin include Pacinian corpuscles at about 250 Hz and Meissner's corpuscles at about 50 Hz), it is important to have significant frequency content in this range to facilitate the user's ability to feel the music content so that he or she habituates to it. Moreover, lower frequencies are more effective at penetrating tissues of the body.

Habituation allows the nervous system to optimize sensory-motor processing by eliminating unnecessary responses. It adapts to the familiar. Therefore, the large expanse of the somatosensory cortex and associated areas of the nervous system exhibit reduced responsiveness by providing a relatively constant exposure to low frequencies that stimulate the aforementioned receptors and are easily felt. The central nervous system that is involved with this sensory information thus "tunes out" the constant exposure. Since there is no other tactile sensory information to pay attention to there is reduced neural processing in these areas.

Preferably, the layered music also contains various and repetitive higher frequency melodic segments, which occur at random intervals. These segments contain frequency content that is generally too high to feel. These segments play simultaneously with the lower frequency content and serve several other functions. They are more pleasant to listen to so the user's experience is more pleasurable. Without these segments the music tends to be more somber and heavy. The higher frequency segments lighten the mood of the content. Moreover, as discussed below in connection with Mechanism 2, supplying higher frequencies adds significant stimulation to the human energy system.

Since these more melodic segments are more interesting to listen to, the user will pay attention to them. However, because these segments are short-lived and randomly appear and disappear, the user cannot follow any progression or make any musical sense of them. As a result, the user tends to experience psychoacoustic listening fatigue and they disengage from active listening. This is another example of habituation causing these other areas of the central nervous system to become less active.

Preferably, sessions in which users are exposed to EPVS in accordance with the present invention are carried out in a dark room so there is no visual stimuli. Typically the users close their eyes. The environment is also free of odors. As a result, the users exist in a state of sensory deprivation even though they are being stimulated with sound and tactile stimuli. This results in a profound state of hypo-arousal and a shift of autonomic balance from sympathetic to parasympathetic preponderance. It also typically results in a deepened state of mindlessness such that conscious awareness is lost. Users typically feel exceedingly relaxed after the completion of a session. With repeated sessions, users learn what it feels like to become progressively more relaxed and therefore are able to better emulate that state.

In the right circumstances, sound and touch can cause increased arousal and alertness, which during times of reduced conscious awareness, can be of benefit. When subjects are in a deeply relaxed state with reduced awareness due to EPVS, subjects can become more consciously aware when there is a significant increase in audible sound and vibration due to a change in the sound source. Subjects can then become consciously aware of how they feel during deeper levels of relaxation. As a result, it is easier for subjects to recreate that feeling and level of relaxation in future sessions and outside of the practice sessions.

The treatment of essential or primary hypertension is an excellent model for understanding the effect of this mechanism of action of EPVS (mechanism 1). For decades, heart disease has been the number one and stroke, the number three cause of death in the United States. Hypertension or high blood pressure is the leading cause of stroke and a major cause of heart disease. In fact, hypertension is considered to be the most common cardiovascular disease, affecting an estimated one in four or 80 million Americans.

Hypertension is often referred to as the silent killer because it is clearly one of, if not the main culprit in causing heart disease and stroke. Hypertension can result from kidney, thyroid, and adrenal diseases as well as from Sleep Apnea and other conditions. However the majority of cases, approximately 90% of patients with hypertension, are considered to have essential or primary hypertension, which means that the hypertension is not the result of another medical condition.

The pharmaceuticals used to treat hypertension often change the systolic (upper) and diastolic (lower) blood pressure numbers, but not the underlying cause. Although this can be effective in reducing the complications of hypertension, many patients are not compliant with their prescriptions due to side effects or costs. As a result they go untreated and remain predisposed to the complications of this malady. In addition, the underlying cause also continues to go untreated, whether anti-hypertensive medications are used or not.

Blood pressure, like most physiologic parameters, is responsive to the actual or perceived needs of the body. The nervous system of an individual sends signals to the heart, blood vessels, and endocrine glands that determine how fast the heart pumps blood and the degree of arterial dilation. When the heart pumps faster and the arteries are less dilated, blood pressure rises.

When the brain tells the body to maintain a higher level of blood pressure more regularly, the body adjusts its baseline physiology (homeostasis) so that this new level of blood pressure is maintained. This is how essential hypertension is created—the body's perceived essential needs are met by a heightened level of blood pressure.

For decades, medical researchers and physicians have known about the mind/body connection and how the body serves the perceived needs of the mind. When the mind thinks that an action may be required it tells the body to prepare itself. This is where stress enters the equation.

Stress is anything that has the potential to trigger a negative physical, emotional, or mental response. Financial worry can be stressful if it is reacted to negatively creating fear, anxiety, and worry. Criticism can be stressful if it is reacted to negatively creating frustration or anger.

If the response to potentially stress-producing circumstances leads to fear or anger then the mind signals to the body to prepare itself to take action. If the action is in response to fear or anger then it typically falls into the category of fight or flight (sympathetic nervous system activation versus parasympathetic activation). In either case, the body believes it will need a higher level of blood pressure in order to fight or run in anticipation of the physical demands. This is how essential hypertension is created—when the body perceives that a higher level of blood pressure is required, whether or not the need is real or imagined.

Even mild stress producing circumstances create a fight or flight response. These repeated and often subtle sequences of events cause a physiologic cascade resulting in higher blood pressure. Chronic states of elevated fear, anxiety, frustration, anger, and even an unwillingness to forgive or accept ourselves, other people, and our circumstances can result in these effects. When these psychological and physiologic states recur repeatedly they are often not consciously perceived. The new level of anxiety/fear and anger/frustration become the norm. Blood pressure simply follows suit and rises to meet the perceived needs associated with the manifest tension.

Extensive studies performed at many centers around the world have demonstrated that teaching relaxation exercises reduces blood pressure. Accordingly, the administration of EPVS-based therapy in accordance with the present invention may reduce blood pressure by inducing profound therapeutic relaxation.

The response to stressful situations can affect the body in other ways as well. It can raise heart rate and blood pressure, increasing the heart's need for oxygen. The nervous system can cause an excessive release of hormones (most often adrenaline and cortisol). These hormones raise blood pressure and can injure the lining of the arteries. When the arteries heal, the walls may harden or thicken, making is easier for atherosclerotic plaque to build up. Stress has also been associated with elevated cholesterol levels, leading to an increase in atherosclerotic plaque. Moreover, the response to stress can increase the amount of blood clotting factors that circulate in blood, and makes it more likely that a clot will form. Clots may then block an artery and cause a heart attack or stroke. People who respond negatively to stress may also overeat for comfort, start smoking, or smoke more than they normally would. These are additional risk factors for cardiovascular disease. While not intending to be bound by theory, the relaxation response induced by EPVS-based therapy in accordance with the present invention may work to counteract the effects of stress, by resetting the body's autonomic nervous system and readjusting the body's homeostatic balance.

Although primary hypertension provides an instructive example of how EPVS can produce beneficial health effects resulting from mechanism 1, other mechanisms of action can be synergistically applied to increase effectiveness. For instance, mechanisms 2, 3, and 4 could come into play at the level of the kidney affecting the rennin-angiotensin system that can have a large impact on blood pressure regulation. In addition mechanism 3 could be used to stimulate nitric oxide (relaxes smooth muscle contraction in arteries and arterioles) production and/or release from the endothelial lining of blood vessels and paranasal sinus cavities, which also lowers blood pressure.

Although mechanism 1 has been discussed above as resulting from EPVS, mechanism 1 can also result from vibration and sound that is not electromagnetically produced. Moreover, mechanism 1 can result from the administration of vibration and sound alone, without the presence of a magnetic field. However, if the synergistic effects resulting from the addition of mechanism 1 and mechanism 2 (and/or the addition of mechanisms 1 and 3) are desired, then the vibration and sound must be administered in the presence of a magnetic field.

Mechanism 2: Energetic Mechanism: Using a Dynamically Fluctuating Electromagnetic Field to Stimulate a Person's Energy System.

As discussed above in connection with mechanism 1, EPVS sessions in accordance with the present invention provide vibration and sound stimuli to a subject. There is one more stimulus provided that is exceedingly beneficial—synchronized magnetic field stimulation to the person's energy system, which includes chakras located at the base of the spine and beneath the feet. The root chakra at the base of the spine, in particular, is an energetic structure that is associated with feelings of safety and security and a person's right to be present in his or her body. In the course of developing the present invention, it has been unexpectedly found that by stimulating the lower energy system in this way there is an increase in spiritual energy flow. Those people who are able to feel their energy system can immediately feel the difference. Others can learn to feel their energy systems with the use of the technology of the present invention.

Greater spiritual presence within the body promotes greater feelings of relaxation and comfort. More importantly however, greater spiritual presence is the fundamental ingredient for spiritual growth. With greater spiritual integration the subject does not feel negative emotions and is far less likely to be triggered by stress-provoking events. This process supports a philosophical approach to spiritual growth which consists of embodying our spiritual selves and being fully present in body and life.

The administration of EPVS in accordance with the present invention may lead to both greater relaxation and spiritual growth. By nearly falling asleep or actually being asleep, the ego or conditioning of the individual, which is a function of the brain, is rendered less or non-functional. When the individual's consciousness (awareness) begins to awaken, while leaving the body/brain nearly asleep or asleep, the individual can perceive his or her nearly asleep or sleeping body. In this way individuals can observe how their body feels (heaviness of arms and legs, regular and automatic nature of their breathing, feeling that they are not their body, etc.) and learn to recreate those feelings to learn maximal levels of relaxation. The reason that the individual can perceive during this state of consciousness is that "the perceiver" is the person's authentic self/soul/higher self or higher mind, which is not a function of the brain—as occurs in out-of-body experiences or near death experiences. It is also that part of us that experiences mindfulness—it is the higher mind observing the lower egoic mind of the personality. This process, as it continues (increasing conscious awareness with an asleep or nearly asleep body/brain) allows individuals to experience the nature of their higher mind unfettered by their conditioning or egoic self. With experience, the subjects can therefore choose to spend more time as their authentic selves, less influenced by their ego.

Mechanism 3: Inducing Electro-Mechanical Forces within and Around Cells to Facilitate Preferential Chemical Reactions.

Chemical reactions (molecular interactions leading to chemical bonding) are the foundation of the human body's anatomy and physiology. Molecules react with other molecules based upon mechanical and electrical properties; the better the mechanical and electrical fit between molecules, the higher affinity they have for one another. It can be reasonably assumed that chemical (molecular) reactions that have evolved over millions of years have the greatest affinity between participating molecules, particularly for those reactions that are important to the survival of the species.

Typically, specific functions of the body are carried out by a sequence or chain of chemical reactions. An example of such a sequence is the cascade of chemical reactions that follow the binding of the hormone insulin with the insulin receptor on the cell wall. This is also the type of chemical reaction that is important to the survival of our species and which has evolved over millions of years.

As in many chemical systems such as this, there are competing chemical reactions that predispose the resulting cascade of reactions in one of several directions. In the case of the insulin cascade, which normally causes glucose to enter cells for energy production and storage of glycogen and fats, there are competing pathways, which manifest in certain disease processes. This can cause fats to be used for energy production instead even in the presence of excessive glucose and insulin in the bloodstream.

This situation, called insulin resistance, is found in Type 2 Diabetes (T2D). Presently there are 24 million diabetics in the U.S. (90% of them are Type 2) and 54 million pre-diabetics. The World Health Organization has deemed T2D to be a pandemic with 150 million sufferers at present and expected to grow to 300 million by 2025. T2D causes vascular complications, which include retinopathy, amputations, kidney failure, heart attack and stroke. The present management of T2D using supplemental insulin or oral medications does not entirely prevent the vascular complications as it does not treat the underlying cause, insulin resistance.

The current scientific thinking as to the cause of insulin resistance is that as a result of excessive intracellular fat metabolism there is an accumulation of intracellular diacylglycerols. These substances activate protein kinase molecules that are not ordinarily involved in the typical insulin cascade of reactions. These protein kinase molecules in turn decrease the normal insulin-stimulated reactions beginning with the activity of insulin receptor substrate molecules 1 and 2, and subsequently other downstream reactions. As a result of this perturbation there is more intracellular fat metabolism and less glucose metabolism taking place. It is not an all or none process, but instead one of shifting balance, based on the prevailing cascade of chemical reactions.

The evolution of cellular metabolism utilizing glucose preferentially when available has occurred over millions of years. It has only been in recent decades that individual lifestyle and dietary changes have allowed for an alteration of the cellular environment of sufficient magnitude to create T2D. Despite that, there is no reason to believe that the affinities of the molecules involved in the chemical reactions that normally favor glucose metabolism have become less than those associated with the chemical reactions of fat metabolism. However, due to increased concentration of fat metabolites and secondary messengers, it is clear that they exert a blocking action of the normal insulin induced cascade.

Chemical reactions can be altered by mechanical forces as well as by electrical forces, as chemical reactions between molecules are dependent upon mechanical and electrical fit. By creating fluctuating mechanical and electrical forces at the level of the extracellular and intracellular environment it is more likely that the molecules with the highest affinity would undergo bonding versus molecules with less affinity. In this manner, in the presence of glucose and insulin, glucose metabolism should be increasingly favored over fat metabolism. Repeated exposure to fluctuating mechanical and electrical forces could shift the balance between glucose and fat metabolism.

In a similar fashion, it is expected that thousands of evolutionarily preferential reactions could be facilitated using this mechanism of action.

Mechanism 4: Administering Organ Specific Vibrations to Resonate Organs, Organ Sub-Structures, Tissues, and Cavities.

All matter has a resonant frequency, the frequency at which it vibrates most easily. Therefore, resonant frequencies, including their sub-harmonics and harmonics, which may also create vibrations more easily than other frequencies, can be used to more easily vibrate certain tissues.

This mechanism addresses organs, organ sub-structures, tissues, and cavities that are bounded or spatially definable in addition to organs that are less easily spatially defined. The lung serves as a good example of a structure with a number of spatially definable sub-structures, which include well defined bronchioles and bronchi. In addition, the lung is enclosed in the bounded, pleural cavity. Each of these structures has resonant frequencies. Alternatively, other structures in the vicinity that are of different geometry will vibrate less so when exposed to another structure's resonant frequencies.

By knowing and using resonant frequencies specific structures can be preferentially targeted. Additionally, structures can be sequentially targeted. Chronic Bronchitis, a lung condition, is a good example of how both targeting and sequencing the delivery of resonant frequencies can be beneficial. In Chronic Bronchitis there is inflammation, swelling, and excessive mucus production in the bronchi of the lungs. Targeting the smallest bronchi first with resonant frequencies predisposes the mucous to flow toward the larger diameter bronchi due to the relative pressure gradient between smaller bronchioles and larger bronchi. In this way the mucus can be more easily expectorated. Expectorating the mucus may be further aided by resonating the entire pleural cavity to aid in pulmonary expansion and compression. Appropriate postural positioning during this procedure can allow gravity to aid in the process in addition to increased hydration and medications that thin the mucus. In more severe cases it is important to target the larger bronchi first in order to clear sufficient space for excessive mucus secretions to be transported from the smaller bronchi and bronchioles and also to perform numerous sequencing sweeps.

Table 1 sets forth the approximate size ranges of the structures noted and the associated estimated resonant frequency ranges. The estimated resonant frequency ranges in Table 1 resulted from simplified calculations based on spherical bodies.

TABLE 1

| Structure | Size Range (diameter) | Estimated Resonant Frequency Range |
| --- | --- | --- |
| Primary Bronchioles | 0.3 mm-1 mm | 6520-21733 Hz |
| Large Bronchioles - Small Bronchi | 1 mm-5 mm | 1304-6520 Hz |
| Tertiary Bronchi | 5 mm-10 mm | 652-1304 Hz |
| Primary and Secondary Bronchi | 10 mm-25 mm | 261-652 Hz |
| Pleural Cavity | Not Applicable | 40-45 Hz |

Other organs that are bounded can also be treated in this manner. Examples include the oculus, ureter, urinary bladder, urethra, fallopian tubes, uterus, vas deferens, esophagus, stomach, small and large intestines, gall bladder, bone and bone marrow, intravascular spaces, and sinus and cranial cavities.

Using resonant frequencies is also a synergistic activity in support of mechanism 3. For instance, using the resonant frequency of solid organs such as muscle and liver in Type 2 Diabetes can cause greater tissue motion in the targeted tissue creating greater mechanical and electromotive forces to be generated. The same approach can be used for mass lesions within and around organs such as tumor masses and more consolidated infectious processes.

Mechanism 4 can result from the administration of vibration and sound alone, without the presence of a magnetic field. However, if the synergistic effects resulting from the addition of mechanism 4 and mechanism 2 or 3 are desired, then the vibration and sound must be administered in the presence of a magnetic field.

Mechanism 5: Inducing Mild Vibrations Throughout the Body to Facilitate Movement of Interstitial Fluid into the Vascular Space Promoting Increased Glomerular Filtration and Diuresis and Improved Micro-Vascular Blood Flow.

The normal exchange of fluid and nutrients between the vascular space and cells takes place through the interstitial space, which is the fluid filled space around cells. There are several causes whereby excess fluid accumulates in the interstitial space. Regardless of cause, excess fluid is best moved into the vascular space and if excessive removed in the kidneys.

Vibrations throughout the body can act as a pump to facilitate movement of excess interstitial fluid into the vascular space or into the lymph system. Excess interstitial fluid accumulates in Congestive Heart Failure (CHF) and other conditions. This mechanism of action could facilitate diuresis in CHF patients.

In cases where excess fluid produces localized swelling there can be impairment of micro-vascular blood flow. Swelling in post-thrombophlebitis patients, for example, leads to this type of problem with the potential for developing decubitus ulcers. By reducing the swelling, micro-vascular blood flow can be improved in these patients.

Mechanism 5 can result from the administration of vibration alone, without the presence of a magnetic field. However, if synergistic effects resulting from the addition of mechanism 4 and mechanism 2 or 3 are desired, then the vibration must be administered in the presence of a magnetic field.

Examples

Administration of EPVS to Human Subjects

A study was conducted on human subjects ("the EPVS study") using a device in accordance with the present invention, as represented by the block diagram of FIG. 1, in which the support structure 16 was a recliner containing electromagnetic drivers 12 which produced EPVS. Two of the electromagnetic drivers were speakers located in the back of the recliner, while one electromagnetic driver was a transducer located in the seat of the recliner.

In each treatment session of the EPVS study, a subject sat in a recliner while music played through the electromagnetic drivers of the recliner. Sound and vibrational energy from the music was transmitted from the speakers of the recliner, while vibrational energy was transmitted from the transducer of the recliner. In this manner, EPVS was administered to each subject. Each treatment session lasted 68 minutes, and the sessions were conducted three times per week unless stated otherwise.

The music played through the electromagnetic drivers of the recliner was layered music, as described above in the discussion of Mechanism 1. To produce the layered music used in this study, three different sound tracks were played simultaneously. The layered music was produced from a variety of compositions that contained a broad spectrum of sound, including many low and mid-range frequencies.

Figure 8:
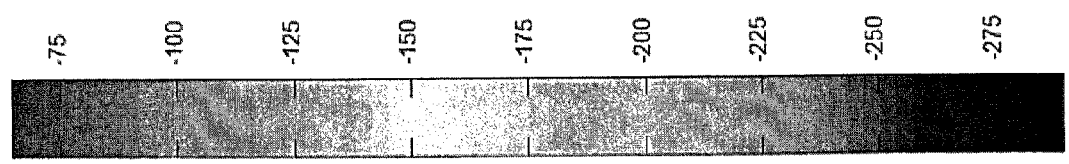
FIG. 8 is a graphical representation of a time-frequency spectral analysis of layered music used to practice a method of the present invention.
Figure 8:
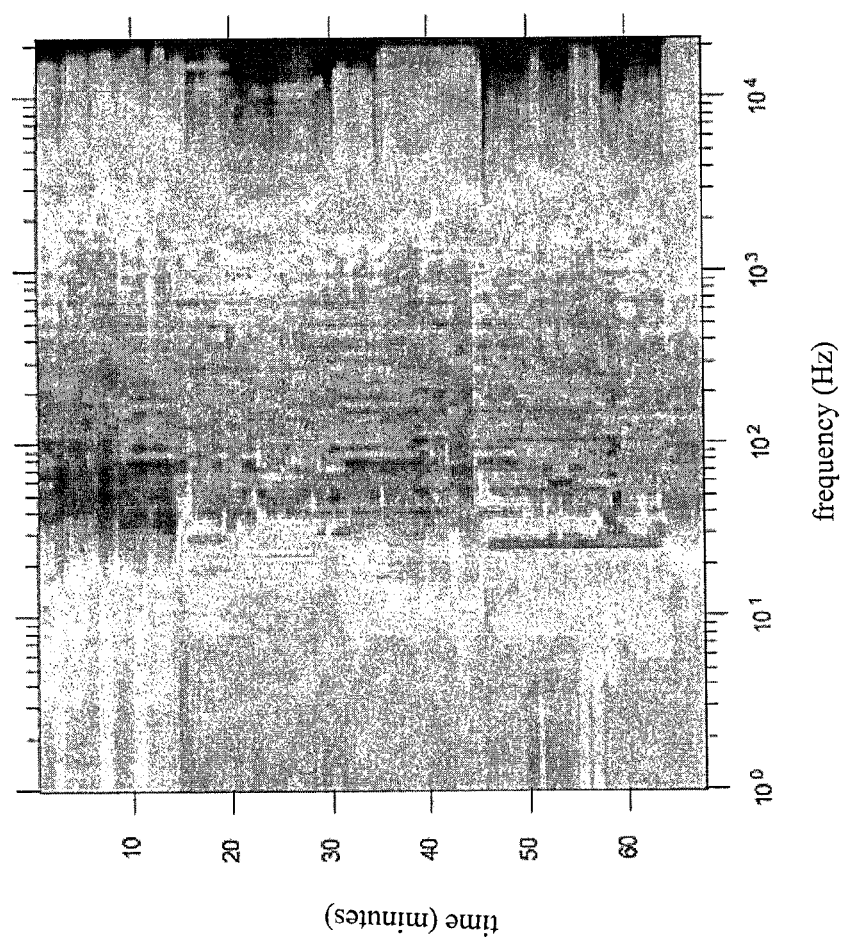
Figure 9:
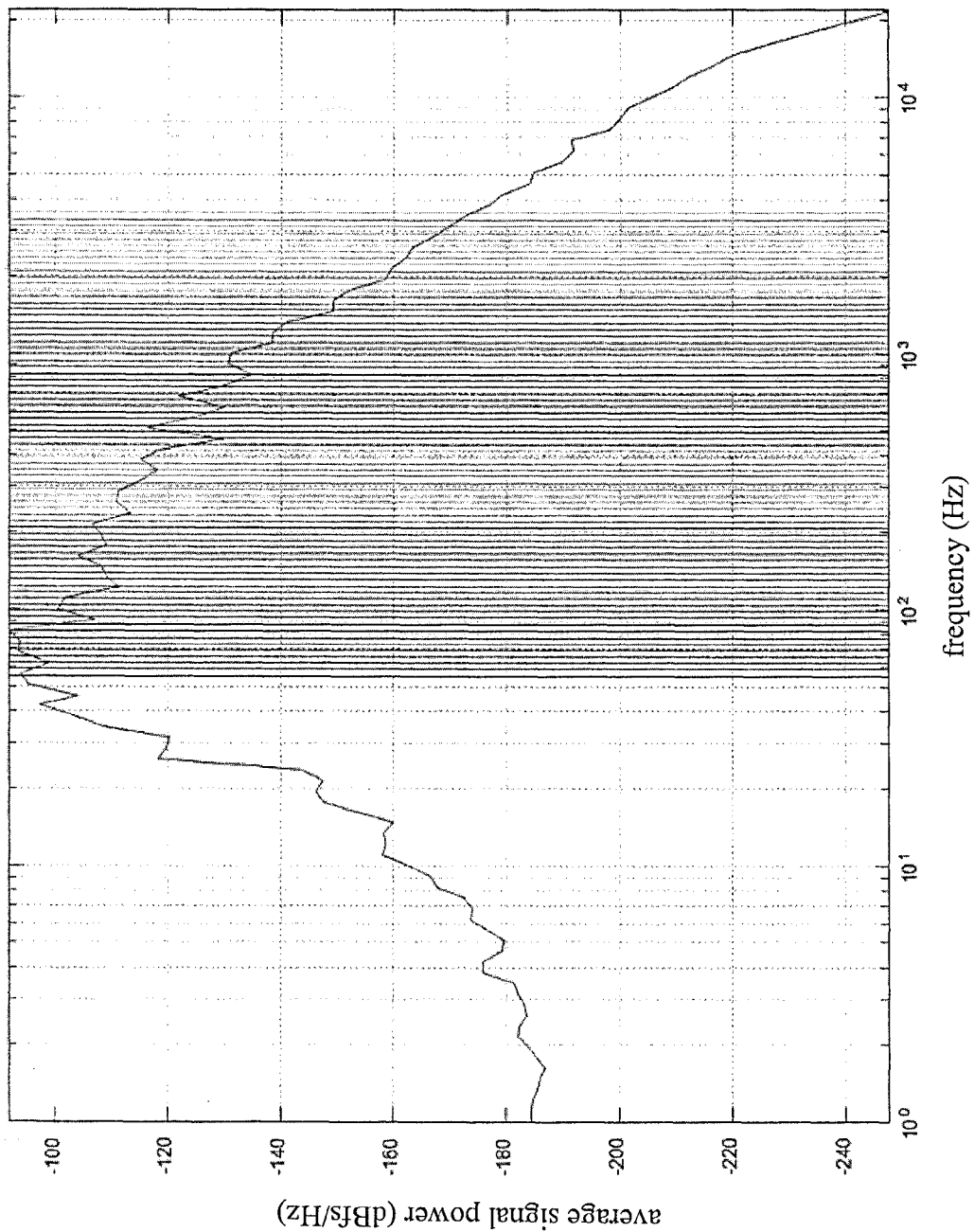
FIG. 9 is a graph of the average spectral analysis of the layered music of FIG. 8 over the entire duration of the music.

A spectral analysis was conducted of one example of layered music that was used in the EPVS study. The results of this analysis are shown in Tables 2-5, which are included at the end of this Detailed Description. Table 2 shows the results of the time-frequency spectral analysis of the layered music, while a graphical representation of this analysis is shown in FIG. 8. Table 3 shows the results of the average spectral analysis over the entire duration of the music, while a graph of the average spectral analysis is shown in FIG. 9. Table 4 shows the data for the signal envelope of the music over time, while a graph of the signal envelope over time is shown in FIG. 10. The time-frequency analysis input parameters are presented in Table 5.

All of the subjects of the EPVS study would regularly fall into an expanded state of consciousness during much of the treatment session. The subjects reported that the state they entered during the sessions was distinctly different from sleep. While it is possible to learn to be consciously aware in an expanded state, it is believed that the subjects did not remain consciously aware when they were in an expanded state during the treatment sessions. This expanded state of being is an extension of the first mechanism of action (Mechanism 1) discussed above, which involves inducing relaxation and meditation-like mind conditioning. The layered music used in the EPVS study made it easier for subjects to enter the expanded state of consciousness, thereby facilitating the first mechanism of action.

It is possible that a thermographic scan of a subject in an expanded state would show greater blood flow to the extremities. It is also possible that an EEG (electroencephalography) scan of a subject in an expanded state would show greater theta and possibly delta activity. However, while not intending to be bound by theory, it is believed that the expanded state of consciousness experienced by the subjects in this study is a state of mind, and not a brain state.

Example 1

Subject Experiencing Side Effects from Chemotherapy

One subject of the EPVS study was taking the sunitinib malate (SUTENT®) pharmaceutical to stabilize incurable renal cell carcinoma. He took the medication in four-week cycles, in which two weeks of taking the medication were followed by two weeks without the medication. This medication caused the subject to experience severe side effects. He took sunitinib malate for 4.5 years prior to beginning the EPVS study. During this 4.5-year time period his cancer remained stable (present without growth), but he had side effects with every cycle of the medication.

This subject participated in the EPVS study for five months. For the first 12 weeks of the study, which encompassed three cycles of the sunitinib malate medication, he reported an 85 to 90% reduction in his side effects from the medication. During the last eight weeks of the study, which encompassed two cycles of the sunitinib malate medication, he was virtually free of medication side effects, which is extremely unusual for patients taking sunitinib malate. Moreover, at the end of five months of participation in the EPVS study, the subject had no detectable cancer.

Example 2

Subject with Heart Disease

One subject of the EPVS study was a heart disease patient with unstable angina. After participating in the EPVS study for about two months, the subject experienced marked improvement of her angina, with a dramatic reduction in the frequency and severity of attacks. Her blood pressure and blood sugar levels also improved. It is believed that, with further EPVS treatment, she will eventually be able to discontinue most if not all of her medications.

Example 3

Subjects with Diabetes

Two subjects of the EPVS study had type 2 diabetes. The first of these subjects participated in daily treatment sessions. He experienced an improvement in diabetes symptoms within a few days of beginning the study, and felt an increase in strength after one week. After about three months of participation in the EPVS study, his blood sugar levels improved and he was able to reduce his insulin intake from 22 to 15 units per day.

The second of these subjects, who participated in three treatment sessions per week, did not experience an improvement in diabetes symptoms during the EPVS study. This subject had a different body fat distribution than the other subject with diabetes and the subject with heart disease, who both saw an improvement in blood sugar levels. Specifically, this subject had a greater proportion of abdominal fat. It is possible that during the study, the vibratory action was not sufficient to adequately penetrate the abdominal fat.

While not intending to be bound by theory, it is believed that the responses to EPVS treatment seen by the subjects with chemotherapy side effects and heart disease, and by one of the subjects with diabetes, is due to the five mechanisms of action described above.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the invention described in the specification. As one of ordinary skill in the art will readily appreciate from the disclosure of the present invention, the compositions, devices, processes, methods, and steps, presently existing or later to be developed that perform substantially the same function or achieve substantially the same result as the corresponding embodiments described herein may be utilized according to the present invention.

TABLE 2

(section 1 of 28): Time-Frequency Spectral Analysis Results

| Bin Frequency (Hz) | Bin Start Frequency (Hz) | Bin Stop Frequency (Hz) | Average Signal Power Density per Bin Width (dBfs/Hz) vs Time and Frequency Time (min): | | | | | | | | | |
|---|---|---|---|---|---|---|---|---|---|---|---|---|
| | | | 0.50 | 0.99 | 1.49 | 1.99 | 2.48 | 2.98 | 3.47 | 3.97 | 4.47 | 4.96 |
| 1.00 | 1.00 | 1.05 | −91.70 | −87.53 | −79.04 | −78.68 | −71.46 | −70.74 | −79.62 | −79.60 | −79.75 | −82.32 |
| 1.10 | 1.05 | 1.16 | −91.70 | −87.53 | −79.04 | −78.68 | −71.46 | −70.74 | −79.62 | −79.60 | −79.75 | −82.32 |
| 1.21 | 1.16 | 1.27 | −91.41 | −87.45 | −79.20 | −78.78 | −71.72 | −70.93 | −79.62 | −79.57 | −79.78 | −82.26 |
| 1.33 | 1.27 | 1.40 | −90.37 | −87.14 | −79.91 | −79.22 | −72.95 | −71.80 | −79.60 | −79.47 | −79.92 | −82.01 |
| 1.47 | 1.40 | 1.54 | −89.75 | −86.42 | −79.73 | −78.91 | −73.21 | −72.10 | −79.37 | −79.54 | −79.99 | −82.06 |
| 1.62 | 1.54 | 1.70 | −88.55 | −85.07 | −79.34 | −78.26 | −73.92 | −72.94 | −78.85 | −79.69 | −80.16 | −82.19 |
| 1.78 | 1.70 | 1.87 | −88.00 | −83.88 | −77.88 | −77.32 | −72.06 | −71.20 | −78.18 | −79.11 | −79.57 | −81.75 |
| 1.96 | 1.87 | 2.06 | −87.68 | −83.20 | −77.13 | −76.70 | −70.62 | −69.74 | −77.04 | −78.61 | −79.00 | −81.29 |
| 2.15 | 2.06 | 2.26 | −87.44 | −82.66 | −76.67 | −76.17 | −69.11 | −68.18 | −75.49 | −78.09 | −78.36 | −80.68 |
| 2.37 | 2.26 | 2.49 | −87.14 | −82.21 | −77.23 | −76.12 | −68.72 | −67.86 | −75.44 | −78.80 | −78.99 | −80.44 |
| 2.61 | 2.49 | 2.74 | −86.72 | −82.13 | −77.50 | −76.57 | −70.05 | −69.11 | −76.15 | −79.16 | −79.70 | −81.28 |
| 2.87 | 2.74 | 3.02 | −82.79 | −79.12 | −75.69 | −75.42 | −71.87 | −70.80 | −76.39 | −78.37 | −78.04 | −79.43 |
| 3.16 | 3.02 | 3.32 | −81.28 | −77.44 | −74.83 | −74.76 | −71.64 | −70.93 | −77.74 | −77.97 | −76.76 | −77.75 |
| 3.48 | 3.32 | 3.66 | −76.81 | −73.98 | −72.83 | −73.18 | −70.32 | −70.08 | −77.06 | −75.62 | −73.92 | −76.21 |
| 3.83 | 3.66 | 4.02 | −68.28 | −65.97 | −64.96 | −65.69 | −68.83 | −70.46 | −72.63 | −68.82 | −66.68 | −69.76 |
| 4.22 | 4.02 | 4.43 | −69.18 | −66.94 | −65.67 | −66.23 | −69.43 | −69.99 | −72.72 | −68.95 | −66.92 | −70.52 |
| 4.64 | 4.43 | 4.88 | −75.53 | −72.74 | −71.15 | −71.74 | −70.92 | −70.19 | −75.14 | −73.97 | −72.66 | −76.00 |
| 5.11 | 4.88 | 5.37 | −76.19 | −73.08 | −71.00 | −71.48 | −71.19 | −71.15 | −76.58 | −73.84 | −72.92 | −76.63 |
| 5.62 | 5.37 | 5.91 | −73.27 | −70.14 | −68.12 | −67.88 | −68.76 | −70.39 | −75.22 | −72.08 | −70.19 | −72.98 |
| 6.19 | 5.91 | 6.50 | −70.73 | −67.30 | −65.71 | −66.06 | −68.54 | −69.55 | −71.98 | −69.61 | −67.69 | −70.51 |
| 6.81 | 6.50 | 7.16 | −71.77 | −68.34 | −67.21 | −68.12 | −67.54 | −67.76 | −71.85 | −69.62 | −69.07 | −72.50 |
| 7.50 | 7.16 | 7.88 | −68.08 | −65.64 | −64.95 | −64.78 | −68.01 | −71.40 | −71.66 | −69.07 | −66.72 | −69.23 |
| 8.25 | 7.88 | 8.67 | −65.34 | −63.01 | −62.38 | −62.30 | −66.41 | −70.47 | −69.01 | −67.25 | −64.09 | −65.28 |
| 9.09 | 8.67 | 9.54 | −66.86 | −64.97 | −64.60 | −65.43 | −65.90 | −65.87 | −69.32 | −67.42 | −65.44 | −68.09 |
| 10.00 | 9.54 | 10.50 | −64.13 | −60.50 | −59.42 | −60.52 | −63.85 | −65.54 | −66.82 | −63.86 | −61.64 | −63.72 |
| 11.01 | 10.50 | 11.56 | −65.73 | −61.77 | −61.12 | −62.83 | −63.83 | −63.88 | −67.26 | −65.39 | −64.15 | −66.92 |
| 12.12 | 11.56 | 12.73 | −63.88 | −60.42 | −59.53 | −61.56 | −64.48 | −65.23 | −67.24 | −62.76 | −61.56 | −65.42 |
| 13.34 | 12.73 | 14.01 | −68.79 | −64.69 | −64.36 | −66.61 | −64.50 | −64.12 | −69.01 | −67.31 | −65.70 | −68.71 |
| 14.68 | 14.01 | 15.42 | −70.88 | −67.09 | −66.05 | −66.74 | −67.01 | −66.71 | −69.65 | −69.39 | −67.62 | −69.26 |
| 16.16 | 15.42 | 16.97 | −67.94 | −64.87 | −64.00 | −64.66 | −63.60 | −62.86 | −66.29 | −67.41 | −65.38 | −66.72 |
| 17.78 | 16.97 | 18.68 | −64.17 | −63.60 | −57.59 | −58.38 | −62.93 | −61.04 | −64.70 | −67.55 | −66.75 | −68.24 |
| 19.57 | 18.68 | 20.56 | −68.32 | −65.03 | −63.80 | −64.63 | −60.14 | −58.70 | −62.95 | −66.63 | −65.00 | −65.37 |
| 21.54 | 20.56 | 22.63 | −67.44 | −64.00 | −63.19 | −64.87 | −59.09 | −57.48 | −61.65 | −64.58 | −63.62 | −64.98 |
| 23.71 | 22.63 | 24.91 | −66.01 | −62.42 | −61.58 | −62.45 | −56.94 | −55.32 | −59.32 | −62.13 | −61.34 | −62.12 |
| 26.10 | 24.91 | 27.42 | −64.45 | −60.59 | −59.70 | −61.55 | −55.36 | −52.88 | −56.18 | −59.65 | −58.79 | −51.96 |
| 28.73 | 27.42 | 30.18 | −62.29 | −58.65 | −57.82 | −59.10 | −53.22 | −49.92 | −52.70 | −58.69 | −57.69 | −54.62 |
| 31.62 | 30.18 | 33.21 | −60.19 | −56.36 | −55.31 | −56.90 | −51.76 | −46.66 | −48.28 | −55.63 | −54.91 | −52.94 |
| 34.81 | 33.21 | 36.56 | −50.10 | −47.64 | −45.00 | −46.73 | −46.23 | −44.61 | −48.42 | −50.47 | −50.72 | −52.52 |
| 38.31 | 36.56 | 40.24 | −47.81 | −42.84 | −39.90 | −39.77 | −40.47 | −41.62 | −46.74 | −48.04 | −47.89 | −49.27 |
| 42.17 | 40.24 | 44.29 | −42.32 | −39.10 | −37.81 | −38.76 | −33.67 | −33.03 | −38.28 | −38.50 | −37.85 | −40.21 |
| 46.42 | 44.29 | 48.75 | −48.19 | −44.50 | −43.40 | −42.88 | −36.24 | −35.30 | −40.22 | −39.34 | −38.60 | −39.54 |
| 51.09 | 48.75 | 53.66 | −44.78 | −40.97 | −39.69 | −40.36 | −39.23 | −35.34 | −35.74 | −35.88 | −35.93 | −36.75 |
| 56.23 | 53.66 | 59.07 | −45.23 | −40.32 | −40.27 | −39.68 | −30.93 | −30.39 | −37.12 | −37.23 | −37.60 | −38.69 |
| 61.90 | 59.07 | 65.01 | −47.33 | −43.45 | −43.35 | −45.00 | −34.02 | −31.60 | −35.14 | −39.79 | −39.43 | −39.92 |
| 68.13 | 65.01 | 71.56 | −38.80 | −34.66 | −33.74 | −38.14 | −31.06 | −28.99 | −33.13 | −34.34 | −34.47 | −37.19 |
| 74.99 | 71.56 | 78.76 | −49.05 | −44.31 | −41.55 | −40.78 | −34.56 | −30.94 | −34.45 | −40.87 | −39.51 | −37.57 |
| 82.54 | 78.76 | 86.70 | −42.94 | −45.58 | −46.13 | −48.02 | −42.65 | −39.21 | −40.81 | −42.76 | −42.03 | −41.41 |
| 90.85 | 86.70 | 95.43 | −49.21 | −44.63 | −43.21 | −42.82 | −41.15 | −40.89 | −44.18 | −42.80 | −41.30 | −40.63 |
| 100.00 | 95.43 | 105.03 | −45.03 | −41.57 | −39.79 | −39.83 | −43.39 | −41.81 | −42.31 | −41.00 | −38.81 | −39.21 |
| 110.07 | 105.03 | 115.61 | −43.29 | −38.77 | −37.20 | −37.99 | −38.49 | −39.03 | −43.84 | −40.53 | −38.65 | −40.06 |
| 121.15 | 115.61 | 127.25 | −53.08 | −49.44 | −48.44 | −51.19 | −49.11 | −46.09 | −47.26 | −46.78 | −45.22 | −44.20 |
| 133.35 | 127.25 | 140.07 | −51.85 | −48.63 | −48.08 | −49.44 | −45.94 | −44.30 | −44.96 | −43.37 | −43.94 | −43.31 |
| 146.78 | 140.07 | 154.17 | −49.16 | −45.61 | −44.42 | −43.74 | −43.72 | −43.80 | −43.67 | −43.48 | −43.56 | −41.26 |

TABLE 2-continued (section 2 of 28): Time-Frequency Spectral Analysis Results

| Bin Frequency (Hz) | Bin Start Frequency (Hz) | Bin Stop Frequency (Hz) | Average Signal Power Density per Bin Width (dBfs/Hz) vs Time and Frequency Time (min): | | | | | | | | | |
|---|---|---|---|---|---|---|---|---|---|---|---|---|
| | | | 0.50 | 0.99 | 1.49 | 1.99 | 2.48 | 2.98 | 3.47 | 3.97 | 4.47 | 4.96 |
| 161.56 | 154.17 | 169.69 | −43.84 | −42.10 | −41.87 | −43.31 | −45.86 | −44.79 | −44.97 | −43.91 | −42.26 | −43.28 |
| 177.83 | 169.69 | 186.78 | −48.65 | −44.73 | −43.54 | −42.12 | −42.43 | −44.03 | −45.15 | −44.02 | −42.63 | −42.92 |
| 195.73 | 186.78 | 205.59 | −47.98 | −44.30 | −41.98 | −42.09 | −45.85 | −47.33 | −46.41 | −45.78 | −43.06 | −43.93 |
| 215.44 | 205.59 | 226.29 | −48.45 | −44.18 | −42.66 | −43.24 | −46.36 | −46.92 | −47.53 | −46.63 | −43.74 | −43.93 |
| 237.14 | 226.29 | 249.08 | −51.07 | −48.49 | −47.94 | −50.49 | −50.06 | −46.92 | −48.32 | −49.34 | −46.83 | −45.22 |
| 261.02 | 249.08 | 274.16 | −51.61 | −46.82 | −46.65 | −50.13 | −49.05 | −44.60 | −46.48 | −48.39 | −46.01 | −43.70 |
| 287.30 | 274.16 | 301.76 | −52.13 | −47.49 | −46.30 | −49.36 | −47.87 | −45.68 | −47.90 | −48.48 | −46.09 | −43.63 |
| 316.23 | 301.76 | 332.15 | −51.46 | −49.12 | −48.37 | −51.11 | −53.14 | −49.68 | −50.84 | −49.98 | −48.64 | −50.29 |
| 348.07 | 332.15 | 365.59 | −58.76 | −55.10 | −54.02 | −55.63 | −52.90 | −49.20 | −51.08 | −53.61 | −51.68 | −51.16 |
| 383.12 | 365.59 | 402.41 | −54.70 | −52.00 | −50.41 | −52.30 | −54.22 | −51.55 | −51.99 | −51.52 | −50.42 | −50.34 |
| 421.70 | 402.41 | 442.93 | −56.54 | −52.77 | −51.44 | −52.26 | −52.68 | −50.49 | −50.96 | −50.36 | −48.92 | −48.64 |
| 464.16 | 442.93 | 487.53 | −64.58 | −60.55 | −60.08 | −61.18 | −56.84 | −55.38 | −58.48 | −58.80 | −56.48 | −54.48 |
| 510.90 | 487.53 | 536.62 | −55.48 | −52.51 | −51.88 | −53.76 | −55.90 | −52.10 | −52.64 | −52.79 | −50.17 | −50.28 |
| 562.34 | 536.62 | 590.65 | −60.35 | −56.86 | −56.03 | −57.92 | −60.03 | −54.33 | −52.62 | −53.95 | −53.23 | −50.64 |
| 618.97 | 590.65 | 650.13 | −67.94 | −64.14 | −63.17 | −64.91 | −61.90 | −57.63 | −59.10 | −61.44 | −55.81 | −55.20 |
| 681.29 | 650.13 | 715.59 | −60.06 | −57.23 | −56.66 | −57.34 | −58.23 | −56.64 | −57.46 | −50.23 | −49.38 | −54.54 |
| 749.89 | 715.59 | 787.65 | −63.40 | −60.80 | −59.27 | −59.69 | −63.47 | −60.00 | −58.56 | −56.27 | −54.24 | −52.26 |
| 825.40 | 787.65 | 866.96 | −69.47 | −65.83 | −64.42 | −65.84 | −64.14 | −61.49 | −62.70 | −53.97 | −52.65 | −59.55 |
| 908.52 | 866.96 | 954.26 | −66.19 | −62.34 | −60.31 | −61.10 | −63.11 | −59.36 | −57.33 | −51.59 | −50.82 | −49.98 |
| 1000.00 | 954.26 | 1050.35 | −64.23 | −60.06 | −55.36 | −55.94 | −61.17 | −59.35 | −59.17 | −58.97 | −56.04 | −55.61 |
| 1100.69 | 1050.35 | 1156.11 | −70.08 | −64.86 | −64.39 | −66.50 | −64.75 | −62.74 | −61.51 | −60.36 | −59.21 | −54.76 |
| 1211.53 | 1156.11 | 1272.52 | −68.51 | −63.29 | −62.15 | −64.42 | −66.45 | −60.14 | −57.13 | −57.74 | −56.21 | −49.82 |
| 1333.52 | 1272.52 | 1400.66 | −70.61 | −64.03 | −62.48 | −62.25 | −64.02 | −64.92 | −62.73 | −59.59 | −59.14 | −54.16 |
| 1467.80 | 1400.66 | 1541.70 | −73.52 | −63.81 | −62.61 | −65.03 | −66.48 | −67.94 | −67.06 | −64.89 | −63.96 | −58.65 |
| 1615.60 | 1541.70 | 1696.94 | −71.62 | −65.29 | −64.46 | −67.19 | −68.84 | −65.98 | −63.77 | −62.75 | −60.70 | −61.23 |
| 1778.28 | 1696.94 | 1867.81 | −70.63 | −66.40 | −65.03 | −66.49 | −70.95 | −66.52 | −62.26 | −60.00 | −59.60 | −57.58 |
| 1957.34 | 1867.81 | 2055.89 | −70.16 | −63.43 | −62.18 | −63.70 | −67.07 | −71.30 | −68.86 | −65.06 | −64.48 | −62.87 |
| 2154.43 | 2055.89 | 2262.90 | −73.15 | −65.03 | −64.04 | −65.88 | −67.83 | −69.05 | −65.57 | −64.60 | −63.56 | −63.15 |
| 2371.37 | 2262.90 | 2490.77 | −72.04 | −67.16 | −65.25 | −62.83 | −70.95 | −68.82 | −64.38 | −62.95 | −63.61 | −63.61 |
| 2610.16 | 2490.77 | 2741.57 | −75.82 | −68.64 | −62.51 | −61.13 | −64.85 | −72.32 | −67.97 | −66.29 | −66.55 | −65.41 |
| 2872.98 | 2741.57 | 3017.63 | −77.57 | −69.10 | −65.02 | −65.59 | −70.64 | −73.09 | −70.76 | −69.13 | −68.40 | −65.94 |
| 3162.28 | 3017.63 | 3321.49 | −79.15 | −73.30 | −69.84 | −70.06 | −74.70 | −73.43 | −72.11 | −70.71 | −70.12 | −69.81 |
| 3480.70 | 3321.49 | 3655.94 | −79.28 | −72.38 | −69.67 | −69.80 | −72.38 | −74.24 | −71.40 | −68.88 | −68.52 | −68.62 |
| 3831.19 | 3655.94 | 4024.08 | −81.00 | −73.28 | −68.27 | −68.76 | −77.16 | −81.41 | −74.10 | −72.53 | −72.70 | −72.17 |
| 4216.97 | 4024.08 | 4429.28 | −81.94 | −73.95 | −69.87 | −69.82 | −73.70 | −79.07 | −74.71 | −72.51 | −72.68 | −73.31 |
| 4641.59 | 4429.28 | 4875.28 | −82.26 | −76.33 | −75.71 | −77.21 | −80.93 | −80.80 | −76.38 | −74.76 | −75.00 | −75.32 |
| 5108.97 | 4875.28 | 5366.19 | −81.49 | −76.35 | −74.42 | −74.77 | −77.88 | −81.13 | −74.42 | −71.87 | −72.74 | −76.38 |
| 5623.41 | 5366.19 | 5906.54 | −87.48 | −79.48 | −77.90 | −78.51 | −82.56 | −88.34 | −79.74 | −77.56 | −77.37 | −79.71 |
| 6189.66 | 5906.54 | 6501.29 | −91.52 | −83.55 | −77.36 | −77.41 | −83.92 | −90.80 | −84.60 | −80.61 | −80.27 | −80.60 |
| 6812.92 | 6501.29 | 7155.93 | −92.63 | −85.33 | −81.70 | −81.29 | −85.08 | −89.06 | −83.90 | −80.78 | −80.99 | −82.00 |
| 7498.94 | 7155.93 | 7876.49 | −95.89 | −88.51 | −84.93 | −85.24 | −90.34 | −93.11 | −86.80 | −83.00 | −82.72 | −83.42 |
| 8254.04 | 7876.49 | 8669.61 | −93.57 | −87.46 | −84.54 | −83.55 | −87.66 | −93.48 | −87.39 | −83.14 | −83.27 | −84.97 |
| 9085.18 | 8669.61 | 9542.59 | −95.78 | −88.16 | −84.29 | −84.62 | −89.85 | −92.83 | −87.16 | −83.89 | −84.40 | −86.94 |
| 10000.00 | 9542.59 | 10503.47 | −93.98 | −90.10 | −87.71 | −88.02 | −93.31 | −98.36 | −90.90 | −86.00 | −85.76 | −87.84 |
| 11006.94 | 10503.47 | 11561.11 | −95.13 | −91.26 | −89.45 | −90.29 | −95.22 | −99.60 | −93.31 | −87.95 | −87.66 | −89.61 |
| 12115.28 | 11561.11 | 12725.25 | −98.04 | −93.11 | −91.23 | −91.88 | −96.03 | −99.68 | −94.18 | −88.89 | −88.83 | −90.57 |
| 13335.21 | 12725.25 | 14006.60 | −97.40 | −95.20 | −92.94 | −93.68 | −100.19 | −104.48 | −98.08 | −91.72 | −91.42 | −93.06 |
| 14677.99 | 14006.60 | 15416.99 | −103.03 | −99.39 | −98.22 | −98.83 | −102.22 | −106.29 | −100.96 | −95.30 | −94.80 | −95.52 |
| 16155.98 | 15416.99 | 16969.39 | −105.89 | −101.72 | −100.23 | −100.51 | −102.90 | −106.37 | −102.67 | −98.00 | −97.42 | −98.01 |
| 17782.79 | 16969.39 | 18678.11 | −123.08 | −113.65 | −109.21 | −109.10 | −113.80 | −116.17 | −108.71 | −102.97 | −102.73 | −103.36 |
| 19573.42 | 18678.11 | 20558.88 | −123.33 | −118.44 | −117.04 | −118.03 | −118.52 | −117.79 | −115.81 | −111.30 | −110.98 | −111.30 |
| 21544.35 | 20558.88 | 22629.04 | −125.62 | −124.08 | −123.69 | −124.12 | −123.49 | −123.19 | −123.45 | −120.63 | −119.94 | −121.07 |

(section 3 of 28): Time-Frequency Spectral Analysis Results

| Bin Frequency (Hz) | Bin Start Frequency (Hz) | Bin Stop Frequency (Hz) | Average Signal Power Density per Bin Width (dBfs/Hz) vs Time and Frequency Time (min): | | | | | | | | | |
|---|---|---|---|---|---|---|---|---|---|---|---|---|
| | | | 5.46 | 5.96 | 6.45 | 6.95 | 7.44 | 7.94 | 8.44 | 8.93 | 9.43 | 9.93 |
| 1.00 | 1.00 | 1.05 | −79.39 | −81.61 | −82.54 | −71.05 | −66.90 | −72.80 | −83.31 | −81.72 | −81.21 | −81.37 |
| 1.10 | 1.05 | 1.16 | −79.39 | −81.61 | −82.54 | −71.05 | −66.90 | −72.80 | −83.31 | −81.72 | −81.21 | −81.37 |
| 1.21 | 1.16 | 1.27 | −79.40 | −81.53 | −82.48 | −71.19 | −67.19 | −72.89 | −82.71 | −81.67 | −81.11 | −81.25 |
| 1.33 | 1.27 | 1.40 | −79.44 | −81.20 | −82.26 | −71.81 | −68.65 | −73.30 | −80.85 | −81.49 | −80.69 | −80.80 |
| 1.47 | 1.40 | 1.54 | −79.68 | −81.17 | −82.28 | −71.88 | −69.10 | −73.44 | −80.76 | −81.42 | −80.54 | −80.52 |
| 1.62 | 1.54 | 1.70 | −80.31 | −81.11 | −82.34 | −72.07 | −70.38 | −73.81 | −80.55 | −81.28 | −80.21 | −79.92 |
| 1.78 | 1.70 | 1.87 | −79.94 | −80.77 | −82.09 | −70.61 | −69.07 | −74.12 | −81.92 | −81.45 | −79.97 | −79.53 |
| 1.96 | 1.87 | 2.06 | −79.57 | −80.33 | −81.66 | −69.53 | −68.01 | −73.84 | −82.62 | −81.78 | −79.94 | −78.93 |
| 2.15 | 2.06 | 2.26 | −79.12 | −79.73 | −80.98 | −68.48 | −66.85 | −72.96 | −82.21 | −82.41 | −80.15 | −78.05 |
| 2.37 | 2.26 | 2.49 | −79.23 | −79.92 | −80.74 | −68.86 | −66.45 | −72.77 | −80.03 | −81.69 | −81.04 | −78.11 |
| 2.61 | 2.49 | 2.74 | −80.01 | −80.70 | −81.09 | −69.75 | −67.26 | −72.35 | −78.67 | −80.76 | −80.44 | −78.60 |

TABLE 2-continued

| | | | | | | | | | | | |
|---|---|---|---|---|---|---|---|---|---|---|---|
| 2.87 | 2.74 | 3.02 | −79.32 | −80.74 | −81.22 | −69.52 | −68.06 | −73.28 | −79.14 | −80.92 | −80.51 | −78.99 |
| 3.16 | 3.02 | 3.32 | −78.40 | −79.83 | −80.85 | −69.16 | −66.91 | −73.82 | −79.53 | −81.21 | −80.90 | −80.69 |
| 3.48 | 3.32 | 3.66 | −79.31 | −79.95 | −80.22 | −69.73 | −66.75 | −72.13 | −78.91 | −80.92 | −79.77 | −80.42 |
| 3.83 | 3.66 | 4.02 | −79.39 | −79.90 | −79.41 | −71.00 | −67.53 | −71.51 | −77.88 | −79.73 | −78.95 | −78.18 |
| 4.22 | 4.02 | 4.43 | −78.52 | −80.07 | −80.43 | −70.49 | −68.90 | −73.49 | −79.22 | −79.14 | −78.88 | −77.62 |
| 4.64 | 4.43 | 4.88 | −78.65 | −80.90 | −82.06 | −70.78 | −68.72 | −73.07 | −79.68 | −80.37 | −79.26 | −79.40 |
| 5.11 | 4.88 | 5.37 | −78.95 | −80.57 | −82.89 | −73.18 | −69.72 | −72.11 | −79.59 | −80.18 | −79.89 | −79.37 |
| 5.62 | 5.37 | 5.91 | −78.57 | −80.74 | −82.03 | −71.43 | −68.19 | −72.63 | −79.61 | −79.30 | −79.76 | −77.69 |
| 6.19 | 5.91 | 6.50 | −77.30 | −79.53 | −82.30 | −70.89 | −68.29 | −72.38 | −78.74 | −77.72 | −78.31 | −76.61 |
| 6.81 | 6.50 | 7.16 | −76.47 | −78.98 | −81.40 | −69.11 | −66.92 | −72.59 | −78.14 | −75.36 | −76.27 | −75.69 |
| 7.50 | 7.16 | 7.88 | −78.83 | −82.09 | −81.09 | −72.69 | −69.80 | −73.55 | −78.51 | −78.29 | −78.64 | −76.83 |
| 8.25 | 7.88 | 8.67 | −78.16 | −80.59 | −81.64 | −72.76 | −68.78 | −71.32 | −76.43 | −75.85 | −76.61 | −73.76 |
| 9.09 | 8.67 | 9.54 | −73.74 | −77.49 | −78.99 | −65.92 | −64.71 | −70.61 | −71.79 | −71.11 | −74.03 | −70.26 |
| 10.00 | 9.54 | 10.50 | −72.84 | −76.40 | −80.19 | −67.72 | −64.02 | −68.70 | −74.40 | −72.54 | −74.23 | −73.51 |
| 11.01 | 10.50 | 11.56 | −71.24 | −75.22 | −77.49 | −64.31 | −62.95 | −68.41 | −73.03 | −70.62 | −73.11 | −73.39 |
| 12.12 | 11.56 | 12.73 | −72.14 | −74.98 | −76.75 | −66.46 | −64.61 | −69.92 | −70.52 | −69.61 | −72.64 | −67.67 |
| 13.34 | 12.73 | 14.01 | −70.47 | −73.99 | −76.31 | −64.81 | −63.13 | −67.62 | −71.81 | −69.20 | −71.88 | −72.66 |
| 14.68 | 14.01 | 15.42 | −72.22 | −74.42 | −76.77 | −67.25 | −65.64 | −69.72 | −72.61 | −70.92 | −73.61 | −71.94 |
| 16.16 | 15.42 | 16.97 | −69.55 | −72.60 | −75.12 | −64.12 | −62.77 | −67.31 | −69.38 | −67.24 | −69.69 | −66.28 |
| 17.78 | 16.97 | 18.68 | −67.77 | −70.63 | −72.17 | −62.69 | −61.10 | −65.21 | −69.01 | −66.34 | −67.93 | −67.85 |
| 19.57 | 18.68 | 20.56 | −64.73 | −66.73 | −69.34 | −60.70 | −58.77 | −62.80 | −66.51 | −62.96 | −63.80 | −63.44 |
| 21.54 | 20.56 | 22.63 | −63.56 | −65.67 | −68.37 | −58.97 | −56.99 | −60.79 | −64.60 | −61.51 | −62.04 | −62.53 |
| 23.71 | 22.63 | 24.91 | −61.32 | −63.16 | −62.46 | −55.35 | −53.03 | −55.44 | −61.62 | −59.00 | −58.48 | −58.97 |
| 26.10 | 24.91 | 27.42 | −58.59 | −60.21 | −60.45 | −53.82 | −51.71 | −54.72 | −60.43 | −56.51 | −55.10 | −55.02 |
| 28.73 | 27.42 | 30.18 | −56.52 | −58.86 | −58.98 | −51.98 | −49.66 | −52.02 | −58.08 | −52.94 | −52.07 | −53.14 |
| 31.62 | 30.18 | 33.21 | −54.71 | −56.47 | −48.21 | −44.57 | −43.43 | −44.63 | −51.21 | −51.66 | −48.31 | −47.40 |
| 34.81 | 33.21 | 36.56 | −51.53 | −54.06 | −43.93 | −39.22 | −38.51 | −41.13 | −47.31 | −39.44 | −37.26 | −38.17 |
| 38.31 | 36.56 | 40.24 | −48.17 | −50.55 | −42.71 | −38.29 | −37.74 | −40.49 | −45.83 | −39.46 | −35.58 | −35.25 |
| 42.17 | 40.24 | 44.29 | −39.26 | −39.66 | −38.99 | −33.91 | −32.12 | −35.90 | −40.32 | −38.30 | −39.98 | −39.70 |
| 46.42 | 44.29 | 48.75 | −37.09 | −37.12 | −37.96 | −34.89 | −34.01 | −37.01 | −41.44 | −41.39 | −43.07 | −42.99 |
| 51.09 | 48.75 | 53.66 | −35.15 | −35.03 | −33.82 | −31.05 | −29.37 | −30.79 | −36.37 | −39.50 | −40.19 | −36.87 |
| 56.23 | 53.66 | 59.07 | −36.13 | −37.24 | −36.47 | −30.43 | −28.27 | −33.21 | −36.92 | −34.93 | −36.80 | −38.14 |
| 61.90 | 59.07 | 65.01 | −37.60 | −39.60 | −40.68 | −33.93 | −31.49 | −34.32 | −40.35 | −37.49 | −38.84 | −42.04 |
| 68.13 | 65.01 | 71.56 | −35.61 | −38.58 | −39.64 | −31.08 | −28.85 | −31.98 | −37.99 | −34.39 | −35.77 | −40.42 |
| 74.99 | 71.56 | 78.76 | −37.42 | −41.04 | −39.43 | −33.07 | −30.67 | −33.13 | −40.25 | −36.43 | −36.45 | −38.69 |
| 82.54 | 78.76 | 86.70 | −41.15 | −46.31 | −42.84 | −37.81 | −36.93 | −38.63 | −38.44 | −39.36 | −42.45 | −35.72 |
| 90.85 | 86.70 | 95.43 | −41.31 | −47.64 | −44.12 | −38.65 | −37.87 | −41.41 | −46.01 | −44.62 | −47.33 | −48.02 |
| 100.00 | 95.43 | 105.03 | −40.07 | −42.26 | −41.54 | −39.19 | −38.38 | −39.93 | −43.32 | −43.98 | −47.59 | −42.73 |
| 110.07 | 105.03 | 115.61 | −41.07 | −42.85 | −45.25 | −39.10 | −37.42 | −41.33 | −43.70 | −42.77 | −46.69 | −48.56 |
| 121.15 | 115.61 | 127.25 | −43.70 | −45.97 | −47.53 | −44.46 | −42.60 | −42.06 | −43.67 | −46.81 | −49.66 | −49.25 |
| 133.35 | 127.25 | 140.07 | −41.64 | −41.56 | −44.04 | −43.36 | −42.06 | −41.90 | −42.89 | −44.03 | −45.02 | −46.33 |
| 146.78 | 140.07 | 154.17 | −40.10 | −40.54 | −43.87 | −45.05 | −43.89 | −43.30 | −44.16 | −45.08 | −44.61 | −43.76 |

(section 4 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | |
|---|---|---|---|---|---|---|---|---|---|---|---|
| (Hz) | (Hz) | (Hz) | 5.46 | 5.96 | 6.45 | 6.95 | 7.44 | 7.94 | 8.44 | 8.93 | 9.43 | 9.93 |
| 161.56 | 154.17 | 169.69 | −44.07 | −44.38 | −45.33 | −43.57 | −43.09 | −44.18 | −45.35 | −47.17 | −49.45 | −45.74 |
| 177.83 | 169.69 | 186.78 | −40.58 | −40.25 | −45.22 | −43.13 | −41.76 | −43.59 | −45.94 | −46.15 | −49.20 | −50.64 |
| 195.73 | 186.78 | 205.59 | −47.45 | −47.71 | −47.54 | −45.53 | −45.00 | −45.41 | −46.15 | −48.81 | −51.29 | −47.85 |
| 215.44 | 205.59 | 226.29 | −46.04 | −47.85 | −49.17 | −45.90 | −43.76 | −44.71 | −45.88 | −46.04 | −47.50 | −49.75 |
| 237.14 | 226.29 | 249.08 | −45.27 | −47.80 | −49.63 | −46.60 | −43.24 | −41.23 | −42.26 | −46.86 | −49.19 | −49.05 |
| 261.02 | 249.08 | 274.16 | −43.47 | −45.99 | −47.77 | −45.30 | −40.94 | −39.00 | −40.51 | −44.42 | −45.75 | −45.69 |
| 287.30 | 274.16 | 301.76 | −43.98 | −47.51 | −48.25 | −42.78 | −38.85 | −40.44 | −44.68 | −45.90 | −46.22 |
| 316.23 | 301.76 | 332.15 | −50.54 | −50.11 | −49.02 | −47.94 | −47.09 | −46.45 | −47.74 | −48.10 | −47.83 | −50.33 |
| 348.07 | 332.15 | 365.59 | −49.60 | −49.83 | −51.18 | −50.01 | −47.87 | −47.00 | −49.18 | −48.76 | −48.51 | −52.00 |
| 383.12 | 365.59 | 402.41 | −50.91 | −51.64 | −50.60 | −49.12 | −46.63 | −45.92 | −47.99 | −49.25 | −49.15 | −50.62 |
| 421.70 | 402.41 | 442.93 | −49.75 | −53.28 | −52.66 | −48.24 | −46.80 | −47.47 | −49.14 | −48.96 | −49.03 | −51.42 |
| 464.16 | 442.93 | 487.53 | −54.67 | −57.56 | −59.19 | −55.03 | −52.57 | −51.99 | −53.26 | −53.17 | −53.55 | −57.04 |
| 510.90 | 487.53 | 536.62 | −51.91 | −52.99 | −51.50 | −50.45 | −48.30 | −46.52 | −48.20 | −51.45 | −50.23 | −51.23 |
| 562.34 | 536.62 | 590.65 | −52.21 | −55.80 | −53.43 | −50.77 | −50.03 | −48.92 | −51.37 | −55.21 | −52.85 | −52.82 |
| 618.97 | 590.65 | 650.13 | −58.46 | −58.01 | −58.03 | −58.54 | −54.13 | −53.60 | −56.50 | −57.09 | −55.42 | −57.19 |
| 681.29 | 650.13 | 715.59 | −55.77 | −56.66 | −53.24 | −50.66 | −47.91 | −48.03 | −53.72 | −55.59 | −54.46 | −56.10 |
| 749.89 | 715.59 | 787.65 | −52.92 | −57.42 | −58.82 | −55.57 | −54.18 | −54.87 | −56.97 | −60.20 | −59.92 | −60.05 |
| 825.40 | 787.65 | 866.96 | −59.72 | −59.82 | −58.85 | −54.42 | −50.95 | −53.25 | −58.34 | −63.08 | −61.77 | −61.52 |
| 908.52 | 866.96 | 954.26 | −51.30 | −56.16 | −55.50 | −51.88 | −50.99 | −54.32 | −58.35 | −60.19 | −58.43 | −59.58 |
| 1000.00 | 954.26 | 1050.35 | −57.39 | −54.32 | −52.09 | −52.43 | −53.46 | −50.79 | −60.31 | −57.13 | −58.60 |
| 1100.69 | 1050.35 | 1156.11 | −54.77 | −53.41 | −52.49 | −53.07 | −53.91 | −55.96 | −58.08 | −63.78 | −63.67 | −64.72 |
| 1211.53 | 1156.11 | 1272.52 | −50.45 | −56.19 | −55.19 | −52.52 | −55.55 | −55.69 | −57.75 | −61.75 | −59.34 | −61.02 |
| 1333.52 | 1272.52 | 1400.66 | −54.75 | −58.43 | −57.61 | −55.40 | −55.37 | −55.64 | −57.02 | −62.15 | −60.37 | −63.12 |
| 1467.80 | 1400.66 | 1541.70 | −58.50 | −63.17 | −62.31 | −59.20 | −59.32 | −61.07 | −62.53 | −67.06 | −65.49 | −66.88 |
| 1615.60 | 1541.70 | 1696.94 | −63.15 | −61.40 | −58.36 | −57.93 | −58.65 | −57.76 | −59.56 | −66.78 | −63.83 | −65.42 |
| 1778.28 | 1696.94 | 1867.81 | −58.70 | −66.05 | −61.14 | −58.62 | −59.49 | −61.40 | −64.37 | −69.04 | −67.66 | −67.85 |
| 1957.34 | 1867.81 | 2055.89 | −63.65 | −67.52 | −65.79 | −63.52 | −62.60 | −63.05 | −66.32 | −70.72 | −69.65 | −70.00 |
| 2154.43 | 2055.89 | 2262.90 | −64.68 | −69.03 | −65.97 | −61.85 | −61.36 | −62.87 | −65.78 | −69.48 | −68.92 | −69.71 |
| 2371.37 | 2262.90 | 2490.77 | −65.08 | −68.75 | −65.68 | −62.63 | −61.18 | −62.15 | −66.60 | −70.79 | −70.13 | −70.12 |

TABLE 2-continued

| | | | | | | | | | | | |
|---|---|---|---|---|---|---|---|---|---|---|---|
| 2610.16 | 2490.77 | 2741.57 | −66.59 | −71.16 | −67.61 | −63.52 | −62.28 | −64.21 | −68.52 | −71.27 | −69.17 | −68.77 |
| 2872.98 | 2741.57 | 3017.63 | −66.67 | −71.54 | −68.23 | −65.31 | −64.51 | −65.43 | −69.20 | −72.09 | −71.21 | −69.56 |
| 3162.28 | 3017.63 | 3321.49 | −70.55 | −72.85 | −68.83 | −65.89 | −65.30 | −65.56 | −68.52 | −72.25 | −72.18 | −71.37 |
| 3480.70 | 3321.49 | 3655.94 | −69.78 | −74.13 | −71.45 | −67.87 | −66.89 | −68.18 | −72.25 | −74.15 | −72.57 | −71.57 |
| 3831.19 | 3655.94 | 4024.08 | −73.25 | −78.47 | −74.86 | −70.56 | −69.49 | −70.93 | −74.50 | −75.39 | −74.42 | −72.06 |
| 4216.97 | 4024.08 | 4429.28 | −75.13 | −77.88 | −74.57 | −70.71 | −69.42 | −70.78 | −74.89 | −75.58 | −74.39 | −72.59 |
| 4641.59 | 4429.28 | 4875.28 | −76.24 | −79.92 | −77.17 | −72.82 | −71.28 | −72.66 | −77.11 | −78.28 | −77.37 | −75.49 |
| 5108.97 | 4875.28 | 5366.19 | −77.96 | −81.25 | −77.74 | −73.26 | −72.01 | −73.71 | −79.10 | −80.48 | −79.90 | −76.41 |
| 5623.41 | 5366.19 | 5906.54 | −80.78 | −83.42 | −79.23 | −75.30 | −74.11 | −75.32 | −79.93 | −81.35 | −80.70 | −77.13 |
| 6189.66 | 5906.54 | 6501.29 | −81.13 | −84.40 | −79.83 | −76.23 | −74.75 | −75.62 | −80.48 | −80.94 | −78.83 | −77.80 |
| 6812.92 | 6501.29 | 7155.93 | −82.72 | −86.26 | −82.40 | −78.38 | −76.86 | −77.77 | −82.12 | −81.31 | −78.51 | −75.38 |
| 7498.94 | 7155.93 | 7876.49 | −84.13 | −87.29 | −82.91 | −79.24 | −77.98 | −79.02 | −83.45 | −83.30 | −81.01 | −78.48 |
| 8254.04 | 7876.49 | 8669.61 | −85.86 | −89.17 | −83.13 | −78.90 | −77.96 | −79.66 | −84.76 | −85.19 | −82.39 | −80.75 |
| 9085.18 | 8669.61 | 9542.59 | −87.95 | −90.71 | −84.37 | −80.62 | −79.68 | −81.06 | −86.11 | −86.05 | −81.53 | −80.57 |
| 10000.00 | 9542.59 | 10503.47 | −88.74 | −91.55 | −87.69 | −83.87 | −82.87 | −84.06 | −87.87 | −87.04 | −84.34 | −82.91 |
| 11006.94 | 10503.47 | 11561.11 | −90.45 | −93.69 | −89.47 | −85.67 | −84.60 | −85.79 | −89.72 | −89.44 | −86.45 | −85.54 |
| 12115.28 | 11561.11 | 12725.25 | −90.92 | −94.07 | −89.47 | −85.49 | −84.70 | −86.18 | −90.37 | −90.05 | −87.44 | −87.20 |
| 13335.21 | 12725.25 | 14006.60 | −93.56 | −97.17 | −93.49 | −89.72 | −88.68 | −90.05 | −93.70 | −93.20 | −90.51 | −90.32 |
| 14677.99 | 14006.60 | 15416.99 | −96.03 | −99.95 | −96.49 | −92.68 | −91.43 | −92.76 | −97.01 | −97.04 | −94.54 | −93.23 |
| 16155.98 | 15416.99 | 16969.39 | −98.91 | −102.63 | −98.58 | −95.06 | −94.26 | −95.77 | −100.45 | −100.87 | −98.52 | −97.84 |
| 17782.79 | 16969.39 | 18678.11 | −103.61 | −106.72 | −102.77 | −99.31 | −98.81 | −100.33 | −106.03 | −108.31 | −104.64 | −103.79 |
| 19573.42 | 18678.11 | 20558.88 | −111.67 | −113.49 | −110.28 | −107.49 | −106.69 | −107.11 | −110.80 | −114.49 | −110.44 | −109.36 |
| 21544.35 | 20558.88 | 22629.04 | −121.03 | −122.01 | −120.28 | −117.60 | −116.87 | −118.26 | −121.45 | −123.06 | −121.68 | −121.50 |

(section 5 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | | |
|---|---|---|---|---|---|---|---|---|---|---|---|
| (Hz) | (Hz) | (Hz) | 10.42 | 10.92 | 11.41 | 11.91 | 12.41 | 12.90 | 13.40 | 13.90 | 14.39 | 14.89 |
| 1.00 | 1.00 | 1.05 | −72.63 | −70.59 | −74.23 | −81.35 | −79.60 | −78.27 | −78.33 | −79.82 | −83.08 | −94.82 |
| 1.10 | 1.05 | 1.16 | −72.63 | −70.59 | −74.23 | −81.35 | −79.60 | −78.27 | −78.33 | −79.82 | −83.08 | −94.82 |
| 1.21 | 1.16 | 1.27 | −72.75 | −70.63 | −74.12 | −81.39 | −79.65 | −78.32 | −78.15 | −79.81 | −82.88 | −94.58 |
| 1.33 | 1.27 | 1.40 | −73.28 | −70.80 | −73.70 | −81.57 | −79.87 | −78.50 | −77.46 | −79.76 | −82.12 | −93.71 |
| 1.47 | 1.40 | 1.54 | −73.29 | −70.91 | −73.70 | −81.80 | −79.95 | −78.37 | −77.62 | −79.49 | −81.99 | −93.49 |
| 1.62 | 1.54 | 1.70 | −73.32 | −71.21 | −73.70 | −82.39 | −80.14 | −78.07 | −78.00 | −78.90 | −81.69 | −93.01 |
| 1.78 | 1.70 | 1.87 | −72.62 | −70.49 | −73.58 | −82.33 | −80.68 | −78.50 | −78.27 | −79.13 | −82.30 | −93.21 |
| 1.96 | 1.87 | 2.06 | −71.62 | −69.69 | −73.56 | −82.02 | −80.90 | −78.75 | −77.93 | −79.34 | −82.78 | −93.42 |
| 2.15 | 2.06 | 2.26 | −70.33 | −68.74 | −73.67 | −81.40 | −80.80 | −78.79 | −76.97 | −79.58 | −83.23 | −93.73 |
| 2.37 | 2.26 | 2.49 | −70.77 | −69.71 | −74.55 | −81.38 | −80.55 | −78.03 | −76.95 | −79.37 | −83.79 | −93.55 |
| 2.61 | 2.49 | 2.74 | −72.78 | −71.47 | −74.64 | −80.97 | −78.53 | −77.61 | −77.97 | −79.77 | −82.82 | −92.84 |
| 2.87 | 2.74 | 3.02 | −72.47 | −70.41 | −73.34 | −79.83 | −78.19 | −77.10 | −78.43 | −79.39 | −82.34 | −92.91 |
| 3.16 | 3.02 | 3.32 | −71.93 | −69.96 | −73.08 | −79.23 | −77.34 | −76.56 | −78.03 | −78.87 | −82.62 | −93.96 |
| 3.48 | 3.32 | 3.66 | −71.41 | −69.77 | −73.92 | −79.12 | −75.95 | −75.57 | −77.57 | −79.04 | −82.67 | −93.35 |
| 3.83 | 3.66 | 4.02 | −71.38 | −69.91 | −74.29 | −78.90 | −74.60 | −74.44 | −76.26 | −77.77 | −80.70 | −91.98 |
| 4.22 | 4.02 | 4.43 | −70.31 | −68.57 | −71.84 | −77.41 | −75.61 | −74.68 | −74.90 | −76.48 | −79.58 | −90.83 |
| 4.64 | 4.43 | 4.88 | −70.49 | −67.87 | −70.69 | −78.64 | −77.04 | −75.45 | −75.75 | −77.81 | −81.09 | −92.41 |
| 5.11 | 4.88 | 5.37 | −72.25 | −69.88 | −72.30 | −80.00 | −78.79 | −76.50 | −75.25 | −76.59 | −80.83 | −93.32 |
| 5.62 | 5.37 | 5.91 | −72.22 | −69.69 | −71.68 | −79.29 | −77.68 | −75.57 | −74.87 | −76.06 | −80.72 | −92.70 |
| 6.19 | 5.91 | 6.50 | −72.01 | −69.70 | −71.93 | −78.63 | −76.90 | −75.03 | −75.37 | −77.86 | −80.60 | −88.80 |
| 6.81 | 6.50 | 7.16 | −70.35 | −69.20 | −72.83 | −78.46 | −76.66 | −75.31 | −75.74 | −77.70 | −81.11 | −89.08 |
| 7.50 | 7.16 | 7.88 | −68.70 | −67.01 | −70.72 | −76.38 | −76.15 | −74.50 | −74.40 | −76.59 | −81.72 | −91.22 |
| 8.25 | 7.88 | 8.67 | −67.52 | −65.93 | −69.19 | −75.11 | −75.33 | −72.79 | −72.43 | −74.68 | −79.94 | −88.71 |
| 9.09 | 8.67 | 9.54 | −65.45 | −63.99 | −66.51 | −72.47 | −72.91 | −71.65 | −72.77 | −75.49 | −79.50 | −87.85 |
| 10.00 | 9.54 | 10.50 | −68.27 | −66.59 | −68.73 | −74.61 | −74.84 | −74.02 | −73.67 | −75.72 | −80.28 | −87.72 |
| 11.01 | 10.50 | 11.56 | −68.57 | −67.25 | −69.84 | −74.67 | −74.08 | −72.63 | −72.57 | −74.46 | −78.50 | −87.09 |
| 12.12 | 11.56 | 12.73 | −61.64 | −60.65 | −63.86 | −69.88 | −67.49 | −67.00 | −66.90 | −68.24 | −72.70 | −81.41 |
| 13.34 | 12.73 | 14.01 | −67.38 | −64.92 | −66.52 | −71.44 | −70.56 | −69.22 | −70.49 | −72.07 | −76.47 | −84.55 |
| 14.68 | 14.01 | 15.42 | −66.66 | −64.68 | −66.86 | −71.88 | −69.96 | −68.54 | −69.77 | −72.52 | −75.99 | −80.72 |
| 16.16 | 15.42 | 16.97 | −60.45 | −59.39 | −62.41 | −67.78 | −65.14 | −64.60 | −64.90 | −66.00 | −69.89 | −78.60 |
| 17.78 | 16.97 | 18.68 | −64.32 | −62.74 | −64.41 | −68.42 | −66.93 | −65.39 | −66.21 | −66.63 | −69.69 | −79.33 |
| 19.57 | 18.68 | 20.56 | −59.57 | −58.22 | −60.62 | −65.46 | −63.41 | −62.32 | −61.99 | −62.35 | −66.29 | −76.15 |
| 21.54 | 20.56 | 22.63 | −60.31 | −59.46 | −61.30 | −64.81 | −62.51 | −60.50 | −60.26 | −59.83 | −62.56 | −68.55 |
| 23.71 | 22.63 | 24.91 | −56.49 | −55.69 | −58.25 | −62.46 | −59.89 | −58.12 | −57.37 | −57.03 | −60.28 | −74.41 |
| 26.10 | 24.91 | 27.42 | −54.27 | −54.67 | −57.14 | −60.19 | −57.53 | −55.57 | −54.34 | −52.99 | −56.06 | −73.89 |
| 28.73 | 27.42 | 30.18 | −52.41 | −52.72 | −55.32 | −57.19 | −55.33 | −54.01 | −52.52 | −51.51 | −54.96 | −72.03 |
| 31.62 | 30.18 | 33.21 | −47.22 | −48.21 | −50.71 | −53.77 | −50.86 | −48.11 | −46.34 | −44.90 | −47.88 | −69.88 |
| 34.81 | 33.21 | 36.56 | −38.72 | −40.31 | −42.91 | −42.84 | −40.52 | −38.72 | −36.85 | −35.08 | −38.06 | −66.93 |
| 38.31 | 36.56 | 40.24 | −35.65 | −36.81 | −39.61 | −41.67 | −38.09 | −35.34 | −33.83 | −32.32 | −35.30 | −62.21 |
| 42.17 | 40.24 | 44.29 | −35.45 | −34.30 | −37.10 | −43.34 | −39.47 | −38.41 | −37.92 | −38.59 | −42.29 | −54.27 |
| 46.42 | 44.29 | 48.75 | −40.91 | −40.98 | −43.05 | −45.67 | −44.76 | −42.84 | −42.18 | −43.21 | −47.29 | −63.71 |
| 51.09 | 48.75 | 53.66 | −36.86 | −40.29 | −39.37 | −38.15 | −39.60 | −39.82 | −38.12 | −40.76 | −48.99 | −60.70 |
| 56.23 | 53.66 | 59.07 | −38.36 | −41.34 | −41.32 | −40.44 | −40.25 | −39.06 | −38.41 | −40.77 | −46.08 | −50.13 |
| 61.90 | 59.07 | 65.01 | −41.40 | −41.86 | −42.96 | −44.56 | −43.00 | −41.41 | −41.47 | −42.63 | −45.29 | −48.61 |
| 68.13 | 65.01 | 71.56 | −39.40 | −39.03 | −40.36 | −42.92 | −41.62 | −39.33 | −39.23 | −39.77 | −43.22 | −50.80 |
| 74.99 | 71.56 | 78.76 | −34.44 | −33.04 | −35.20 | −38.67 | −37.50 | −36.35 | −37.35 | −37.05 | −39.40 | −40.79 |
| 82.54 | 78.76 | 86.70 | −29.94 | −27.93 | −29.44 | −33.79 | −32.60 | −31.50 | −32.73 | −34.63 | −38.20 | −38.78 |
| 90.85 | 86.70 | 95.43 | −45.98 | −45.19 | −47.21 | −48.68 | −46.96 | −46.54 | −47.02 | −50.00 | −50.59 | −46.14 |
| 100.00 | 95.43 | 105.03 | −36.35 | −34.22 | −36.61 | −41.07 | −39.57 | −39.28 | −40.87 | −42.49 | −44.74 | −45.80 |

TABLE 2-continued

| | | | | | | | | | | | |
|---|---|---|---|---|---|---|---|---|---|---|---|
| 110.07 | 105.03 | 115.61 | −43.35 | −41.82 | −43.91 | −46.54 | −44.49 | −44.68 | −45.71 | −48.68 | −50.65 | −49.84 |
| 121.15 | 115.61 | 127.25 | −46.14 | −44.86 | −46.50 | −49.11 | −47.81 | −47.31 | −46.83 | −45.92 | −46.79 | −49.19 |
| 133.35 | 127.25 | 140.07 | −46.11 | −45.61 | −47.15 | −49.78 | −47.74 | −45.86 | −45.04 | −43.87 | −44.19 | −44.36 |
| 146.78 | 140.07 | 154.17 | −42.90 | −42.67 | −45.04 | −48.30 | −47.48 | −46.54 | −44.91 | −43.71 | −45.71 | −47.70 |

(section 6 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | | |
|---|---|---|---|---|---|---|---|---|---|---|---|---|
| (Hz) | (Hz) | (Hz) | 10.42 | 10.92 | 11.41 | 11.91 | 12.41 | 12.90 | 13.40 | 13.90 | 14.39 | 14.89 |
| 161.56 | 154.17 | 169.69 | −40.93 | −39.38 | −40.89 | −45.94 | −44.02 | −42.58 | −43.02 | −43.68 | −46.53 | −51.72 |
| 177.83 | 169.69 | 186.78 | −50.56 | −50.73 | −53.17 | −54.32 | −52.19 | −51.11 | −49.48 | −48.46 | −50.00 | −50.86 |
| 195.73 | 186.78 | 205.59 | −42.22 | −40.31 | −42.77 | −47.11 | −45.83 | −44.79 | −44.35 | −45.15 | −48.54 | −51.48 |
| 215.44 | 205.59 | 226.29 | −48.20 | −47.22 | −48.99 | −50.01 | −48.29 | −49.62 | −49.13 | −49.31 | −50.77 | −49.68 |
| 237.14 | 226.29 | 249.08 | −46.19 | −44.81 | −48.76 | −47.16 | −45.99 | −44.75 | −44.46 | −46.48 | −47.80 |
| 261.02 | 249.08 | 274.16 | −46.47 | −46.50 | −48.17 | −49.31 | −48.10 | −48.65 | −46.20 | −45.10 | −46.68 | −47.31 |
| 287.30 | 274.16 | 301.76 | −46.08 | −45.68 | −47.90 | −50.53 | −49.31 | −47.48 | −45.77 | −45.77 | −45.86 | −47.44 |
| 316.23 | 301.76 | 332.15 | −50.07 | −49.18 | −51.05 | −53.45 | −51.42 | −50.05 | −49.72 | −49.06 | −50.80 | −56.47 |
| 348.07 | 332.15 | 365.59 | −52.98 | −53.54 | −55.64 | −58.89 | −57.68 | −54.91 | −51.54 | −52.60 | −55.35 | −54.93 |
| 383.12 | 365.59 | 402.41 | −50.08 | −49.06 | −50.84 | −55.69 | −54.68 | −52.25 | −48.59 | −49.73 | −53.86 | −55.53 |
| 421.70 | 402.41 | 442.93 | −53.23 | −53.26 | −55.77 | −58.20 | −57.30 | −55.31 | −53.85 | −54.21 | −56.21 | −56.94 |
| 464.16 | 442.93 | 487.53 | −58.18 | −57.73 | −60.86 | −63.59 | −62.43 | −58.33 | −57.25 | −57.75 | −58.66 | −60.34 |
| 510.90 | 487.53 | 536.62 | −53.42 | −52.46 | −54.34 | −55.27 | −54.34 | −52.58 | −50.90 | −51.88 | −53.84 | −54.08 |
| 562.34 | 536.62 | 590.65 | −54.84 | −54.68 | −57.04 | −60.74 | −58.51 | −55.62 | −54.10 | −55.06 | −54.35 | −53.21 |
| 618.97 | 590.65 | 650.13 | −57.26 | −55.74 | −58.30 | −62.80 | −60.75 | −54.01 | −52.74 | −56.16 | −58.72 | −58.40 |
| 681.29 | 650.13 | 715.59 | −54.48 | −52.28 | −54.39 | −60.44 | −57.44 | −50.57 | −48.79 | −52.56 | −57.34 | −53.48 |
| 749.89 | 715.59 | 787.65 | −57.98 | −55.97 | −57.93 | −62.51 | −59.56 | −54.88 | −52.55 | −54.59 | −59.14 | −59.59 |
| 825.40 | 787.65 | 866.96 | −59.13 | −57.12 | −59.54 | −63.20 | −59.86 | −55.06 | −53.76 | −56.92 | −60.66 | −59.26 |
| 908.52 | 866.96 | 954.26 | −57.36 | −55.70 | −59.57 | −65.05 | −60.57 | −53.26 | −53.24 | −59.42 | −62.36 | −59.44 |
| 1000.00 | 954.26 | 1050.35 | −60.32 | −58.28 | −59.92 | −61.33 | −60.93 | −56.64 | −55.71 | −58.23 | −60.91 | −60.98 |
| 1100.69 | 1050.35 | 1156.11 | −63.68 | −62.02 | −64.30 | −67.07 | −65.55 | −59.88 | −59.59 | −62.28 | −63.46 | −64.19 |
| 1211.53 | 1156.11 | 1272.52 | −60.99 | −59.14 | −61.64 | −65.13 | −63.12 | −57.50 | −56.32 | −59.49 | −61.01 | −60.87 |
| 1333.52 | 1272.52 | 1400.66 | −64.72 | −63.22 | −65.02 | −66.33 | −65.74 | −62.20 | −60.53 | −62.89 | −65.42 | −65.06 |
| 1467.80 | 1400.66 | 1541.70 | −64.09 | −60.00 | −61.52 | −69.88 | −66.20 | −58.46 | −55.59 | −59.01 | −67.56 | −67.39 |
| 1615.60 | 1541.70 | 1696.94 | −64.68 | −60.72 | −62.35 | −68.59 | −65.63 | −59.77 | −56.65 | −59.61 | −68.61 | −68.34 |
| 1778.28 | 1696.94 | 1867.81 | −62.26 | −60.83 | −64.89 | −70.09 | −65.68 | −58.20 | −58.52 | −65.20 | −68.26 | −67.31 |
| 1957.34 | 1867.81 | 2055.89 | −67.32 | −65.37 | −67.96 | −72.23 | −69.68 | −63.43 | −62.46 | −67.02 | −70.49 | −70.04 |
| 2154.43 | 2055.89 | 2262.90 | −64.82 | −62.93 | −65.71 | −71.24 | −68.28 | −60.72 | −60.31 | −66.59 | −71.91 | −70.25 |
| 2371.37 | 2262.90 | 2490.77 | −68.81 | −67.06 | −69.20 | −73.63 | −70.11 | −64.80 | −62.45 | −65.62 | −71.28 | −70.54 |
| 2610.16 | 2490.77 | 2741.57 | −68.50 | −68.02 | −70.72 | −73.89 | −69.71 | −65.08 | −70.37 | −71.03 | −69.43 |
| 2872.98 | 2741.57 | 3017.63 | −68.42 | −68.69 | −71.45 | −74.99 | −69.88 | −65.15 | −65.16 | −69.82 | −72.42 | −72.23 |
| 3162.28 | 3017.63 | 3321.49 | −69.54 | −68.60 | −71.28 | −75.26 | −71.12 | −65.31 | −64.96 | −70.55 | −73.17 | −71.52 |
| 3480.70 | 3321.49 | 3655.94 | −71.33 | −71.59 | −74.23 | −76.95 | −72.28 | −67.83 | −67.91 | −72.77 | −72.81 | −71.49 |
| 3831.19 | 3655.94 | 4024.08 | −71.46 | −73.29 | −76.02 | −77.68 | −72.54 | −69.36 | −70.31 | −74.05 | −75.68 | −74.24 |
| 4216.97 | 4024.08 | 4429.28 | −72.81 | −74.49 | −76.78 | −79.53 | −73.83 | −70.35 | −70.80 | −74.59 | −75.43 | −73.64 |
| 4641.59 | 4429.28 | 4875.28 | −74.82 | −75.49 | −77.71 | −80.55 | −75.88 | −71.65 | −71.50 | −75.58 | −77.50 | −76.32 |
| 5108.97 | 4875.28 | 5366.19 | −74.76 | −75.85 | −78.22 | −80.19 | −75.72 | −71.84 | −73.03 | −79.06 | −80.26 | −79.94 |
| 5623.41 | 5366.19 | 5906.54 | −75.74 | −77.37 | −79.67 | −81.16 | −76.76 | −73.11 | −74.46 | −80.22 | −81.73 | −81.89 |
| 6189.66 | 5906.54 | 6501.29 | −78.31 | −80.37 | −82.73 | −83.86 | −79.16 | −75.76 | −76.70 | −81.28 | −81.80 | −80.39 |
| 6812.92 | 6501.29 | 7155.93 | −74.68 | −76.76 | −79.02 | −80.12 | −75.63 | −72.63 | −74.65 | −81.21 | −81.76 | −80.34 |
| 7498.94 | 7155.93 | 7876.49 | −78.24 | −80.57 | −83.56 | −83.92 | −79.11 | −76.52 | −78.01 | −81.94 | −83.21 | −82.80 |
| 8254.04 | 7876.49 | 8669.61 | −81.43 | −83.73 | −86.59 | −87.48 | −82.55 | −79.07 | −80.11 | −83.91 | −85.04 | −84.52 |
| 9085.18 | 8669.61 | 9542.59 | −83.12 | −85.49 | −87.84 | −89.00 | −84.70 | −80.41 | −80.88 | −83.95 | −85.39 | −85.64 |
| 10000.00 | 9542.59 | 10503.47 | −84.10 | −86.85 | −90.44 | −90.80 | −85.68 | −81.98 | −82.47 | −84.94 | −86.68 | −87.43 |
| 11006.94 | 10503.47 | 11561.11 | −87.36 | −89.38 | −93.03 | −94.37 | −89.28 | −84.45 | −84.58 | −87.12 | −88.53 | −89.30 |
| 12115.28 | 11561.11 | 12725.25 | −89.70 | −91.96 | −95.72 | −97.52 | −92.31 | −86.93 | −86.69 | −89.05 | −89.87 | −88.82 |
| 13335.21 | 12725.25 | 14006.60 | −92.65 | −94.43 | −98.86 | −100.92 | −95.50 | −90.99 | −90.91 | −93.99 | −94.18 | −91.84 |
| 14677.99 | 14006.60 | 15416.99 | −94.82 | −97.90 | −101.33 | −103.76 | −97.03 | −93.94 | −93.84 | −96.31 | −97.24 | −94.75 |
| 16155.98 | 15416.99 | 16969.39 | −98.19 | −99.65 | −103.37 | −104.91 | −100.12 | −96.45 | −97.27 | −99.82 | −97.86 | −96.31 |
| 17782.79 | 16969.39 | 18678.11 | −101.60 | −101.24 | −106.06 | −110.92 | −106.41 | −98.68 | −99.58 | −109.62 | −106.04 | −103.97 |
| 19573.42 | 18678.11 | 20558.88 | −103.17 | −101.91 | −106.87 | −114.45 | −108.37 | −99.51 | −100.52 | −114.67 | −112.12 | −109.45 |
| 21544.35 | 20558.88 | 22629.04 | −113.92 | −112.50 | −117.13 | −123.11 | −118.74 | −110.31 | −111.14 | −122.36 | −122.36 | −120.11 |

(section 7 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | | |
|---|---|---|---|---|---|---|---|---|---|---|---|---|
| (Hz) | (Hz) | (Hz) | 15.38 | 15.88 | 16.38 | 16.87 | 17.37 | 17.87 | 18.36 | 18.86 | 19.36 | 19.85 |
| 1.00 | 1.00 | 1.05 | −93.85 | −93.90 | −91.91 | −91.85 | −92.82 | −91.24 | −89.81 | −90.82 | −89.59 | −89.42 |
| 1.10 | 1.05 | 1.16 | −93.85 | −93.90 | −91.91 | −91.85 | −92.82 | −91.24 | −89.81 | −90.82 | −89.59 | −89.42 |
| 1.21 | 1.16 | 1.27 | −93.84 | −93.85 | −91.86 | −91.88 | −92.57 | −91.09 | −89.77 | −89.63 | −89.43 |
| 1.33 | 1.27 | 1.40 | −93.77 | −93.66 | −91.64 | −92.01 | −91.67 | −90.53 | −89.59 | −90.49 | −89.80 | −89.49 |
| 1.47 | 1.40 | 1.54 | −93.54 | −93.45 | −91.38 | −91.72 | −91.41 | −90.27 | −89.69 | −90.15 | −89.86 | −89.66 |
| 1.62 | 1.54 | 1.70 | −93.03 | −92.99 | −90.81 | −91.09 | −90.86 | −89.72 | −89.92 | −89.44 | −90.01 | −90.09 |
| 1.78 | 1.70 | 1.87 | −93.10 | −93.05 | −90.24 | −89.71 | −90.02 | −89.20 | −88.99 | −87.25 | −89.30 | −89.48 |
| 1.96 | 1.87 | 2.06 | −93.32 | −92.81 | −89.50 | −88.72 | −89.16 | −88.44 | −87.40 | −86.17 | −88.88 | −88.70 |

TABLE 2-continued

| | | | | | | | | | | | |
|---|---|---|---|---|---|---|---|---|---|---|---|
| 2.15 | 2.06 | 2.26 | −93.85 | −92.09 | −88.41 | −87.64 | −87.98 | −87.25 | −85.31 | −85.41 | −88.54 | −87.61 |
| 2.37 | 2.26 | 2.49 | −94.11 | −90.48 | −87.33 | −86.25 | −86.49 | −85.57 | −84.11 | −85.46 | −87.95 | −87.08 |
| 2.61 | 2.49 | 2.74 | −92.53 | −89.46 | −86.31 | −84.78 | −84.87 | −83.92 | −82.84 | −84.67 | −86.81 | −85.34 |
| 2.87 | 2.74 | 3.02 | −91.46 | −88.54 | −84.89 | −83.42 | −82.98 | −82.64 | −81.46 | −83.37 | −85.24 | −84.03 |
| 3.16 | 3.02 | 3.32 | −92.13 | −87.17 | −84.31 | −82.81 | −82.13 | −82.21 | −81.39 | −83.06 | −84.91 | −83.74 |
| 3.48 | 3.32 | 3.66 | −91.86 | −86.37 | −83.33 | −82.67 | −81.89 | −81.47 | −80.90 | −81.86 | −84.46 | −83.68 |
| 3.83 | 3.66 | 4.02 | −90.93 | −85.72 | −82.38 | −82.53 | −81.65 | −80.98 | −79.60 | −80.08 | −83.05 | −83.12 |
| 4.22 | 4.02 | 4.43 | −90.56 | −85.58 | −82.38 | −81.47 | −80.74 | −80.11 | −78.88 | −80.05 | −82.57 | −82.33 |
| 4.64 | 4.43 | 4.88 | −91.91 | −86.27 | −83.36 | −81.65 | −81.23 | −81.53 | −80.47 | −80.86 | −82.36 | −82.74 |
| 5.11 | 4.88 | 5.37 | −92.42 | −86.93 | −83.49 | −81.89 | −81.33 | −81.13 | −80.78 | −81.50 | −82.92 | −82.34 |
| 5.62 | 5.37 | 5.91 | −93.66 | −87.55 | −83.87 | −82.75 | −82.13 | −80.93 | −80.19 | −79.43 | −82.00 | −81.12 |
| 6.19 | 5.91 | 6.50 | −89.87 | −87.48 | −82.72 | −81.63 | −81.76 | −81.29 | −80.18 | −78.10 | −80.44 | −80.33 |
| 6.81 | 6.50 | 7.16 | −90.47 | −87.25 | −83.28 | −83.20 | −82.77 | −81.32 | −80.56 | −80.48 | −81.64 | −81.19 |
| 7.50 | 7.16 | 7.88 | −90.19 | −87.08 | −83.56 | −82.84 | −82.72 | −81.04 | −79.84 | −79.05 | −81.25 | −81.15 |
| 8.25 | 7.88 | 8.67 | −88.60 | −85.40 | −82.30 | −81.57 | −80.37 | −78.65 | −76.86 | −76.87 | −80.51 | −80.76 |
| 9.09 | 8.67 | 9.54 | −83.07 | −78.96 | −76.74 | −76.19 | −75.47 | −74.33 | −72.82 | −72.83 | −75.45 | −76.70 |
| 10.00 | 9.54 | 10.50 | −77.84 | −74.16 | −72.98 | −72.94 | −73.20 | −72.40 | −72.03 | −72.12 | −73.21 | −75.75 |
| 11.01 | 10.50 | 11.56 | −81.82 | −79.42 | −76.54 | −75.43 | −76.34 | −75.11 | −74.97 | −76.22 | −77.49 | −77.41 |
| 12.12 | 11.56 | 12.73 | −79.01 | −75.60 | −73.62 | −72.24 | −71.19 | −70.46 | −70.97 | −70.80 | −71.15 | −72.65 |
| 13.34 | 12.73 | 14.01 | −75.79 | −70.59 | −68.40 | −67.75 | −68.07 | −67.70 | −68.43 | −69.16 | −69.14 | −71.98 |
| 14.68 | 14.01 | 15.42 | −72.57 | −69.97 | −69.30 | −69.08 | −67.79 | −67.04 | −67.75 | −68.81 | −68.93 | −70.65 |
| 16.16 | 15.42 | 16.97 | −71.81 | −68.82 | −68.05 | −67.93 | −68.07 | −66.95 | −66.84 | −66.90 | −67.88 | −68.81 |
| 17.78 | 16.97 | 18.68 | −69.87 | −66.15 | −65.05 | −63.81 | −63.00 | −62.85 | −63.73 | −64.73 | −65.37 | −63.69 |
| 19.57 | 18.68 | 20.56 | −66.37 | −60.42 | −58.05 | −57.64 | −57.54 | −57.56 | −58.93 | −58.51 | −58.38 | −61.30 |
| 21.54 | 20.56 | 22.63 | −68.62 | −66.10 | −64.65 | −62.44 | −62.59 | −64.01 | −64.08 | −64.69 | −67.06 |
| 23.71 | 22.63 | 24.91 | −69.97 | −64.00 | −62.39 | −62.13 | −61.14 | −60.95 | −61.34 | −61.24 | −62.30 | −65.22 |
| 26.10 | 24.91 | 27.42 | −71.37 | −67.26 | −65.03 | −63.33 | −63.20 | −63.72 | −63.63 | −63.75 | −65.26 | −68.20 |
| 28.73 | 27.42 | 30.18 | −63.87 | −56.08 | −54.43 | −54.51 | −54.57 | −54.64 | −54.31 | −54.42 | −55.54 | −59.52 |
| 31.62 | 30.18 | 33.21 | −68.28 | −60.82 | −58.71 | −58.89 | −58.66 | −57.98 | −57.72 | −58.01 | −60.23 | −63.35 |
| 34.81 | 33.21 | 36.56 | −71.91 | −67.99 | −65.24 | −64.29 | −64.45 | −62.13 | −60.20 | −59.57 | −64.39 | −50.47 |
| 38.31 | 36.56 | 40.24 | −70.92 | −69.00 | −65.17 | −63.50 | −64.48 | −58.95 | −56.86 | −55.19 | −62.86 | −50.37 |
| 42.17 | 40.24 | 44.29 | −63.58 | −62.71 | −57.05 | −48.97 | −47.02 | −43.19 | −42.86 | −46.41 | −57.76 | −45.66 |
| 46.42 | 44.29 | 48.75 | −69.25 | −67.63 | −53.52 | −51.62 | −50.82 | −48.59 | −50.07 | −47.37 | −46.70 | −49.23 |
| 51.09 | 48.75 | 53.66 | −63.61 | −69.03 | −52.50 | −50.02 | −48.40 | −46.95 | −48.34 | −42.49 | −41.10 | −45.39 |
| 56.23 | 53.66 | 59.07 | −52.77 | −62.43 | −49.44 | −48.91 | −48.35 | −46.16 | −44.51 | −46.23 | −47.29 | −46.48 |
| 61.90 | 59.07 | 65.01 | −50.35 | −60.60 | −50.85 | −50.48 | −46.90 | −49.39 | −46.06 | −46.64 | −47.65 | −47.94 |
| 68.13 | 65.01 | 71.56 | −51.59 | −60.98 | −49.26 | −48.21 | −49.21 | −50.74 | −46.87 | −46.89 | −47.96 | −47.69 |
| 74.99 | 71.56 | 78.76 | −41.52 | −48.01 | −44.48 | −45.93 | −47.21 | −47.91 | −43.36 | −42.90 | −44.59 | −43.26 |
| 82.54 | 78.76 | 86.70 | −39.48 | −49.78 | −50.13 | −46.14 | −46.35 | −46.13 | −41.93 | −40.55 | −44.87 | −48.10 |
| 90.85 | 86.70 | 95.43 | −44.19 | −43.98 | −44.86 | −44.36 | −44.18 | −47.09 | −48.84 | −51.78 | −59.21 | −53.85 |
| 100.00 | 95.43 | 105.03 | −48.91 | −58.17 | −56.77 | −53.18 | −52.62 | −50.49 | −46.17 | −45.67 | −49.53 | −50.78 |
| 110.07 | 105.03 | 115.61 | −52.25 | −61.24 | −56.68 | −53.69 | −53.89 | −51.87 | −49.78 | −51.07 | −57.89 | −54.74 |
| 121.15 | 115.61 | 127.25 | −53.20 | −59.54 | −52.88 | −52.16 | −52.47 | −52.16 | −50.04 | −51.63 | −52.07 | −52.50 |
| 133.35 | 127.25 | 140.07 | −45.06 | −47.03 | −47.61 | −48.25 | −48.76 | −49.99 | −50.28 | −51.99 | −52.42 | −50.71 |
| 146.78 | 140.07 | 154.17 | −50.57 | −60.93 | −51.98 | −50.17 | −53.74 | −53.56 | −51.98 | −51.72 | −53.35 | −52.84 |

(section 8 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | | |
|---|---|---|---|---|---|---|---|---|---|---|---|
| (Hz) | (Hz) | (Hz) | 15.38 | 15.88 | 16.38 | 16.87 | 17.37 | 17.87 | 18.36 | 18.86 | 19.36 | 19.85 |
| 161.56 | 154.17 | 169.69 | −54.91 | −58.67 | −54.66 | −51.70 | −52.57 | −52.90 | −48.49 | −48.40 | −52.74 | −52.48 |
| 177.83 | 169.69 | 186.78 | −50.70 | −51.09 | −51.74 | −51.85 | −49.21 | −46.88 | −47.22 | −50.41 | −51.99 | −51.15 |
| 195.73 | 186.78 | 205.59 | −51.69 | −52.25 | −50.85 | −50.90 | −50.95 | −51.92 | −49.41 | −49.65 | −52.00 | −53.11 |
| 215.44 | 205.59 | 226.29 | −50.71 | −54.03 | −50.97 | −46.92 | −45.88 | −47.08 | −48.02 | −49.11 | −53.89 | −50.01 |
| 237.14 | 226.29 | 249.08 | −50.83 | −56.24 | −51.26 | −50.19 | −50.62 | −50.94 | −51.19 | −55.55 | −58.03 |
| 261.02 | 249.08 | 274.16 | −48.71 | −50.98 | −51.41 | −51.51 | −51.72 | −53.39 | −52.85 | −52.74 | −52.54 | −52.09 |
| 287.30 | 274.16 | 301.76 | −50.88 | −53.92 | −49.42 | −47.05 | −47.20 | −48.44 | −48.22 | −49.50 | −50.45 | −49.18 |
| 316.23 | 301.76 | 332.15 | −58.06 | −60.45 | −57.23 | −54.02 | −53.49 | −54.44 | −52.87 | −52.86 | −54.24 | −53.71 |
| 348.07 | 332.15 | 365.59 | −54.00 | −53.81 | −52.88 | −52.11 | −52.44 | −54.45 | −52.96 | −53.78 | −55.04 | −53.31 |
| 383.12 | 365.59 | 402.41 | −55.70 | −55.36 | −53.77 | −55.53 | −52.79 | −53.06 | −53.21 | −53.82 | −53.11 | −50.26 |
| 421.70 | 402.41 | 442.93 | −57.97 | −59.22 | −54.64 | −51.68 | −51.94 | −54.14 | −57.13 | −58.34 | −58.78 | −50.59 |
| 464.16 | 442.93 | 487.53 | −62.33 | −61.52 | −57.80 | −55.33 | −55.11 | −57.57 | −60.34 | −61.12 | −64.23 | −54.55 |
| 510.90 | 487.53 | 536.62 | −54.23 | −53.90 | −52.65 | −52.14 | −53.65 | −49.66 | −48.68 | −50.44 | −55.42 | −57.93 |
| 562.34 | 536.62 | 590.65 | −55.48 | −63.24 | −62.54 | −59.59 | −59.59 | −60.03 | −61.13 | −61.54 | −59.53 |
| 618.97 | 590.65 | 650.13 | −60.45 | −64.37 | −62.87 | −60.62 | −59.79 | −59.90 | −61.06 | −62.78 | −64.86 | −65.46 |
| 681.29 | 650.13 | 715.59 | −52.16 | −52.27 | −53.78 | −53.75 | −52.72 | −54.86 | −56.59 | −58.55 | −59.34 | −57.95 |
| 749.89 | 715.59 | 787.65 | −61.13 | −64.60 | −62.62 | −61.72 | −61.90 | −63.16 | −62.10 | −62.02 | −61.49 | −59.94 |
| 825.40 | 787.65 | 866.96 | −61.33 | −68.35 | −66.19 | −64.99 | −62.81 | −63.69 | −65.97 | −65.93 | −67.10 | −66.58 |
| 908.52 | 866.96 | 954.26 | −58.78 | −60.85 | −60.25 | −57.36 | −57.51 | −59.19 | −61.08 | −63.05 | −63.79 | −62.26 |
| 1000.00 | 954.26 | 1050.35 | −59.47 | −58.79 | −59.43 | −60.17 | −59.13 | −59.19 | −59.93 | −61.05 | −60.29 | −58.17 |
| 1100.69 | 1050.35 | 1156.11 | −64.25 | −64.09 | −64.62 | −64.89 | −64.76 | −62.15 | −59.08 | −60.58 | −66.87 | −67.75 |
| 1211.53 | 1156.11 | 1272.52 | −63.08 | −67.02 | −65.22 | −63.13 | −63.10 | −61.65 | −61.45 | −63.29 | −64.99 | −63.40 |
| 1333.52 | 1272.52 | 1400.66 | −63.72 | −63.50 | −63.30 | −63.05 | −62.56 | −60.88 | −60.31 | −63.49 | −65.96 | −65.91 |
| 1467.80 | 1400.66 | 1541.70 | −66.90 | −67.40 | −65.06 | −65.02 | −66.64 | −66.33 | −64.91 | −65.49 | −68.31 | −70.21 |
| 1615.60 | 1541.70 | 1696.94 | −70.54 | −72.51 | −70.81 | −70.98 | −70.68 | −71.42 | −70.44 | −70.09 | −70.00 | −68.54 |
| 1778.28 | 1696.94 | 1867.81 | −67.45 | −68.77 | −68.35 | −68.53 | −68.20 | −68.71 | −70.79 | −72.74 | −73.22 | −70.35 |
| 1957.34 | 1867.81 | 2055.89 | −71.70 | −73.18 | −70.86 | −70.27 | −71.46 | −73.37 | −72.75 | −72.81 | −74.40 | −75.03 |

TABLE 2-continued

| | | | | | | | | | | | |
|---|---|---|---|---|---|---|---|---|---|---|---|
| 2154.43 | 2055.89 | 2262.90 | −70.21 | −71.03 | −71.51 | −72.86 | −72.56 | −72.17 | −71.30 | −72.40 | −76.90 | −77.91 |
| 2371.37 | 2262.90 | 2490.77 | −72.37 | −76.93 | −75.79 | −72.84 | −72.16 | −72.38 | −70.10 | −70.85 | −76.32 | −77.28 |
| 2610.16 | 2490.77 | 2741.57 | −71.19 | −74.91 | −74.73 | −74.26 | −74.83 | −71.76 | −69.96 | −71.87 | −75.46 | −75.47 |
| 2872.98 | 2741.57 | 3017.63 | −74.04 | −78.23 | −76.92 | −74.85 | −73.69 | −72.24 | −71.31 | −73.51 | −78.07 | −80.76 |
| 3162.28 | 3017.63 | 3321.49 | −73.17 | −78.33 | −77.93 | −76.39 | −76.53 | −76.03 | −73.87 | −74.55 | −78.83 | −83.78 |
| 3480.70 | 3321.49 | 3655.94 | −74.16 | −79.72 | −78.46 | −77.29 | −77.69 | −77.93 | −75.81 | −76.72 | −80.27 | −80.91 |
| 3831.19 | 3655.94 | 4024.08 | −75.49 | −82.65 | −81.87 | −79.57 | −79.41 | −76.35 | −73.47 | −75.71 | −85.16 | −86.73 |
| 4216.97 | 4024.08 | 4429.28 | −76.13 | −83.21 | −82.98 | −81.22 | −81.18 | −78.09 | −74.49 | −76.42 | −84.65 | −90.39 |
| 4641.59 | 4429.28 | 4875.28 | −78.81 | −87.94 | −86.08 | −83.67 | −84.86 | −86.14 | −82.83 | −82.58 | −86.64 | −90.86 |
| 5108.97 | 4875.28 | 5366.19 | −82.28 | −87.58 | −87.35 | −87.62 | −88.24 | −84.05 | −82.39 | −85.08 | −87.60 | −88.98 |
| 5623.41 | 5366.19 | 5906.54 | −84.01 | −92.69 | −90.53 | −88.29 | −89.43 | −86.67 | −82.62 | −84.09 | −91.32 | −95.31 |
| 6189.66 | 5906.54 | 6501.29 | −82.62 | −95.24 | −93.00 | −90.48 | −92.28 | −90.39 | −86.62 | −87.93 | −94.24 | −97.14 |
| 6812.92 | 6501.29 | 7155.93 | −82.24 | −93.43 | −94.29 | −93.02 | −92.95 | −89.26 | −85.36 | −87.00 | −92.72 | −94.58 |
| 7498.94 | 7155.93 | 7876.49 | −84.68 | −96.50 | −98.06 | −95.19 | −95.71 | −95.27 | −92.34 | −93.34 | −100.20 | −99.80 |
| 8254.04 | 7876.49 | 8669.61 | −86.39 | −98.17 | −99.23 | −97.75 | −98.53 | −95.04 | −91.13 | −92.22 | −98.74 | −102.00 |
| 9085.18 | 8669.61 | 9542.59 | −87.82 | −100.15 | −98.74 | −96.62 | −97.00 | −95.72 | −94.99 | −97.38 | −100.64 | −100.00 |
| 10000.00 | 9542.59 | 10503.47 | −89.20 | −101.64 | −99.38 | −97.55 | −100.74 | −97.80 | −94.12 | −95.30 | −102.41 | −104.68 |
| 11006.94 | 10503.47 | 11561.11 | −91.76 | −103.91 | −103.14 | −99.58 | −100.60 | −98.06 | −93.37 | −94.37 | −102.53 | −105.31 |
| 12115.28 | 11561.11 | 12725.25 | −90.72 | −104.79 | −104.75 | −96.72 | −96.53 | −94.76 | −93.48 | −97.40 | −103.13 | −103.84 |
| 13335.21 | 12725.25 | 14006.60 | −93.86 | −106.72 | −106.08 | −102.81 | −103.15 | −101.50 | −97.96 | −99.52 | −104.37 | −104.09 |
| 14677.99 | 14006.60 | 15416.99 | −97.09 | −110.19 | −110.96 | −107.96 | −109.23 | −105.36 | −102.76 | −104.70 | −109.89 | −112.63 |
| 16155.98 | 15416.99 | 16969.39 | −98.43 | −102.37 | −100.89 | −101.29 | −101.96 | −100.47 | −99.73 | −99.94 | −100.89 | −104.48 |
| 17782.79 | 16969.39 | 18678.11 | −106.92 | −115.62 | −113.47 | −110.43 | −111.22 | −107.94 | −105.08 | −106.81 | −111.01 | −114.53 |
| 19573.42 | 18678.11 | 20558.88 | −111.73 | −117.92 | −114.82 | −112.18 | −113.22 | −110.19 | −107.32 | −108.58 | −112.25 | −115.52 |
| 21544.35 | 20558.88 | 22629.04 | −116.99 | −113.99 | −113.47 | −113.49 | −113.71 | −113.12 | −112.32 | −112.82 | −113.71 | −113.87 |

(section 9 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | | |
|---|---|---|---|---|---|---|---|---|---|---|---|
| (Hz) | (Hz) | (Hz) | 20.35 | 20.84 | 21.34 | 21.84 | 22.33 | 22.83 | 23.33 | 23.82 | 24.32 | 24.81 |
| 1.00 | 1.00 | 1.05 | −90.97 | −90.66 | −89.39 | −90.67 | −92.52 | −92.23 | −91.88 | −91.65 | −91.39 | −93.23 |
| 1.10 | 1.05 | 1.16 | −90.97 | −90.66 | −89.39 | −90.67 | −92.52 | −92.23 | −91.88 | −91.65 | −91.39 | −93.23 |
| 1.21 | 1.16 | 1.27 | −91.05 | −90.68 | −89.25 | −90.50 | −92.56 | −92.21 | −91.61 | −91.23 | −91.24 | −92.96 |
| 1.33 | 1.27 | 1.40 | −91.40 | −90.78 | −88.73 | −89.87 | −92.71 | −92.13 | −90.63 | −89.80 | −90.67 | −91.99 |
| 1.47 | 1.40 | 1.54 | −91.66 | −90.90 | −88.68 | −89.54 | −92.22 | −91.83 | −89.87 | −88.66 | −89.86 | −90.94 |
| 1.62 | 1.54 | 1.70 | −92.32 | −91.19 | −88.55 | −88.84 | −91.22 | −91.18 | −88.47 | −86.77 | −88.39 | −89.15 |
| 1.78 | 1.70 | 1.87 | −91.23 | −90.71 | −87.61 | −87.94 | −90.94 | −90.79 | −88.71 | −86.75 | −88.05 | −88.47 |
| 1.96 | 1.87 | 2.06 | −89.84 | −89.81 | −86.77 | −87.25 | −90.72 | −90.59 | −89.11 | −87.18 | −88.09 | −88.33 |
| 2.15 | 2.06 | 2.26 | −88.07 | −88.45 | −85.81 | −86.45 | −90.37 | −90.41 | −89.74 | −88.41 | −88.53 | −88.62 |
| 2.37 | 2.26 | 2.49 | −86.96 | −87.63 | −85.52 | −85.36 | −88.86 | −89.07 | −87.97 | −87.98 | −88.01 | −87.84 |
| 2.61 | 2.49 | 2.74 | −85.60 | −86.23 | −85.09 | −84.58 | −87.43 | −87.31 | −86.90 | −87.21 | −86.79 | −86.85 |
| 2.87 | 2.74 | 3.02 | −84.31 | −84.88 | −85.07 | −85.07 | −86.43 | −86.63 | −86.14 | −85.82 | −86.54 | |
| 3.16 | 3.02 | 3.32 | −84.06 | −84.97 | −85.14 | −84.93 | −85.24 | −85.11 | −84.08 | −84.22 | −84.59 | −85.91 |
| 3.48 | 3.32 | 3.66 | −83.51 | −84.19 | −84.37 | −83.20 | −83.38 | −83.39 | −83.72 | −83.50 | −83.45 | −84.49 |
| 3.83 | 3.66 | 4.02 | −83.56 | −84.56 | −83.65 | −80.72 | −81.30 | −84.18 | −84.61 | −85.25 | −84.45 | −85.01 |
| 4.22 | 4.02 | 4.43 | −82.66 | −83.90 | −83.26 | −80.33 | −81.59 | −84.48 | −83.53 | −84.99 | −84.40 | −84.71 |
| 4.64 | 4.43 | 4.88 | −83.76 | −84.10 | −83.64 | −82.74 | −84.74 | −85.30 | −83.17 | −84.11 | −83.27 | −83.82 |
| 5.11 | 4.88 | 5.37 | −82.53 | −82.80 | −81.40 | −82.08 | −86.54 | −85.26 | −82.18 | −82.70 | −83.55 | −84.22 |
| 5.62 | 5.37 | 5.91 | −81.52 | −82.65 | −81.10 | −81.05 | −84.72 | −84.63 | −82.82 | −83.75 | −84.21 | −85.19 |
| 6.19 | 5.91 | 6.50 | −80.66 | −82.47 | −81.11 | −80.33 | −83.41 | −84.68 | −84.39 | −85.36 | −85.51 | −87.05 |
| 6.81 | 6.50 | 7.16 | −80.78 | −82.87 | −82.93 | −81.25 | −83.85 | −88.47 | −85.40 | −85.56 | −86.98 | −88.59 |
| 7.50 | 7.16 | 7.88 | −80.90 | −82.84 | −83.05 | −82.00 | −85.02 | −88.63 | −86.34 | −86.34 | −86.31 | −87.61 |
| 8.25 | 7.88 | 8.67 | −80.41 | −81.00 | −80.81 | −80.34 | −83.64 | −87.21 | −84.86 | −84.74 | −85.21 | −86.89 |
| 9.09 | 8.67 | 9.54 | −77.16 | −78.52 | −78.21 | −77.27 | −80.78 | −84.48 | −83.63 | −83.68 | −82.71 | −84.30 |
| 10.00 | 9.54 | 10.50 | −77.90 | −79.35 | −79.26 | −79.11 | −82.29 | −82.75 | −82.04 | −83.40 | −83.58 | −85.55 |
| 11.01 | 10.50 | 11.56 | −77.87 | −79.35 | −79.25 | −77.76 | −79.42 | −82.42 | −80.89 | −81.72 | −82.76 | −85.31 |
| 12.12 | 11.56 | 12.73 | −75.20 | −76.96 | −75.64 | −72.52 | −74.40 | −82.05 | −80.96 | −81.90 | −80.85 | −81.39 |
| 13.34 | 12.73 | 14.01 | −76.66 | −76.49 | −76.35 | −74.87 | −77.13 | −80.37 | −79.79 | −80.64 | −79.87 | −78.77 |
| 14.68 | 14.01 | 15.42 | −74.37 | −72.76 | −74.21 | −74.07 | −75.36 | −74.60 | −75.05 | −74.95 | −75.84 | −72.78 |
| 16.16 | 15.42 | 16.97 | −69.09 | −69.36 | −69.20 | −68.35 | −69.82 | −71.62 | −70.19 | −69.66 | −71.68 | −72.86 |
| 17.78 | 16.97 | 18.68 | −62.82 | −62.52 | −61.95 | −61.96 | −62.38 | −62.15 | −62.29 | −62.37 | −63.41 | −63.79 |
| 19.57 | 18.68 | 20.56 | −63.17 | −63.12 | −62.61 | −62.06 | −62.05 | −63.06 | −63.21 | −64.37 | −65.38 | −64.51 |
| 21.54 | 20.56 | 22.63 | −70.21 | −71.47 | −71.46 | −69.13 | −70.68 | −73.37 | −73.97 | −73.78 | −72.23 | −73.56 |
| 23.71 | 22.63 | 24.91 | −69.44 | −69.51 | −65.27 | −62.07 | −61.11 | −60.85 | −62.57 | −60.83 | −59.95 | −59.29 |
| 26.10 | 24.91 | 27.42 | −70.08 | −70.49 | −69.60 | −67.35 | −69.24 | −75.83 | −75.35 | −74.63 | −72.84 | −71.84 |
| 28.73 | 27.42 | 30.18 | −68.71 | −69.66 | −68.17 | −65.18 | −66.93 | −75.31 | −74.26 | −73.16 | −71.13 | −70.80 |
| 31.62 | 30.18 | 33.21 | −66.50 | −67.38 | −65.60 | −61.73 | −63.28 | −74.20 | −72.13 | −71.55 | −70.63 | −71.23 |
| 34.81 | 33.21 | 36.56 | −50.55 | −64.72 | −63.15 | −58.64 | −59.79 | −70.45 | −70.43 | −69.52 | −67.53 | −68.33 |
| 38.31 | 36.56 | 40.24 | −50.25 | −59.92 | −58.06 | −53.81 | −54.82 | −67.86 | −66.54 | −65.10 | −63.65 | −64.53 |
| 42.17 | 40.24 | 44.29 | −41.61 | −43.92 | −47.16 | −44.16 | −46.60 | −67.13 | −61.81 | −50.81 | −50.41 | −55.98 |
| 46.42 | 44.29 | 48.75 | −49.17 | −50.65 | −52.49 | −54.42 | −56.48 | −55.89 | −49.14 | −47.59 | −46.34 | −49.72 |
| 51.09 | 48.75 | 53.66 | −49.71 | −48.05 | −47.48 | −52.91 | −62.11 | −49.12 | −43.71 | −42.17 | −39.76 | −43.21 |
| 56.23 | 53.66 | 59.07 | −47.18 | −42.56 | −41.31 | −43.43 | −51.23 | −42.28 | −40.95 | −46.19 | −47.47 | −44.84 |
| 61.90 | 59.07 | 65.01 | −55.88 | −54.15 | −50.53 | −47.20 | −46.09 | −47.29 | −53.32 | −57.56 | −53.83 | −51.07 |
| 68.13 | 65.01 | 71.56 | −51.18 | −49.58 | −47.00 | −47.32 | −49.68 | −52.69 | −60.14 | −61.37 | −61.40 | −61.38 |
| 74.99 | 71.56 | 78.76 | −46.31 | −48.50 | −45.20 | −41.58 | −41.10 | −44.29 | −50.13 | −52.95 | −52.91 | −53.24 |

TABLE 2-continued

| | | | | | | | | | | | |
|---|---|---|---|---|---|---|---|---|---|---|---|
| 82.54 | 78.76 | 86.70 | −46.73 | −46.89 | −41.02 | −38.58 | −42.17 | −60.53 | −55.45 | −52.03 | −49.46 | −46.00 |
| 90.85 | 86.70 | 95.43 | −50.75 | −52.16 | −56.07 | −55.54 | −59.59 | −70.55 | −56.30 | −50.66 | −52.97 | −53.96 |
| 100.00 | 95.43 | 105.03 | −52.95 | −52.32 | −50.64 | −45.54 | −46.94 | −57.78 | −52.76 | −51.22 | −50.82 | −53.82 |
| 110.07 | 105.03 | 115.61 | −54.28 | −55.57 | −54.98 | −49.75 | −53.37 | −58.54 | −54.65 | −55.71 | −56.94 | −57.51 |
| 121.15 | 115.61 | 127.25 | −54.15 | −54.37 | −52.89 | −50.88 | −52.68 | −50.86 | −51.69 | −53.68 | −52.09 | −51.44 |
| 133.35 | 127.25 | 140.07 | −50.35 | −51.53 | −51.51 | −52.53 | −54.57 | −52.23 | −51.41 | −49.52 | −47.43 | −48.98 |
| 146.78 | 140.07 | 154.17 | −53.63 | −55.24 | −53.81 | −52.32 | −51.84 | −50.25 | −50.42 | −48.78 | −49.09 | −53.03 |

(section 10 of 28): Time-Frequency Spectral Analysis Results

| Bin Frequency (Hz) | Bin Start Frequency (Hz) | Bin Stop Frequency (Hz) | Average Signal Power Density per Bin Width (dBfs/Hz) vs Time and Frequency Time (min): | | | | | | | | | |
|---|---|---|---|---|---|---|---|---|---|---|---|
| | | | 20.35 | 20.84 | 21.34 | 21.84 | 22.33 | 22.83 | 23.33 | 23.82 | 24.32 | 24.81 |
| 161.56 | 154.17 | 169.69 | −53.01 | −53.34 | −50.66 | −49.13 | −51.65 | −51.56 | −49.85 | −51.05 | −48.82 | −48.85 |
| 177.83 | 169.69 | 186.78 | −51.24 | −51.29 | −50.14 | −51.53 | −52.49 | −54.78 | −56.21 | −55.13 | −56.21 | −54.10 |
| 195.73 | 186.78 | 205.59 | −53.79 | −52.83 | −51.32 | −49.22 | −50.77 | −54.92 | −51.93 | −50.58 | −51.08 | −53.34 |
| 215.44 | 205.59 | 226.29 | −50.00 | −53.27 | −52.56 | −50.71 | −51.47 | −51.65 | −51.67 | −51.78 | −51.26 | −51.77 |
| 237.14 | 226.29 | 249.08 | −59.91 | −60.53 | −57.92 | −53.88 | −53.97 | −54.94 | −56.15 | −59.40 | −53.87 | −51.24 |
| 261.02 | 249.08 | 274.16 | −52.94 | −53.41 | −52.50 | −53.62 | −58.23 | −57.63 | −58.47 | −57.46 | −55.47 | −53.16 |
| 287.30 | 274.16 | 301.76 | −49.45 | −50.77 | −51.44 | −50.84 | −51.81 | −54.02 | −56.19 | −55.43 | −55.18 | −58.37 |
| 316.23 | 301.76 | 332.15 | −54.57 | −54.88 | −54.27 | −55.07 | −59.47 | −57.92 | −57.93 | −59.75 | −56.18 | −56.20 |
| 348.07 | 332.15 | 365.59 | −53.41 | −55.17 | −54.44 | −55.77 | −60.13 | −58.25 | −58.61 | −58.33 | −58.33 | −60.11 |
| 383.12 | 365.59 | 402.41 | −51.73 | −54.67 | −53.33 | −56.02 | −60.47 | −58.80 | −57.53 | −57.41 | −57.94 | −58.33 |
| 421.70 | 402.41 | 442.93 | −50.08 | −56.45 | −59.88 | −57.25 | −57.98 | −59.47 | −59.45 | −59.18 | −59.34 | −59.31 |
| 464.16 | 442.93 | 487.53 | −54.55 | −62.82 | −62.57 | −61.92 | −60.05 | −58.62 | −56.41 | −54.90 | −56.63 | −57.51 |
| 510.90 | 487.53 | 536.62 | −58.67 | −59.37 | −58.74 | −59.73 | −61.37 | −59.52 | −57.05 | −55.96 | −56.23 | −55.88 |
| 562.34 | 536.62 | 590.65 | −61.13 | −62.48 | −60.12 | −60.26 | −61.70 | −61.32 | −60.21 | −58.82 | −59.84 | −61.76 |
| 618.97 | 590.65 | 650.13 | −66.16 | −66.23 | −65.54 | −64.79 | −63.45 | −62.02 | −61.84 | −61.83 | −61.75 | −63.31 |
| 681.29 | 650.13 | 715.59 | −59.15 | −60.24 | −58.81 | −59.45 | −61.85 | −62.05 | −61.79 | −63.14 | −62.27 | −62.13 |
| 749.89 | 715.59 | 787.65 | −61.43 | −62.14 | −60.35 | −61.48 | −64.03 | −63.57 | −62.95 | −63.94 | −63.18 | −62.10 |
| 825.40 | 787.65 | 866.96 | −67.48 | −68.83 | −68.12 | −66.88 | −67.56 | −66.56 | −67.26 | −67.21 | −66.44 | −65.34 |
| 908.52 | 866.96 | 954.26 | −62.46 | −65.87 | −65.02 | −64.31 | −65.04 | −63.84 | −63.08 | −62.34 | −63.55 | −64.18 |
| 1000.00 | 954.26 | 1050.35 | −59.80 | −61.02 | −58.98 | −60.38 | −65.42 | −65.63 | −65.38 | −65.30 | −64.45 | −63.20 |
| 1100.69 | 1050.35 | 1156.11 | −68.09 | −69.52 | −70.13 | −69.17 | −69.45 | −69.91 | −69.90 | −70.80 | −70.90 | −68.89 |
| 1211.53 | 1156.11 | 1272.52 | −64.79 | −66.79 | −64.38 | −65.94 | −67.51 | −66.55 | −67.15 | −66.59 | −66.38 | −66.70 |
| 1333.52 | 1272.52 | 1400.66 | −67.28 | −69.01 | −67.97 | −67.89 | −69.42 | −68.66 | −69.02 | −71.40 | −71.86 | −69.61 |
| 1467.80 | 1400.66 | 1541.70 | −72.30 | −72.15 | −71.58 | −71.83 | −72.43 | −72.09 | −72.47 | −74.07 | −74.56 | −72.15 |
| 1615.60 | 1541.70 | 1696.94 | −69.65 | −71.58 | −68.78 | −69.95 | −73.60 | −73.22 | −73.11 | −73.82 | −74.41 | −73.66 |
| 1778.28 | 1696.94 | 1867.81 | −70.58 | −75.98 | −73.18 | −73.15 | −74.46 | −74.65 | −75.16 | −76.27 | −75.52 |
| 1957.34 | 1867.81 | 2055.89 | −75.88 | −75.68 | −76.25 | −76.55 | −76.71 | −75.70 | −75.54 | −77.81 | −79.10 | −77.27 |
| 2154.43 | 2055.89 | 2262.90 | −76.34 | −77.14 | −78.44 | −77.33 | −77.80 | −78.02 | −78.31 | −79.18 | −80.22 | −78.82 |
| 2371.37 | 2262.90 | 2490.77 | −78.45 | −80.60 | −80.83 | −79.46 | −79.16 | −78.96 | −78.97 | −80.38 | −81.67 | −79.93 |
| 2610.16 | 2490.77 | 2741.57 | −75.75 | −82.89 | −82.74 | −81.56 | −79.78 | −78.68 | −81.48 | −83.00 | −84.79 | −82.43 |
| 2872.98 | 2741.57 | 3017.63 | −83.71 | −84.97 | −84.50 | −83.01 | −83.02 | −83.05 | −83.41 | −85.48 | −86.63 | −84.56 |
| 3162.28 | 3017.63 | 3321.49 | −85.29 | −86.34 | −86.44 | −85.26 | −85.18 | −85.32 | −85.58 | −87.54 | −87.89 | −85.93 |
| 3480.70 | 3321.49 | 3655.94 | −86.92 | −88.47 | −88.58 | −87.08 | −86.90 | −86.67 | −87.04 | −89.22 | −90.47 | −88.31 |
| 3831.19 | 3655.94 | 4024.08 | −88.36 | −90.16 | −90.10 | −89.28 | −89.78 | −90.06 | −89.81 | −91.31 | −93.24 | −91.15 |
| 4216.97 | 4024.08 | 4429.28 | −91.95 | −94.23 | −94.00 | −92.69 | −92.26 | −92.04 | −92.87 | −95.20 | −96.78 | −94.45 |
| 4641.59 | 4429.28 | 4875.28 | −93.26 | −95.60 | −96.39 | −94.68 | −94.21 | −93.82 | −93.80 | −95.80 | −97.94 | −95.39 |
| 5108.97 | 4875.28 | 5366.19 | −94.09 | −95.97 | −96.79 | −94.99 | −94.47 | −94.37 | −94.83 | −97.11 | −98.42 | −95.35 |
| 5623.41 | 5366.19 | 5906.54 | −96.38 | −98.81 | −99.57 | −96.97 | −96.06 | −96.11 | −97.13 | −99.46 | −100.51 | −97.37 |
| 6189.66 | 5906.54 | 6501.29 | −99.27 | −101.02 | −101.55 | −99.37 | −98.36 | −97.79 | −98.52 | −100.87 | −102.73 | −98.99 |
| 6812.92 | 6501.29 | 7155.93 | −99.56 | −102.51 | −103.22 | −101.39 | −99.99 | −98.78 | −99.70 | −102.23 | −104.01 | −100.20 |
| 7498.94 | 7155.93 | 7876.49 | −101.05 | −104.73 | −104.73 | −102.68 | −100.21 | −98.07 | −99.27 | −102.04 | −104.05 | −99.37 |
| 8254.04 | 7876.49 | 8669.61 | −103.94 | −105.87 | −105.79 | −103.68 | −103.05 | −102.75 | −103.46 | −105.71 | −106.58 | −103.03 |
| 9085.18 | 8669.61 | 9542.59 | −102.13 | −107.73 | −107.48 | −104.26 | −104.12 | −105.37 | −105.75 | −107.64 | −108.25 | −105.53 |
| 10000.00 | 9542.59 | 10503.47 | −103.70 | −102.98 | −105.04 | −106.22 | −106.41 | −106.70 | −107.75 | −109.88 | −110.24 | −107.19 |
| 11006.94 | 10503.47 | 11561.11 | −108.45 | −108.55 | −110.00 | −108.37 | −104.30 | −101.77 | −103.68 | −106.74 | −108.12 | −102.72 |
| 12115.28 | 11561.11 | 12725.25 | −105.87 | −110.32 | −110.59 | −109.33 | −106.83 | −104.63 | −106.04 | −108.16 | −108.58 | −104.86 |
| 13335.21 | 12725.25 | 14006.60 | −106.12 | −112.43 | −111.76 | −111.08 | −111.36 | −111.54 | −112.33 | −113.69 | −113.76 | −111.57 |
| 14677.99 | 14006.60 | 15416.99 | −114.73 | −115.42 | −114.54 | −113.29 | −113.41 | −113.56 | −114.08 | −115.08 | −115.08 | −113.63 |
| 16155.98 | 15416.99 | 16969.39 | −112.90 | −114.18 | −114.49 | −114.45 | −113.87 | −113.21 | −113.86 | −114.49 | −113.60 | −112.24 |
| 17782.79 | 16969.39 | 18678.11 | −115.99 | −116.09 | −115.49 | −114.92 | −114.81 | −114.30 | −114.79 | −115.54 | −115.41 | −114.19 |
| 19573.42 | 18678.11 | 20558.88 | −116.38 | −116.37 | −116.18 | −116.22 | −115.69 | −114.91 | −115.45 | −115.92 | −115.78 | −114.46 |
| 21544.35 | 20558.88 | 22629.04 | −113.81 | −113.76 | −113.78 | −113.85 | −113.87 | −113.74 | −113.78 | −113.83 | −113.72 | −113.34 |

(section 11 of 28): Time-Frequency Spectral Analysis Results

| Bin Frequency (Hz) | Bin Start Frequency (Hz) | Bin Stop Frequency (Hz) | Average Signal Power Density per Bin Width (dBfs/Hz) vs Time and Frequency Time (min): | | | | | | | | | |
|---|---|---|---|---|---|---|---|---|---|---|---|
| | | | 25.31 | 25.81 | 26.30 | 26.80 | 27.30 | 27.79 | 28.29 | 28.78 | 29.28 | 29.78 |
| 1.00 | 1.00 | 1.05 | −93.02 | −89.21 | −89.74 | −90.45 | −91.86 | −92.22 | −93.20 | −89.34 | −93.67 | −92.36 |
| 1.10 | 1.05 | 1.16 | −93.02 | −89.21 | −89.74 | −90.45 | −91.86 | −92.22 | −93.20 | −89.34 | −93.67 | −92.36 |
| 1.21 | 1.16 | 1.27 | −92.72 | −89.60 | −90.11 | −90.77 | −91.76 | −92.22 | −93.26 | −89.44 | −93.55 | −92.31 |

TABLE 2-continued

| | | | | | | | | | | | |
|---|---|---|---|---|---|---|---|---|---|---|---|
| 1.33 | 1.27 | 1.40 | −91.63 | −91.77 | −92.12 | −92.42 | −91.36 | −92.22 | −93.52 | −89.88 | −93.09 | −92.12 |
| 1.47 | 1.40 | 1.54 | −90.45 | −90.58 | −90.69 | −90.90 | −90.88 | −91.66 | −92.92 | −89.79 | −92.68 | −91.77 |
| 1.62 | 1.54 | 1.70 | −88.49 | −88.63 | −88.46 | −88.60 | −89.91 | −90.57 | −91.76 | −89.58 | −91.84 | −91.03 |
| 1.78 | 1.70 | 1.87 | −88.32 | −88.47 | −87.70 | −87.81 | −88.97 | −89.90 | −91.38 | −89.26 | −91.39 | −90.69 |
| 1.96 | 1.87 | 2.06 | −88.28 | −88.48 | −87.62 | −87.50 | −88.46 | −89.61 | −91.17 | −89.15 | −91.24 | −90.34 |
| 2.15 | 2.06 | 2.26 | −88.25 | −88.53 | −88.21 | −87.49 | −88.07 | −89.41 | −90.96 | −89.24 | −91.19 | −89.72 |
| 2.37 | 2.26 | 2.49 | −86.84 | −86.88 | −88.32 | −87.44 | −87.27 | −87.59 | −89.82 | −89.51 | −89.49 | −87.64 |
| 2.61 | 2.49 | 2.74 | −86.22 | −86.31 | −87.19 | −87.47 | −85.84 | −86.23 | −88.66 | −88.91 | −86.71 | −85.54 |
| 2.87 | 2.74 | 3.02 | −86.11 | −86.33 | −86.22 | −85.93 | −85.29 | −85.64 | −87.77 | −88.10 | −84.32 | −83.85 |
| 3.16 | 3.02 | 3.32 | −83.70 | −83.91 | −85.32 | −84.46 | −84.82 | −85.07 | −85.69 | −86.29 | −83.99 | −83.78 |
| 3.48 | 3.32 | 3.66 | −81.71 | −81.76 | −84.32 | −83.74 | −84.24 | −84.76 | −84.91 | −85.45 | −85.35 | −85.33 |
| 3.83 | 3.66 | 4.02 | −82.11 | −82.22 | −83.60 | −83.29 | −83.16 | −83.63 | −85.75 | −85.85 | −85.33 | −85.03 |
| 4.22 | 4.02 | 4.43 | −83.01 | −82.68 | −82.31 | −82.35 | −83.24 | −83.08 | −85.61 | −86.20 | −85.80 | −86.08 |
| 4.64 | 4.43 | 4.88 | −83.37 | −83.79 | −84.62 | −84.74 | −84.85 | −84.73 | −86.07 | −86.44 | −86.59 | −86.36 |
| 5.11 | 4.88 | 5.37 | −82.93 | −83.19 | −84.42 | −83.93 | −84.52 | −84.82 | −86.21 | −86.58 | −85.83 | −85.26 |
| 5.62 | 5.37 | 5.91 | −84.67 | −84.10 | −86.09 | −85.10 | −84.35 | −85.51 | −87.13 | −87.54 | −85.22 | −83.58 |
| 6.19 | 5.91 | 6.50 | −85.08 | −84.02 | −85.22 | −85.04 | −84.81 | −86.34 | −87.46 | −86.68 | −85.11 | −83.69 |
| 6.81 | 6.50 | 7.16 | −87.70 | −85.46 | −84.12 | −85.40 | −86.68 | −86.20 | −87.49 | −88.25 | −86.74 | −85.20 |
| 7.50 | 7.16 | 7.88 | −88.29 | −85.78 | −85.38 | −85.97 | −86.39 | −86.79 | −88.14 | −87.52 | −85.17 | −83.82 |
| 8.25 | 7.88 | 8.67 | −85.11 | −84.17 | −85.12 | −85.39 | −84.60 | −84.74 | −86.95 | −86.15 | −83.93 | −82.93 |
| 9.09 | 8.67 | 9.54 | −83.21 | −82.63 | −84.31 | −85.06 | −82.63 | −81.58 | −83.55 | −84.13 | −83.47 | −82.15 |
| 10.00 | 9.54 | 10.50 | −84.49 | −83.40 | −83.81 | −85.09 | −83.62 | −82.31 | −84.41 | −83.64 | −82.84 | −82.34 |
| 11.01 | 10.50 | 11.56 | −84.82 | −82.45 | −82.06 | −83.19 | −82.92 | −82.56 | −84.41 | −83.89 | −81.85 | −80.62 |
| 12.12 | 11.56 | 12.73 | −80.36 | −81.06 | −81.05 | −81.89 | −81.47 | −80.77 | −82.05 | −81.88 | −80.57 | −79.64 |
| 13.34 | 12.73 | 14.01 | −78.04 | −78.35 | −78.55 | −79.35 | −78.91 | −79.19 | −81.48 | −80.94 | −79.31 | −78.48 |
| 14.68 | 14.01 | 15.42 | −71.78 | −72.91 | −74.41 | −75.63 | −75.42 | −76.30 | −76.89 | −78.29 | −79.50 | −78.44 |
| 16.16 | 15.42 | 16.97 | −71.22 | −71.87 | −71.93 | −72.16 | −72.12 | −72.51 | −72.14 | −75.02 | −78.19 | −76.74 |
| 17.78 | 16.97 | 18.68 | −63.15 | −62.74 | −62.62 | −63.14 | −62.66 | −62.25 | −62.57 | −66.37 | −77.32 | −76.50 |
| 19.57 | 18.68 | 20.56 | −63.48 | −63.15 | −64.20 | −64.45 | −64.53 | −64.65 | −64.55 | −67.39 | −77.03 | −76.23 |
| 21.54 | 20.56 | 22.63 | −73.60 | −72.23 | −72.52 | −73.99 | −74.57 | −73.00 | −72.72 | −75.57 | −75.87 | −74.80 |
| 23.71 | 22.63 | 24.91 | −58.19 | −58.84 | −59.49 | −58.59 | −58.49 | −59.65 | −60.62 | −64.92 | −75.51 | −75.52 |
| 26.10 | 24.91 | 27.42 | −70.79 | −72.13 | −72.60 | −73.84 | −73.60 | −72.71 | −73.67 | −74.95 | −74.46 | −74.17 |
| 28.73 | 27.42 | 30.18 | −70.96 | −71.28 | −71.89 | −70.73 | −70.14 | −69.44 | −70.50 | −74.84 | −73.39 | −72.60 |
| 31.62 | 30.18 | 33.21 | −71.05 | −70.57 | −71.40 | −72.61 | −72.16 | −70.14 | −70.77 | −50.91 | −50.77 | −70.35 |
| 34.81 | 33.21 | 36.56 | −68.86 | −66.90 | −65.16 | −62.99 | −62.22 | −61.81 | −63.76 | −61.82 | −56.93 | −65.28 |
| 38.31 | 36.56 | 40.24 | −66.01 | −64.71 | −61.74 | −59.69 | −59.14 | −60.69 | −62.86 | −61.60 | −55.13 | −57.31 |
| 42.17 | 40.24 | 44.29 | −56.99 | −47.05 | −45.18 | −48.30 | −50.32 | −50.42 | −56.81 | −47.53 | −41.98 | −42.43 |
| 46.42 | 44.29 | 48.75 | −50.29 | −47.92 | −48.96 | −49.55 | −53.47 | −53.24 | −58.73 | −51.93 | −50.77 | −49.41 |
| 51.09 | 48.75 | 53.66 | −43.99 | −43.02 | −46.24 | −45.28 | −46.95 | −50.07 | −59.73 | −46.95 | −44.75 | −43.05 |
| 56.23 | 53.66 | 59.07 | −45.37 | −47.78 | −48.36 | −46.59 | −42.14 | −43.11 | −48.34 | −47.12 | −47.49 | −50.99 |
| 61.90 | 59.07 | 65.01 | −50.53 | −51.96 | −55.05 | −54.34 | −50.59 | −49.65 | −49.22 | −50.51 | −50.69 | −48.77 |
| 68.13 | 65.01 | 71.56 | −54.08 | −59.58 | −56.57 | −51.73 | −48.08 | −54.37 | −47.26 | −47.49 | −44.87 | −44.70 |
| 74.99 | 71.56 | 78.76 | −57.18 | −53.35 | −44.98 | −42.08 | −43.10 | −44.61 | −46.88 | −53.84 | −53.95 | −60.16 |
| 82.54 | 78.76 | 86.70 | −47.19 | −53.55 | −60.22 | −56.23 | −51.72 | −48.14 | −49.53 | −54.80 | −51.53 | −51.33 |
| 90.85 | 86.70 | 95.43 | −50.83 | −52.64 | −54.56 | −56.71 | −51.56 | −49.22 | −49.45 | −48.02 | −46.21 | −47.33 |
| 100.00 | 95.43 | 105.03 | −48.82 | −45.89 | −49.12 | −52.36 | −51.52 | −48.77 | −46.67 | −46.90 | −46.37 | −44.98 |
| 110.07 | 105.03 | 115.61 | −57.50 | −56.41 | −54.25 | −51.53 | −49.47 | −49.36 | −51.59 | −51.05 | −52.17 | −47.57 |
| 121.15 | 115.61 | 127.25 | −51.66 | −53.86 | −55.20 | −55.93 | −56.78 | −57.09 | −51.30 | −50.76 | −51.27 | −47.89 |
| 133.35 | 127.25 | 140.07 | −50.26 | −52.60 | −54.87 | −54.96 | −51.94 | −48.45 | −48.53 | −47.15 | −45.54 | −46.93 |
| 146.78 | 140.07 | 154.17 | −52.28 | −50.76 | −49.75 | −48.89 | −50.77 | −52.42 | −54.55 | −53.70 | −50.90 | −53.32 |

(section 12 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | | |
|---|---|---|---|---|---|---|---|---|---|---|---|
| (Hz) | (Hz) | (Hz) | 25.31 | 25.81 | 26.30 | 26.80 | 27.30 | 27.79 | 28.29 | 28.78 | 29.28 | 29.78 |
| 161.56 | 154.17 | 169.69 | −50.04 | −52.51 | −55.35 | −54.20 | −52.52 | −52.73 | −55.31 | −56.12 | −53.74 | −53.23 |
| 177.83 | 169.69 | 186.78 | −50.83 | −49.21 | −50.16 | −50.40 | −50.64 | −49.92 | −48.61 | −47.87 | −48.91 | −49.99 |
| 195.73 | 186.78 | 205.59 | −49.80 | −49.56 | −51.36 | −52.19 | −52.21 | −49.33 | −48.24 | −47.77 | −48.04 | −47.73 |
| 215.44 | 205.59 | 226.29 | −51.87 | −50.55 | −49.06 | −48.22 | −46.94 | −46.44 | −46.80 | −48.27 | −51.29 | −45.99 |
| 237.14 | 226.29 | 249.08 | −50.56 | −53.65 | −58.55 | −53.42 | −53.14 | −53.14 | −52.13 | −52.77 | −53.37 | −50.90 |
| 261.02 | 249.08 | 274.16 | −52.81 | −55.81 | −58.76 | −58.06 | −55.03 | −49.84 | −48.10 | −48.08 | −49.56 | −50.04 |
| 287.30 | 274.16 | 301.76 | −54.81 | −52.06 | −51.65 | −50.67 | −48.64 | −46.69 | −47.74 | −50.39 | −53.89 | −52.67 |
| 316.23 | 301.76 | 332.15 | −56.36 | −56.27 | −59.03 | −59.57 | −57.46 | −50.78 | −48.38 | −48.36 | −49.62 | −46.62 |
| 348.07 | 332.15 | 365.59 | −57.39 | −58.60 | −60.12 | −57.67 | −54.23 | −53.44 | −52.80 | −51.74 | −51.69 | −51.76 |
| 383.12 | 365.59 | 402.41 | −55.45 | −54.80 | −56.13 | −54.70 | −51.58 | −51.32 | −50.01 | −50.52 | −48.85 | −45.23 |
| 421.70 | 402.41 | 442.93 | −54.49 | −54.28 | −57.74 | −53.11 | −53.09 | −54.28 | −53.91 | −55.83 | −52.74 | −51.59 |
| 464.16 | 442.93 | 487.53 | −56.04 | −56.05 | −55.95 | −54.71 | −54.09 | −55.37 | −59.14 | −62.05 | −61.69 | −60.12 |
| 510.90 | 487.53 | 536.62 | −55.44 | −57.66 | −60.08 | −60.99 | −54.72 | −52.97 | −52.28 | −53.15 | −56.35 | −50.67 |
| 562.34 | 536.62 | 590.65 | −60.76 | −59.09 | −59.37 | −58.93 | −57.82 | −55.42 | −55.16 | −57.61 | −59.15 | −58.20 |
| 618.97 | 590.65 | 650.13 | −62.34 | −60.02 | −60.47 | −61.20 | −56.66 | −56.15 | −59.64 | −62.81 | −62.27 | −59.38 |
| 681.29 | 650.13 | 715.59 | −60.47 | −59.28 | −59.96 | −58.77 | −56.60 | −54.75 | −54.94 | −54.64 | −51.15 |
| 749.89 | 715.59 | 787.65 | −60.97 | −61.51 | −63.43 | −62.18 | −61.12 | −60.42 | −58.23 | −58.77 | −54.81 | −53.49 |
| 825.40 | 787.65 | 866.96 | −63.18 | −62.59 | −64.76 | −67.01 | −66.49 | −64.63 | −63.27 | −63.84 | −58.59 | −57.95 |
| 908.52 | 866.96 | 954.26 | −63.05 | −61.38 | −61.89 | −62.32 | −62.01 | −61.09 | −60.83 | −62.70 | −62.92 | −61.11 |
| 1000.00 | 954.26 | 1050.35 | −61.23 | −61.82 | −64.86 | −64.65 | −62.74 | −60.93 | −59.52 | −59.74 | −60.77 | −58.28 |
| 1100.69 | 1050.35 | 1156.11 | −65.74 | −65.24 | −67.62 | −67.22 | −66.20 | −65.73 | −65.73 | −66.07 | −65.77 | −63.88 |

TABLE 2-continued

| | | | | | | | | | | | |
|---|---|---|---|---|---|---|---|---|---|---|---|
| 1211.53 | 1156.11 | 1272.52 | −64.37 | −63.86 | −66.02 | −63.92 | −60.16 | −59.55 | −60.24 | −63.93 | −64.26 | −61.72 |
| 1333.52 | 1272.52 | 1400.66 | −67.28 | −67.40 | −69.11 | −68.64 | −65.83 | −64.64 | −64.02 | −64.31 | −63.54 | −60.61 |
| 1467.80 | 1400.66 | 1541.70 | −68.93 | −69.29 | −72.03 | −70.17 | −68.41 | −67.12 | −67.42 | −69.43 | −70.84 | −69.43 |
| 1615.60 | 1541.70 | 1696.94 | −71.75 | −70.79 | −71.21 | −71.84 | −69.29 | −68.29 | −65.69 | −66.27 | −63.83 | −61.99 |
| 1778.28 | 1696.94 | 1867.81 | −73.98 | −72.76 | −72.82 | −72.13 | −68.84 | −67.67 | −68.61 | −70.52 | −70.68 | −71.24 |
| 1957.34 | 1867.81 | 2055.89 | −75.49 | −74.97 | −74.67 | −74.44 | −70.85 | −70.68 | −70.56 | −70.60 | −69.81 | −66.39 |
| 2154.43 | 2055.89 | 2262.90 | −77.41 | −77.07 | −76.44 | −76.02 | −73.03 | −71.71 | −72.33 | −73.35 | −75.30 | −71.41 |
| 2371.37 | 2262.90 | 2490.77 | −78.57 | −77.83 | −78.13 | −75.76 | −73.88 | −73.43 | −71.88 | −73.09 | −70.45 | −69.88 |
| 2610.16 | 2490.77 | 2741.57 | −81.05 | −80.13 | −80.01 | −78.81 | −75.33 | −75.02 | −74.05 | −74.50 | −75.39 | −71.48 |
| 2872.98 | 2741.57 | 3017.63 | −82.88 | −81.50 | −80.76 | −79.13 | −78.58 | −78.38 | −77.57 | −79.17 | −80.26 | −78.56 |
| 3162.28 | 3017.63 | 3321.49 | −84.74 | −83.44 | −83.68 | −83.11 | −79.53 | −79.56 | −79.20 | −79.75 | −76.64 | −74.10 |
| 3480.70 | 3321.49 | 3655.94 | −86.00 | −83.22 | −82.60 | −79.44 | −78.48 | −79.62 | −79.62 | −82.21 | −83.97 | −81.48 |
| 3831.19 | 3655.94 | 4024.08 | −88.91 | −87.67 | −84.54 | −85.49 | −82.54 | −82.40 | −83.65 | −84.79 | −81.87 | −79.51 |
| 4216.97 | 4024.08 | 4429.28 | −91.82 | −90.11 | −89.12 | −86.23 | −85.96 | −87.33 | −86.55 | −87.98 | −89.71 | −86.69 |
| 4641.59 | 4429.28 | 4875.28 | −93.17 | −91.56 | −90.11 | −87.44 | −85.34 | −85.74 | −87.01 | −89.50 | −87.51 | −85.12 |
| 5108.97 | 4875.28 | 5366.19 | −93.18 | −91.62 | −91.80 | −90.74 | −90.22 | −90.74 | −90.25 | −91.14 | −91.50 | −88.84 |
| 5623.41 | 5366.19 | 5906.54 | −95.47 | −93.41 | −92.32 | −91.83 | −91.29 | −92.51 | −92.97 | −94.59 | −93.06 | −91.98 |
| 6189.66 | 5906.54 | 6501.29 | −96.81 | −94.63 | −94.31 | −91.04 | −90.17 | −92.35 | −93.59 | −95.80 | −94.46 | −92.48 |
| 6812.92 | 6501.29 | 7155.93 | −97.56 | −94.95 | −94.58 | −91.88 | −91.41 | −93.88 | −95.15 | −97.84 | −97.42 | −95.69 |
| 7498.94 | 7155.93 | 7876.49 | −97.07 | −94.85 | −94.19 | −93.03 | −92.81 | −95.03 | −96.60 | −99.08 | −98.61 | −96.32 |
| 8254.04 | 7876.49 | 8669.61 | −100.87 | −100.43 | −100.73 | −98.52 | −97.99 | −99.17 | −99.41 | −100.72 | −99.57 | −97.53 |
| 9085.18 | 8669.61 | 9542.59 | −103.56 | −102.66 | −102.61 | −100.63 | −99.82 | −100.76 | −101.44 | −103.03 | −102.24 | −100.60 |
| 10000.00 | 9542.59 | 10503.47 | −103.07 | −102.49 | −104.27 | −102.14 | −100.28 | −100.85 | −103.16 | −104.50 | −105.04 | −103.55 |
| 11006.94 | 10503.47 | 11561.11 | −100.30 | −98.34 | −97.86 | −95.17 | −94.86 | −97.70 | −100.44 | −105.82 | −106.38 | −105.47 |
| 12115.28 | 11561.11 | 12725.25 | −102.33 | −100.89 | −100.70 | −99.00 | −98.81 | −100.88 | −102.55 | −101.95 | −102.25 | −107.91 |
| 13335.21 | 12725.25 | 14006.60 | −108.02 | −107.54 | −108.77 | −105.82 | −105.04 | −106.33 | −107.33 | −104.06 | −104.07 | −111.46 |
| 14677.99 | 14006.60 | 15416.99 | −112.29 | −111.26 | −111.09 | −108.42 | −107.36 | −108.31 | −109.94 | −114.16 | −114.43 | −113.91 |
| 16155.98 | 15416.99 | 16969.39 | −111.08 | −110.15 | −110.01 | −107.41 | −106.66 | −107.90 | −109.39 | −113.86 | −115.76 | −115.60 |
| 17782.79 | 16969.39 | 18678.11 | −113.16 | −112.14 | −111.83 | −109.54 | −108.84 | −110.35 | −112.03 | −115.86 | −116.59 | −116.61 |
| 19573.42 | 18678.11 | 20558.88 | −113.68 | −112.76 | −112.19 | −110.35 | −109.98 | −111.48 | −113.07 | −116.28 | −116.97 | −116.95 |
| 21544.35 | 20558.88 | 22629.04 | −113.13 | −112.86 | −112.60 | −111.96 | −111.79 | −112.16 | −112.76 | −114.00 | −114.35 | −114.34 |

(section 13 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | |
|---|---|---|---|---|---|---|---|---|---|---|---|
| (Hz) | (Hz) | (Hz) | 30.27 | 30.77 | 31.27 | 31.76 | 32.26 | 32.76 | 33.25 | 33.75 | 34.24 | 34.74 |
| 1.00 | 1.00 | 1.05 | −89.39 | −91.76 | −93.95 | −90.25 | −89.16 | −87.92 | −87.62 | −89.36 | −90.77 | −91.09 |
| 1.10 | 1.05 | 1.16 | −89.39 | −91.76 | −93.95 | −90.25 | −89.16 | −87.92 | −87.62 | −89.36 | −90.77 | −91.09 |
| 1.21 | 1.16 | 1.27 | −89.50 | −91.70 | −93.86 | −90.22 | −88.99 | −87.57 | −87.43 | −89.10 | −90.33 | −90.80 |
| 1.33 | 1.27 | 1.40 | −89.99 | −91.43 | −93.50 | −90.10 | −88.33 | −86.38 | −86.73 | −88.16 | −88.89 | −89.78 |
| 1.47 | 1.40 | 1.54 | −89.95 | −91.35 | −92.88 | −89.81 | −88.00 | −85.97 | −86.45 | −87.69 | −88.15 | −89.33 |
| 1.62 | 1.54 | 1.70 | −89.88 | −91.18 | −91.69 | −89.19 | −87.31 | −85.13 | −85.86 | −86.73 | −86.78 | −88.40 |
| 1.78 | 1.70 | 1.87 | −89.47 | −90.55 | −91.35 | −89.16 | −87.49 | −84.92 | −85.68 | −86.22 | −86.77 | −88.22 |
| 1.96 | 1.87 | 2.06 | −88.70 | −89.97 | −90.95 | −89.18 | −87.15 | −84.87 | −85.54 | −85.81 | −86.41 | −87.82 |
| 2.15 | 2.06 | 2.26 | −87.47 | −89.18 | −90.32 | −89.18 | −86.21 | −84.94 | −85.40 | −85.37 | −85.57 | −87.06 |
| 2.37 | 2.26 | 2.49 | −86.71 | −87.95 | −89.50 | −88.03 | −85.20 | −84.49 | −85.62 | −85.11 | −84.44 | −86.08 |
| 2.61 | 2.49 | 2.74 | −86.28 | −87.11 | −89.25 | −87.81 | −85.88 | −84.57 | −85.43 | −84.80 | −83.65 | −85.49 |
| 2.87 | 2.74 | 3.02 | −85.83 | −86.85 | −87.81 | −85.79 | −83.92 | −83.56 | −84.27 | −82.78 | −82.54 | −84.57 |
| 3.16 | 3.02 | 3.32 | −85.88 | −86.05 | −87.62 | −85.17 | −83.08 | −83.24 | −83.86 | −82.70 | −83.16 | −85.28 |
| 3.48 | 3.32 | 3.66 | −85.11 | −85.72 | −86.73 | −85.27 | −82.55 | −82.10 | −82.02 | −82.48 | −83.92 | −85.12 |
| 3.83 | 3.66 | 4.02 | −85.71 | −85.81 | −85.77 | −83.28 | −79.82 | −79.53 | −79.02 | −79.85 | −81.89 | −81.72 |
| 4.22 | 4.02 | 4.43 | −86.19 | −85.79 | −86.28 | −81.66 | −78.42 | −80.05 | −79.84 | −80.40 | −81.59 | −81.39 |
| 4.64 | 4.43 | 4.88 | −84.97 | −85.06 | −86.27 | −82.43 | −79.51 | −80.64 | −81.29 | −83.17 | −83.45 | −84.09 |
| 5.11 | 4.88 | 5.37 | −83.06 | −83.72 | −84.60 | −82.20 | −79.33 | −79.75 | −80.70 | −81.71 | −81.81 | −83.74 |
| 5.62 | 5.37 | 5.91 | −82.64 | −83.53 | −84.19 | −79.16 | −76.78 | −78.28 | −80.05 | −80.13 | −80.14 | −80.98 |
| 6.19 | 5.91 | 6.50 | −84.23 | −85.09 | −84.48 | −77.87 | −75.85 | −77.63 | −79.68 | −80.96 | −81.44 | −80.66 |
| 6.81 | 6.50 | 7.16 | −85.03 | −84.80 | −84.14 | −79.06 | −77.38 | −78.46 | −79.95 | −81.42 | −81.76 | −81.44 |
| 7.50 | 7.16 | 7.88 | −83.98 | −83.52 | −82.61 | −79.41 | −75.33 | −74.68 | −76.95 | −78.71 | −79.79 | −81.78 |
| 8.25 | 7.88 | 8.67 | −82.52 | −81.88 | −81.32 | −78.39 | −74.04 | −72.88 | −75.06 | −77.12 | −77.42 | −77.86 |
| 9.09 | 8.67 | 9.54 | −81.06 | −80.27 | −78.54 | −72.48 | −70.57 | −71.40 | −72.90 | −74.74 | −76.42 | −77.02 |
| 10.00 | 9.54 | 10.50 | −82.10 | −78.59 | −75.49 | −73.32 | −72.68 | −73.59 | −73.94 | −74.05 | −75.76 | −77.92 |
| 11.01 | 10.50 | 11.56 | −80.81 | −77.85 | −75.51 | −75.13 | −73.86 | −72.98 | −73.27 | −73.79 | −75.12 | −72.17 |
| 12.12 | 11.56 | 12.73 | −79.65 | −76.52 | −73.55 | −71.99 | −69.77 | −68.25 | −69.45 | −69.43 | −70.38 | −71.19 |
| 13.34 | 12.73 | 14.01 | −77.99 | −73.04 | −70.35 | −70.83 | −72.15 | −70.80 | −69.45 | −69.84 | −72.73 | −64.03 |
| 14.68 | 14.01 | 15.42 | −78.43 | −73.25 | −70.05 | −70.79 | −70.72 | −69.50 | −68.78 | −69.62 | −72.17 | −73.40 |
| 16.16 | 15.42 | 16.97 | −77.01 | −72.44 | −68.68 | −68.74 | −67.53 | −66.18 | −65.89 | −66.46 | −68.15 | −67.31 |
| 17.78 | 16.97 | 18.68 | −77.01 | −74.21 | −69.64 | −69.03 | −69.24 | −68.26 | −68.76 | −70.39 | −57.92 |
| 19.57 | 18.68 | 20.56 | −76.67 | −75.05 | −72.31 | −70.52 | −66.22 | −64.95 | −66.09 | −67.26 | −68.57 | −69.05 |
| 21.54 | 20.56 | 22.63 | −75.55 | −73.53 | −71.86 | −69.56 | −66.59 | −66.34 | −66.92 | −67.98 | −69.43 | −64.14 |
| 23.71 | 22.63 | 24.91 | −75.97 | −72.60 | −70.80 | −68.52 | −64.96 | −64.27 | −65.15 | −65.64 | −66.77 | −66.40 |
| 26.10 | 24.91 | 27.42 | −74.41 | −71.53 | −70.52 | −67.75 | −63.98 | −63.13 | −63.97 | −65.15 | −65.99 | −67.24 |
| 28.73 | 27.42 | 30.18 | −72.61 | −70.34 | −68.68 | −66.22 | −61.79 | −61.41 | −62.50 | −63.19 | −64.08 | −63.10 |
| 31.62 | 30.18 | 33.21 | −49.80 | −44.85 | −46.51 | −50.84 | −58.42 | −57.96 | −58.92 | −59.86 | −61.09 | −61.99 |
| 34.81 | 33.21 | 36.56 | −62.62 | −54.02 | −52.56 | −53.48 | −50.95 | −50.76 | −50.71 | −51.71 | −54.64 | −58.26 |
| 38.31 | 36.56 | 40.24 | −62.02 | −60.32 | −59.24 | −58.90 | −51.38 | −49.54 | −50.25 | −50.62 | −51.72 | −53.16 |
| 42.17 | 40.24 | 44.29 | −47.35 | −44.27 | −42.97 | −47.96 | −41.87 | −40.18 | −41.79 | −43.04 | −43.21 | −43.83 |

TABLE 2-continued

| | | | | | | | | | | | |
|---|---|---|---|---|---|---|---|---|---|---|---|
| 46.42 | 44.29 | 48.75 | −46.76 | −47.36 | −49.83 | −53.22 | −49.75 | −48.04 | −50.29 | −49.82 | −46.65 | −48.13 |
| 51.09 | 48.75 | 53.66 | −38.15 | −37.79 | −41.85 | −46.95 | −47.40 | −47.09 | −51.17 | −47.37 | −42.50 | −44.20 |
| 56.23 | 53.66 | 59.07 | −44.08 | −42.45 | −44.77 | −46.40 | −47.39 | −46.48 | −46.00 | −44.56 | −42.62 | −44.69 |
| 61.90 | 59.07 | 65.01 | −51.36 | −52.01 | −48.92 | −46.08 | −45.11 | −44.98 | −45.57 | −46.44 | −48.49 | −48.45 |
| 68.13 | 65.01 | 71.56 | −47.11 | −46.21 | −43.97 | −42.35 | −42.73 | −43.75 | −43.73 | −44.36 | −47.42 | −46.17 |
| 74.99 | 71.56 | 78.76 | −60.93 | −54.78 | −49.47 | −43.61 | −40.36 | −39.79 | −41.15 | −42.93 | −44.03 | −43.16 |
| 82.54 | 78.76 | 86.70 | −50.24 | −48.37 | −44.53 | −35.73 | −33.63 | −34.49 | −36.22 | −37.44 | −38.51 | −38.65 |
| 90.85 | 86.70 | 95.43 | −44.58 | −47.02 | −46.80 | −50.07 | −49.97 | −47.56 | −48.96 | −51.58 | −52.76 | −52.78 |
| 100.00 | 95.43 | 105.03 | −40.39 | −39.99 | −44.15 | −43.70 | −41.67 | −42.08 | −42.19 | −42.14 | −42.89 | −44.07 |
| 110.07 | 105.03 | 115.61 | −47.05 | −51.41 | −51.04 | −48.78 | −46.85 | −48.13 | −48.92 | −49.64 | −50.16 | −52.08 |
| 121.15 | 115.61 | 127.25 | −49.95 | −49.27 | −48.04 | −47.43 | −45.68 | −45.49 | −46.42 | −47.41 | −48.35 | −48.24 |
| 133.35 | 127.25 | 140.07 | −50.58 | −51.02 | −49.39 | −46.30 | −46.04 | −47.02 | −46.67 | −47.25 | −48.17 | −46.32 |
| 146.78 | 140.07 | 154.17 | −53.13 | −52.15 | −47.62 | −46.96 | −48.98 | −49.45 | −51.54 | −52.58 | −52.07 | −52.06 |

(section 14 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | |
|---|---|---|---|---|---|---|---|---|---|---|---|
| (Hz) | (Hz) | (Hz) | 30.27 | 30.77 | 31.27 | 31.76 | 32.26 | 32.76 | 33.25 | 33.75 | 34.24 | 34.74 |
| 161.56 | 154.17 | 169.69 | −52.86 | −51.58 | −46.64 | −43.60 | −42.49 | −42.76 | −43.04 | −43.18 | −44.00 | −44.46 |
| 177.83 | 169.69 | 186.78 | −45.85 | −49.09 | −50.57 | −52.89 | −52.31 | −51.10 | −53.03 | −54.07 | −53.17 | −49.25 |
| 195.73 | 186.78 | 205.59 | −45.33 | −43.58 | −42.91 | −43.48 | −44.84 | −45.77 | −45.89 | −45.82 | −45.96 | −45.77 |
| 215.44 | 205.59 | 226.29 | −43.32 | −44.99 | −47.60 | −48.72 | −48.72 | −49.04 | −49.25 | −49.48 | −51.50 | −53.40 |
| 237.14 | 226.29 | 249.08 | −50.42 | −50.13 | −48.73 | −47.26 | −45.82 | −44.82 | −45.04 | −45.68 | −45.84 | −46.06 |
| 261.02 | 249.08 | 274.16 | −44.53 | −42.34 | −43.71 | −45.64 | −52.17 | −51.88 | −52.16 | −53.56 | −54.39 | −52.28 |
| 287.30 | 274.16 | 301.76 | −51.09 | −51.48 | −51.42 | −51.18 | −52.27 | −52.81 | −53.33 | −54.72 | −57.56 | −55.19 |
| 316.23 | 301.76 | 332.15 | −45.86 | −48.39 | −49.62 | −50.13 | −48.88 | −48.75 | −48.68 | −48.85 | −50.03 | −51.47 |
| 348.07 | 332.15 | 365.59 | −49.77 | −51.99 | −57.36 | −59.37 | −57.18 | −55.77 | −56.04 | −55.13 | −56.44 | −59.31 |
| 383.12 | 365.59 | 402.41 | −46.43 | −51.44 | −51.62 | −52.34 | −52.02 | −51.35 | −51.10 | −51.37 | −52.31 | −53.44 |
| 421.70 | 402.41 | 442.93 | −51.60 | −52.31 | −52.70 | −53.51 | −53.47 | −51.57 | −50.44 | −51.42 | −54.00 | −59.06 |
| 464.16 | 442.93 | 487.53 | −61.33 | −63.18 | −61.96 | −62.29 | −62.61 | −59.15 | −57.81 | −58.62 | −60.19 | −62.69 |
| 510.90 | 487.53 | 536.62 | −49.54 | −51.70 | −51.15 | −52.16 | −53.23 | −50.98 | −49.53 | −50.32 | −52.83 | −54.36 |
| 562.34 | 536.62 | 590.65 | −57.42 | −57.30 | −54.26 | −53.53 | −56.09 | −55.31 | −54.58 | −55.63 | −57.54 | −57.05 |
| 618.97 | 590.65 | 650.13 | −58.49 | −58.44 | −57.32 | −58.47 | −59.70 | −57.39 | −57.01 | −57.73 | −59.58 | −60.72 |
| 681.29 | 650.13 | 715.59 | −50.25 | −53.30 | −53.77 | −54.42 | −55.93 | −55.63 | −55.66 | −55.22 | −56.83 | −57.24 |
| 749.89 | 715.59 | 787.65 | −56.16 | −55.33 | −53.51 | −54.91 | −58.49 | −56.44 | −55.11 | −55.61 | −56.55 | −57.51 |
| 825.40 | 787.65 | 866.96 | −61.05 | −56.32 | −53.36 | −55.17 | −62.00 | −54.92 | −52.47 | −55.31 | −59.61 | −59.34 |
| 908.52 | 866.96 | 954.26 | −62.16 | −59.27 | −56.98 | −59.43 | −64.27 | −58.84 | −57.79 | −60.06 | −61.92 | −62.14 |
| 1000.00 | 954.26 | 1050.35 | −57.68 | −54.66 | −52.37 | −55.61 | −58.92 | −55.12 | −53.52 | −53.12 | −56.07 | −57.87 |
| 1100.69 | 1050.35 | 1156.11 | −63.95 | −56.28 | −54.18 | −59.07 | −63.42 | −58.30 | −55.16 | −55.07 | −59.95 | −62.39 |
| 1211.53 | 1156.11 | 1272.52 | −62.35 | −61.01 | −57.68 | −59.10 | −62.69 | −61.35 | −59.03 | −58.35 | −61.18 | −62.62 |
| 1333.52 | 1272.52 | 1400.66 | −60.13 | −63.35 | −63.53 | −63.75 | −64.78 | −63.79 | −61.49 | −61.21 | −63.99 | −64.77 |
| 1467.80 | 1400.66 | 1541.70 | −68.03 | −68.57 | −67.34 | −66.64 | −67.56 | −65.69 | −63.45 | −63.95 | −65.95 | −67.58 |
| 1615.60 | 1541.70 | 1696.94 | −64.10 | −67.15 | −65.27 | −66.64 | −69.47 | −68.60 | −63.91 | −63.87 | −68.41 | −70.90 |
| 1778.28 | 1696.94 | 1867.81 | −71.67 | −71.66 | −70.18 | −70.71 | −72.84 | −71.93 | −69.55 | −69.16 | −70.89 | −72.41 |
| 1957.34 | 1867.81 | 2055.89 | −67.62 | −72.74 | −70.17 | −71.15 | −72.83 | −70.61 | −69.17 | −68.61 | −70.42 | −74.48 |
| 2154.43 | 2055.89 | 2262.90 | −68.07 | −70.53 | −71.38 | −72.02 | −74.47 | −73.30 | −71.23 | −71.45 | −74.15 | −76.83 |
| 2371.37 | 2262.90 | 2490.77 | −74.08 | −75.67 | −73.62 | −74.42 | −76.49 | −75.52 | −74.13 | −74.41 | −75.73 | −75.72 |
| 2610.16 | 2490.77 | 2741.57 | −72.24 | −76.23 | −72.79 | −72.34 | −72.64 | −73.54 | −72.52 | −75.30 | −77.50 |
| 2872.98 | 2741.57 | 3017.63 | −74.86 | −75.35 | −73.48 | −74.83 | −79.66 | −76.48 | −73.37 | −73.60 | −77.21 | −81.46 |
| 3162.28 | 3017.63 | 3321.49 | −76.47 | −80.10 | −75.62 | −76.45 | −81.68 | −80.04 | −76.31 | −76.07 | −79.96 | −81.64 |
| 3480.70 | 3321.49 | 3655.94 | −77.88 | −77.37 | −73.04 | −74.18 | −82.12 | −79.05 | −73.97 | −73.81 | −78.31 | −82.93 |
| 3831.19 | 3655.94 | 4024.08 | −81.63 | −80.37 | −75.73 | −76.84 | −82.63 | −78.92 | −74.53 | −74.52 | −79.50 | −85.55 |
| 4216.97 | 4024.08 | 4429.28 | −83.38 | −80.70 | −77.43 | −78.91 | −84.45 | −82.28 | −78.41 | −78.51 | −82.52 | −89.73 |
| 4641.59 | 4429.28 | 4875.28 | −86.53 | −81.81 | −77.42 | −78.39 | −83.80 | −82.40 | −77.60 | −77.68 | −82.86 | −90.42 |
| 5108.97 | 4875.28 | 5366.19 | −87.53 | −79.81 | −74.56 | −75.48 | −82.74 | −79.75 | −74.84 | −74.90 | −80.21 | −91.34 |
| 5623.41 | 5366.19 | 5906.54 | −91.32 | −81.99 | −77.89 | −79.65 | −84.14 | −81.25 | −78.53 | −78.83 | −83.14 | −94.06 |
| 6189.66 | 5906.54 | 6501.29 | −92.38 | −82.96 | −78.48 | −79.67 | −82.77 | −81.01 | −78.61 | −78.84 | −84.01 | −94.12 |
| 6812.92 | 6501.29 | 7155.93 | −95.54 | −82.55 | −77.41 | −78.65 | −85.63 | −82.41 | −78.50 | −78.67 | −83.61 | −93.76 |
| 7498.94 | 7155.93 | 7876.49 | −95.70 | −87.97 | −83.30 | −84.64 | −88.06 | −85.63 | −83.10 | −83.36 | −88.63 | −94.94 |
| 8254.04 | 7876.49 | 8669.61 | −97.73 | −87.44 | −82.76 | −84.24 | −86.99 | −85.07 | −84.12 | −84.62 | −89.25 | −96.53 |
| 9085.18 | 8669.61 | 9542.59 | −100.27 | −88.54 | −84.03 | −85.32 | −90.80 | −89.06 | −85.60 | −85.72 | −90.33 | −94.97 |
| 10000.00 | 9542.59 | 10503.47 | −103.20 | −90.73 | −86.16 | −87.00 | −91.89 | −90.81 | −87.24 | −87.36 | −91.58 | −94.05 |
| 11006.94 | 10503.47 | 11561.11 | −105.76 | −89.52 | −85.46 | −87.02 | −93.07 | −89.31 | −86.39 | −86.62 | −90.31 | −100.56 |
| 12115.28 | 11561.11 | 12725.25 | −107.69 | −94.04 | −89.20 | −91.34 | −95.25 | −93.36 | −91.97 | −92.28 | −95.79 | −100.86 |
| 13335.21 | 12725.25 | 14006.60 | −111.41 | −96.67 | −92.69 | −94.34 | −95.30 | −93.91 | −94.90 | −95.21 | −98.21 | −106.59 |
| 14677.99 | 14006.60 | 15416.99 | −114.02 | −101.79 | −97.88 | −99.13 | −103.06 | −102.46 | −101.01 | −101.32 | −104.70 | −107.27 |
| 16155.98 | 15416.99 | 16969.39 | −115.70 | −109.15 | −105.68 | −107.01 | −111.67 | −108.77 | −106.42 | −106.59 | −109.70 | −110.84 |
| 17782.79 | 16969.39 | 18678.11 | −116.69 | −115.71 | −114.20 | −114.48 | −116.06 | −116.37 | −116.25 | −116.28 | −116.53 | −108.96 |
| 19573.42 | 18678.11 | 20558.88 | −116.98 | −116.89 | −115.97 | −115.64 | −116.86 | −117.65 | −117.84 | −117.88 | −117.45 | −112.23 |
| 21544.35 | 20558.88 | 22629.04 | −114.33 | −114.31 | −113.90 | −113.71 | −114.29 | −114.60 | −114.66 | −114.69 | −114.53 | −113.65 |

TABLE 2-continued (section 15 of 28): Time-Frequency Spectral Analysis Results

| Bin Frequency (Hz) | Bin Start Frequency (Hz) | Bin Stop Frequency (Hz) | Average Signal Power Density per Bin Width (dBfs/Hz) vs Time and Frequency Time (min): | | | | | | | | | |
|---|---|---|---|---|---|---|---|---|---|---|---|---|
| | | | 35.24 | 35.73 | 36.23 | 36.73 | 37.22 | 37.72 | 38.21 | 38.71 | 39.21 | 39.70 |
| 1.00 | 1.00 | 1.05 | −91.38 | −92.04 | −90.16 | −90.83 | −90.29 | −89.67 | −86.91 | −81.49 | −82.08 | −89.92 |
| 1.10 | 1.05 | 1.16 | −91.38 | −92.04 | −90.16 | −90.83 | −90.29 | −89.67 | −86.91 | −81.49 | −82.08 | −89.92 |
| 1.21 | 1.16 | 1.27 | −90.95 | −91.53 | −89.96 | −90.49 | −89.87 | −89.10 | −86.52 | −81.36 | −81.95 | −90.00 |
| 1.33 | 1.27 | 1.40 | −89.53 | −89.89 | −89.23 | −89.34 | −88.46 | −87.28 | −85.19 | −80.82 | −81.46 | −90.35 |
| 1.47 | 1.40 | 1.54 | −89.02 | −89.55 | −88.93 | −89.15 | −88.08 | −86.82 | −85.06 | −80.79 | −81.36 | −90.03 |
| 1.62 | 1.54 | 1.70 | −88.00 | −88.84 | −88.29 | −88.73 | −87.29 | −85.90 | −84.77 | −80.72 | −81.15 | −89.36 |
| 1.78 | 1.70 | 1.87 | −87.81 | −88.45 | −87.60 | −88.43 | −87.30 | −85.91 | −85.46 | −80.32 | −80.54 | −88.48 |
| 1.96 | 1.87 | 2.06 | −87.72 | −88.15 | −87.06 | −87.37 | −86.74 | −85.76 | −85.38 | −80.13 | −80.23 | −88.26 |
| 2.15 | 2.06 | 2.26 | −87.71 | −87.83 | −86.48 | −85.61 | −85.49 | −85.35 | −84.43 | −80.10 | −80.12 | −88.51 |
| 2.37 | 2.26 | 2.49 | −87.77 | −88.00 | −86.18 | −84.20 | −83.83 | −84.55 | −83.52 | −80.07 | −80.63 | −87.76 |
| 2.61 | 2.49 | 2.74 | −87.26 | −87.66 | −85.47 | −83.58 | −82.26 | −83.69 | −82.49 | −80.72 | −81.16 | −85.72 |
| 2.87 | 2.74 | 3.02 | −86.69 | −85.45 | −84.92 | −82.98 | −81.26 | −82.67 | −81.64 | −80.00 | −80.57 | −84.19 |
| 3.16 | 3.02 | 3.32 | −86.70 | −84.89 | −84.75 | −83.21 | −81.85 | −82.67 | −81.56 | −79.59 | −80.49 | −84.01 |
| 3.48 | 3.32 | 3.66 | −85.68 | −84.19 | −84.19 | −83.07 | −81.81 | −81.96 | −80.66 | −79.46 | −81.06 | −84.45 |
| 3.83 | 3.66 | 4.02 | −82.00 | −80.95 | −82.32 | −82.35 | −80.86 | −81.01 | −77.90 | −77.33 | −80.75 | −83.84 |
| 4.22 | 4.02 | 4.43 | −82.01 | −81.16 | −82.47 | −81.20 | −79.96 | −80.91 | −78.60 | −77.56 | −80.36 | −84.06 |
| 4.64 | 4.43 | 4.88 | −85.33 | −84.57 | −83.70 | −81.76 | −80.63 | −82.35 | −81.45 | −78.81 | −80.00 | −84.20 |
| 5.11 | 4.88 | 5.37 | −85.21 | −84.07 | −83.28 | −82.15 | −80.13 | −81.90 | −80.74 | −79.11 | −80.23 | −84.04 |
| 5.62 | 5.37 | 5.91 | −82.29 | −82.80 | −82.30 | −82.33 | −81.05 | −80.09 | −78.65 | −76.29 | −77.10 | −81.23 |
| 6.19 | 5.91 | 6.50 | −81.32 | −81.03 | −80.56 | −81.54 | −80.25 | −78.94 | −78.70 | −75.47 | −75.86 | −80.03 |
| 6.81 | 6.50 | 7.16 | −82.57 | −82.26 | −81.42 | −81.92 | −79.91 | −79.36 | −78.79 | −77.12 | −77.49 | −79.84 |
| 7.50 | 7.16 | 7.88 | −81.29 | −81.20 | −81.26 | −80.24 | −78.70 | −77.59 | −76.13 | −75.40 | −76.60 | −79.35 |
| 8.25 | 7.88 | 8.67 | −75.37 | −76.21 | −78.91 | −77.67 | −77.18 | −76.02 | −74.03 | −72.57 | −73.66 | −76.39 |
| 9.09 | 8.67 | 9.54 | −75.09 | −75.59 | −76.31 | −75.58 | −74.61 | −73.80 | −71.64 | −70.81 | −72.34 | −74.27 |
| 10.00 | 9.54 | 10.50 | −76.09 | −74.22 | −73.29 | −71.47 | −71.69 | −73.03 | −71.95 | −70.11 | −71.14 | −73.08 |
| 11.01 | 10.50 | 11.56 | −68.24 | −63.76 | −62.72 | −63.27 | −62.54 | −62.11 | −62.29 | −62.78 | −63.81 | −63.85 |
| 12.12 | 11.56 | 12.73 | −67.21 | −66.53 | −68.65 | −68.42 | −67.83 | −66.34 | −65.29 | −64.93 | −67.15 | −67.97 |
| 13.34 | 12.73 | 14.01 | −60.26 | −62.06 | −65.54 | −65.13 | −64.18 | −63.11 | −62.66 | −62.84 | −64.75 | −66.16 |
| 14.68 | 14.01 | 15.42 | −70.68 | −67.98 | −67.25 | −67.78 | −66.57 | −63.59 | −62.74 | −62.73 | −63.37 | −65.53 |
| 16.16 | 15.42 | 16.97 | −66.52 | −65.70 | −64.69 | −64.20 | −63.57 | −62.30 | −61.30 | −60.23 | −60.93 | −63.29 |
| 17.78 | 16.97 | 18.68 | −54.59 | −56.15 | −59.42 | −59.17 | −58.51 | −58.31 | −57.84 | −58.08 | −60.31 | −62.37 |
| 19.57 | 18.68 | 20.56 | −67.32 | −63.59 | −61.61 | −61.05 | −59.70 | −58.01 | −56.78 | −57.13 | −61.33 | −63.85 |
| 21.54 | 20.56 | 22.63 | −61.06 | −61.01 | −60.70 | −60.31 | −58.76 | −57.31 | −56.22 | −56.97 | −59.46 | −62.75 |
| 23.71 | 22.63 | 24.91 | −65.05 | −63.52 | −62.52 | −62.55 | −62.50 | −62.20 | −61.13 | −60.68 | −61.63 | −62.80 |
| 26.10 | 24.91 | 27.42 | −66.13 | −64.36 | −63.20 | −62.80 | −62.66 | −62.64 | −61.48 | −60.78 | −61.57 | −63.21 |
| 28.73 | 27.42 | 30.18 | −60.67 | −59.08 | −59.36 | −58.69 | −58.56 | −57.59 | −56.04 | −56.32 | −58.90 | −61.02 |
| 31.62 | 30.18 | 33.21 | −62.58 | −60.28 | −58.91 | −58.26 | −57.29 | −54.30 | −51.79 | −45.54 | −45.78 | −60.02 |
| 34.81 | 33.21 | 36.56 | −58.63 | −52.60 | −51.07 | −54.24 | −56.52 | −55.33 | −49.68 | −51.54 | −44.47 |
| 38.31 | 36.56 | 40.24 | −53.69 | −49.34 | −48.09 | −51.48 | −54.71 | −53.94 | −51.18 | −48.04 | −49.91 | −44.70 |
| 42.17 | 40.24 | 44.29 | −45.57 | −45.63 | −45.46 | −44.07 | −44.11 | −43.55 | −39.69 | −37.12 | −35.25 | −36.79 |
| 46.42 | 44.29 | 48.75 | −55.45 | −49.72 | −53.10 | −51.11 | −48.56 | −49.30 | −47.86 | −48.50 | −47.39 | −46.61 |
| 51.09 | 48.75 | 53.66 | −60.04 | −45.13 | −49.25 | −50.30 | −46.52 | −47.68 | −46.96 | −49.21 | −43.17 | −41.98 |
| 56.23 | 53.66 | 59.07 | −53.97 | −47.40 | −43.28 | −44.39 | −46.20 | −47.22 | −42.56 | −39.32 | −38.14 | −41.26 |
| 61.90 | 59.07 | 65.01 | −48.11 | −46.70 | −47.04 | −48.09 | −45.60 | −44.05 | −43.96 | −42.94 | −43.38 | −46.22 |
| 68.13 | 65.01 | 71.56 | −44.94 | −43.82 | −43.08 | −43.16 | −43.40 | −42.37 | −42.02 | −39.95 | −40.21 | −43.94 |
| 74.99 | 71.56 | 78.76 | −38.61 | −38.42 | −39.49 | −39.43 | −40.05 | −40.51 | −41.52 | −39.80 | −40.78 | −38.85 |
| 82.54 | 78.76 | 86.70 | −39.06 | −39.85 | −39.70 | −39.31 | −39.25 | −39.21 | −37.67 | −36.05 | −37.48 | −43.76 |
| 90.85 | 86.70 | 95.43 | −53.29 | −51.42 | −50.41 | −46.04 | −46.04 | −50.55 | −47.60 | −43.76 | −40.84 | −42.56 |
| 100.00 | 95.43 | 105.03 | −44.76 | −43.41 | −43.53 | −43.83 | −43.61 | −42.82 | −41.62 | −41.66 | −43.44 | −46.37 |
| 110.07 | 105.03 | 115.61 | −52.51 | −49.11 | −47.75 | −48.01 | −46.81 | −44.00 | −42.77 | −38.23 | −36.60 | −39.41 |
| 121.15 | 115.61 | 127.25 | −47.53 | −46.83 | −47.87 | −47.91 | −45.79 | −46.14 | −47.52 | −47.29 | −48.00 | −51.89 |
| 133.35 | 127.25 | 140.07 | −45.99 | −48.72 | −48.98 | −48.72 | −48.80 | −48.48 | −46.90 | −42.94 | −43.08 | −47.58 |
| 146.78 | 140.07 | 154.17 | −43.44 | −42.71 | −45.52 | −45.70 | −44.61 | −45.12 | −47.25 | −47.65 | −49.93 | −45.30 |

(section 16 of 28): Time-Frequency Spectral Analysis Results

| Bin Frequency (Hz) | Bin Start Frequency (Hz) | Bin Stop Frequency (Hz) | Average Signal Power Density per Bin Width (dBfs/Hz) vs Time and Frequency Time (min): | | | | | | | | | |
|---|---|---|---|---|---|---|---|---|---|---|---|---|
| | | | 35.24 | 35.73 | 36.23 | 36.73 | 37.22 | 37.72 | 38.21 | 38.71 | 39.21 | 39.70 |
| 161.56 | 154.17 | 169.69 | −44.57 | −44.46 | −44.28 | −43.94 | −43.47 | −42.62 | −41.33 | −40.97 | −43.16 | −47.44 |
| 177.83 | 169.69 | 186.78 | −50.13 | −53.32 | −52.84 | −51.27 | −48.67 | −48.69 | −44.94 | −45.14 | −49.09 | −45.85 |
| 195.73 | 186.78 | 205.59 | −46.32 | −45.06 | −45.48 | −46.89 | −45.86 | −45.09 | −44.71 | −45.21 | −47.91 | −45.72 |
| 215.44 | 205.59 | 226.29 | −50.70 | −48.35 | −48.42 | −46.89 | −46.43 | −46.22 | −44.36 | −40.99 | −39.10 | −40.34 |
| 237.14 | 226.29 | 249.08 | −45.83 | −46.59 | −46.58 | −46.13 | −45.97 | −46.27 | −46.39 | −46.85 | −49.48 | −55.82 |
| 261.02 | 249.08 | 274.16 | −52.41 | −53.71 | −52.94 | −52.88 | −52.75 | −52.78 | −51.54 | −49.97 | −49.52 | −48.23 |
| 287.30 | 274.16 | 301.76 | −53.97 | −53.31 | −52.39 | −50.50 | −46.96 | −46.29 | −48.78 | −46.27 | −43.24 | −43.41 |
| 316.23 | 301.76 | 332.15 | −51.00 | −50.64 | −50.85 | −50.04 | −49.31 | −49.28 | −47.52 | −46.47 | −46.38 | −47.87 |
| 348.07 | 332.15 | 365.59 | −57.94 | −55.11 | −54.29 | −54.71 | −54.22 | −51.52 | −48.63 | −48.14 | −50.17 | −50.90 |
| 383.12 | 365.59 | 402.41 | −53.97 | −52.31 | −50.44 | −49.88 | −50.81 | −49.80 | −49.01 | −47.89 | −49.50 | −51.09 |

TABLE 2-continued

| | | | | | | | | | | |
|---|---|---|---|---|---|---|---|---|---|---|
| 421.70 | 402.41 | 442.93 | −56.87 | −52.95 | −45.81 | −43.65 | −44.25 | −45.53 | −47.34 | −47.95 | −49.30 | −50.90 |
| 464.16 | 442.93 | 487.53 | −60.51 | −56.37 | −53.61 | −53.66 | −54.06 | −53.32 | −53.93 | −56.07 | −56.84 | −59.12 |
| 510.90 | 487.53 | 536.62 | −53.52 | −50.52 | −47.32 | −44.13 | −44.73 | −44.40 | −43.99 | −47.39 | −50.39 | −53.09 |
| 562.34 | 536.62 | 590.65 | −57.02 | −56.01 | −55.42 | −55.86 | −49.54 | −48.46 | −47.08 | −47.13 | −49.27 | −48.66 |
| 618.97 | 590.65 | 650.13 | −60.00 | −58.47 | −58.17 | −56.34 | −51.24 | −48.81 | −47.15 | −47.79 | −50.05 | −50.80 |
| 681.29 | 650.13 | 715.59 | −56.26 | −54.21 | −54.72 | −56.44 | −53.29 | −49.51 | −42.53 | −41.65 | −45.94 | −50.99 |
| 749.89 | 715.59 | 787.65 | −57.60 | −56.69 | −55.22 | −54.62 | −55.07 | −54.08 | −51.68 | −51.68 | −57.03 | −58.53 |
| 825.40 | 787.65 | 866.96 | −57.22 | −57.51 | −58.29 | −58.68 | −59.69 | −55.69 | −47.91 | −49.10 | −58.62 | −63.23 |
| 908.52 | 866.96 | 954.26 | −59.81 | −57.47 | −52.94 | −51.69 | −52.84 | −51.73 | −52.11 | −56.89 | −53.73 | −54.13 |
| 1000.00 | 954.26 | 1050.35 | −57.17 | −55.24 | −53.30 | −51.87 | −52.81 | −51.71 | −51.53 | −50.41 | −57.18 | −59.10 |
| 1100.69 | 1050.35 | 1156.11 | −61.17 | −58.17 | −57.57 | −56.10 | −55.63 | −54.43 | −53.95 | −57.13 | −60.29 | −62.72 |
| 1211.53 | 1156.11 | 1272.52 | −61.29 | −60.06 | −58.32 | −57.54 | −56.50 | −55.70 | −55.13 | −55.80 | −59.19 | −61.50 |
| 1333.52 | 1272.52 | 1400.66 | −63.94 | −63.33 | −59.53 | −58.24 | −58.90 | −57.80 | −54.59 | −53.81 | −58.98 | −63.22 |
| 1467.80 | 1400.66 | 1541.70 | −66.40 | −65.11 | −62.69 | −61.81 | −62.92 | −59.93 | −59.19 | −64.06 | −66.06 | −65.89 |
| 1615.60 | 1541.70 | 1696.94 | −69.52 | −67.02 | −64.31 | −62.95 | −64.11 | −62.51 | −59.26 | −60.60 | −64.73 | −66.16 |
| 1778.28 | 1696.94 | 1867.81 | −72.63 | −69.55 | −63.04 | −61.47 | −61.66 | −62.35 | −63.33 | −65.10 | −67.12 | −66.55 |
| 1957.34 | 1867.81 | 2055.89 | −71.92 | −67.84 | −66.15 | −67.31 | −68.87 | −69.25 | −65.83 | −63.48 | −66.18 | −67.31 |
| 2154.43 | 2055.89 | 2262.90 | −75.58 | −72.04 | −70.32 | −71.18 | −72.16 | −69.32 | −68.85 | −71.18 | −71.12 | −71.56 |
| 2371.37 | 2262.90 | 2490.77 | −76.07 | −74.35 | −74.08 | −75.58 | −75.43 | −71.64 | −69.64 | −70.92 | −74.54 | −72.72 |
| 2610.16 | 2490.77 | 2741.57 | −76.49 | −74.29 | −74.00 | −75.66 | −76.45 | −75.52 | −73.27 | −73.75 | −76.30 | −71.72 |
| 2872.98 | 2741.57 | 3017.63 | −80.79 | −75.11 | −74.88 | −78.96 | −78.51 | −75.69 | −74.34 | −75.47 | −76.20 | −74.66 |
| 3162.28 | 3017.63 | 3321.49 | −79.68 | −71.84 | −70.75 | −78.99 | −78.59 | −76.67 | −74.90 | −74.68 | −72.86 | −72.77 |
| 3480.70 | 3321.49 | 3655.94 | −79.93 | −73.86 | −72.83 | −79.83 | −78.53 | −76.20 | −75.47 | −75.99 | −74.44 | −75.55 |
| 3831.19 | 3655.94 | 4024.08 | −81.37 | −74.63 | −74.85 | −81.18 | −81.06 | −78.74 | −76.57 | −76.27 | −76.47 | −76.51 |
| 4216.97 | 4024.08 | 4429.28 | −86.28 | −77.91 | −77.93 | −83.08 | −82.92 | −80.64 | −78.80 | −80.29 | −81.76 | −81.63 |
| 4641.59 | 4429.28 | 4875.28 | −85.69 | −77.35 | −77.27 | −83.76 | −83.96 | −82.21 | −80.14 | −80.35 | −81.68 | −81.56 |
| 5108.97 | 4875.28 | 5366.19 | −88.20 | −77.84 | −77.93 | −84.97 | −85.01 | −83.87 | −82.79 | −82.65 | −83.67 | −83.09 |
| 5623.41 | 5366.19 | 5906.54 | −89.05 | −78.17 | −78.42 | −85.34 | −85.30 | −84.54 | −83.60 | −83.33 | −82.98 | −83.54 |
| 6189.66 | 5906.54 | 6501.29 | −88.49 | −78.72 | −79.38 | −85.27 | −85.26 | −84.54 | −83.81 | −83.72 | −83.13 | −83.51 |
| 6812.92 | 6501.29 | 7155.93 | −88.99 | −79.67 | −79.77 | −85.42 | −85.28 | −84.65 | −84.11 | −84.19 | −84.13 | −84.26 |
| 7498.94 | 7155.93 | 7876.49 | −90.59 | −82.61 | −82.06 | −87.92 | −87.90 | −87.02 | −86.15 | −86.09 | −85.10 | −85.60 |
| 8254.04 | 7876.49 | 8669.61 | −91.61 | −84.12 | −83.68 | −88.41 | −88.55 | −87.85 | −87.08 | −86.94 | −82.57 | −83.15 |
| 9085.18 | 8669.61 | 9542.59 | −88.71 | −82.48 | −82.47 | −88.13 | −87.74 | −86.69 | −86.47 | −86.01 | −84.57 | −86.35 |
| 10000.00 | 9542.59 | 10503.47 | −90.01 | −83.93 | −83.56 | −89.66 | −89.14 | −88.14 | −88.10 | −88.18 | −85.00 | −85.72 |
| 11006.94 | 10503.47 | 11561.11 | −95.62 | −90.00 | −89.45 | −91.68 | −91.69 | −90.87 | −90.48 | −90.57 | −90.02 | −90.93 |
| 12115.28 | 11561.11 | 12725.25 | −96.69 | −90.94 | −90.45 | −93.05 | −92.34 | −91.39 | −91.62 | −91.97 | −91.42 | −92.05 |
| 13335.21 | 12725.25 | 14006.60 | −99.86 | −93.92 | −92.66 | −93.47 | −93.40 | −93.13 | −92.61 | −92.60 | −92.70 | −92.80 |
| 14677.99 | 14006.60 | 15416.99 | −100.65 | −95.20 | −94.14 | −95.47 | −95.36 | −94.82 | −94.39 | −94.47 | −94.46 | −94.96 |
| 16155.98 | 15416.99 | 16969.39 | −103.20 | −97.71 | −96.47 | −97.53 | −97.67 | −97.37 | −97.04 | −97.03 | −96.58 | −96.97 |
| 17782.79 | 16969.39 | 18678.11 | −102.24 | −95.28 | −94.70 | −98.25 | −98.20 | −97.59 | −97.24 | −97.42 | −96.56 | −96.96 |
| 19573.42 | 18678.11 | 20558.88 | −106.47 | −100.55 | −100.08 | −102.09 | −102.06 | −101.58 | −101.37 | −101.50 | −100.84 | −101.29 |
| 21544.35 | 20558.88 | 22629.04 | −112.38 | −109.31 | −109.07 | −110.61 | −110.52 | −110.31 | −110.19 | −109.86 | −109.73 | −110.44 |

(section 17 of 28): Time-Frequency Spectral Analysis Results

| Bin Frequency (Hz) | Bin Start Frequency (Hz) | Bin Stop Frequency (Hz) | Average Signal Power Density per Bin Width (dBfs/Hz) vs Time and Frequency Time (min): | | | | | | | | | |
|---|---|---|---|---|---|---|---|---|---|---|---|
| | | | 40.20 | 40.70 | 41.19 | 41.69 | 42.18 | 42.68 | 43.18 | 43.67 | 44.17 | 44.67 |
| 1.00 | 1.00 | 1.05 | −91.46 | −91.48 | −91.08 | −92.16 | −87.93 | −85.26 | −83.46 | −84.00 | −83.74 | −79.52 |
| 1.10 | 1.05 | 1.16 | −91.46 | −91.48 | −91.08 | −92.16 | −87.93 | −85.26 | −83.46 | −84.00 | −83.74 | −79.52 |
| 1.21 | 1.16 | 1.27 | −91.57 | −91.41 | −91.07 | −92.14 | −88.06 | −85.32 | −83.27 | −83.96 | −83.83 | −79.82 |
| 1.33 | 1.27 | 1.40 | −92.04 | −91.13 | −91.06 | −92.05 | −88.66 | −85.57 | −82.54 | −83.78 | −84.24 | −81.37 |
| 1.47 | 1.40 | 1.54 | −91.84 | −90.84 | −90.78 | −91.96 | −88.34 | −85.22 | −82.24 | −83.19 | −84.22 | −81.61 |
| 1.62 | 1.54 | 1.70 | −91.40 | −90.20 | −90.19 | −91.76 | −87.67 | −84.50 | −81.59 | −82.04 | −84.17 | −82.26 |
| 1.78 | 1.70 | 1.87 | −90.61 | −89.27 | −88.89 | −89.24 | −85.26 | −81.20 | −79.42 | −80.36 | −82.73 | −82.87 |
| 1.96 | 1.87 | 2.06 | −89.80 | −88.53 | −88.28 | −88.20 | −84.08 | −79.85 | −78.05 | −79.37 | −81.80 | −83.34 |
| 2.15 | 2.06 | 2.26 | −88.73 | −87.74 | −88.02 | −87.71 | −83.22 | −79.07 | −76.84 | −78.59 | −81.02 | −83.78 |
| 2.37 | 2.26 | 2.49 | −87.51 | −87.38 | −88.50 | −88.91 | −83.26 | −80.32 | −77.78 | −79.24 | −81.64 | −84.02 |
| 2.61 | 2.49 | 2.74 | −86.46 | −86.53 | −87.79 | −87.82 | −84.20 | −81.77 | −79.16 | −79.89 | −82.43 | −84.43 |
| 2.87 | 2.74 | 3.02 | −85.20 | −85.88 | −87.52 | −86.54 | −82.73 | −81.26 | −78.19 | −78.21 | −81.19 | −84.65 |
| 3.16 | 3.02 | 3.32 | −84.78 | −85.25 | −86.79 | −85.50 | −81.18 | −79.47 | −77.22 | −77.10 | −80.39 | −85.25 |
| 3.48 | 3.32 | 3.66 | −84.07 | −84.69 | −85.87 | −84.82 | −82.50 | −79.87 | −76.73 | −77.55 | −81.08 | −85.69 |
| 3.83 | 3.66 | 4.02 | −83.21 | −83.71 | −84.82 | −84.11 | −81.04 | −78.10 | −75.45 | −76.24 | −79.54 | −84.99 |
| 4.22 | 4.02 | 4.43 | −82.61 | −82.60 | −84.20 | −84.20 | −78.23 | −74.84 | −72.40 | −73.27 | −76.90 | −84.95 |
| 4.64 | 4.43 | 4.88 | −83.85 | −84.23 | −85.15 | −84.69 | −80.96 | −77.61 | −74.66 | −75.53 | −79.37 | −85.21 |
| 5.11 | 4.88 | 5.37 | −82.33 | −82.72 | −82.36 | −82.50 | −80.47 | −78.01 | −75.07 | −75.56 | −78.03 | −79.33 |
| 5.62 | 5.37 | 5.91 | −81.62 | −83.20 | −82.14 | −81.80 | −81.00 | −78.09 | −75.43 | −76.25 | −78.61 | −79.16 |
| 6.19 | 5.91 | 6.50 | −80.82 | −83.01 | −82.75 | −81.49 | −78.21 | −75.50 | −73.86 | −74.48 | −76.62 | −78.18 |
| 6.81 | 6.50 | 7.16 | −80.64 | −81.21 | −81.18 | −81.63 | −80.19 | −77.30 | −74.22 | −74.58 | −77.73 | −79.03 |
| 7.50 | 7.16 | 7.88 | −81.08 | −80.81 | −79.24 | −79.65 | −78.08 | −75.66 | −72.75 | −72.70 | −75.88 | −78.30 |
| 8.25 | 7.88 | 8.67 | −77.27 | −77.24 | −77.59 | −77.94 | −75.07 | −73.07 | −71.58 | −71.77 | −74.40 | −77.73 |
| 9.09 | 8.67 | 9.54 | −74.72 | −76.64 | −74.41 | −73.93 | −74.58 | −71.94 | −69.82 | −70.86 | −74.07 | −75.50 |
| 10.00 | 9.54 | 10.50 | −72.76 | −72.96 | −72.42 | −73.01 | −73.87 | −71.87 | −69.37 | −69.65 | −72.04 | −71.68 |
| 11.01 | 10.50 | 11.56 | −63.22 | −63.60 | −63.44 | −64.26 | −64.88 | −63.60 | −62.79 | −62.46 | −62.87 | −62.69 |
| 12.12 | 11.56 | 12.73 | −67.45 | −67.18 | −65.81 | −67.19 | −72.80 | −70.65 | −65.43 | −64.70 | −65.55 | −65.00 |
| 13.34 | 12.73 | 14.01 | −64.57 | −62.76 | −62.41 | −64.34 | −68.87 | −66.70 | −63.71 | −62.48 | −62.87 | −63.53 |
| 14.68 | 14.01 | 15.42 | −66.21 | −65.45 | −61.84 | −63.65 | −64.65 | −63.65 | −63.02 | −62.82 | −63.44 | −64.98 |

TABLE 2-continued

| | | | | | | | | | | | |
|---|---|---|---|---|---|---|---|---|---|---|---|
| 16.16 | 15.42 | 16.97 | −63.62 | −62.98 | −61.63 | −63.02 | −64.97 | −63.60 | −61.58 | −60.87 | −61.99 | −63.01 |
| 17.78 | 16.97 | 18.68 | −61.27 | −60.25 | −58.81 | −59.66 | −63.58 | −63.04 | −62.33 | −61.14 | −59.64 | −60.41 |
| 19.57 | 18.68 | 20.56 | −60.28 | −58.70 | −57.31 | −58.98 | −67.72 | −64.77 | −61.82 | −58.94 | −57.94 | −59.46 |
| 21.54 | 20.56 | 22.63 | −60.96 | −59.29 | −58.74 | −60.73 | −65.48 | −64.12 | −61.65 | −58.02 | −57.31 | −58.74 |
| 23.71 | 22.63 | 24.91 | −64.32 | −64.96 | −63.17 | −65.23 | −66.27 | −65.01 | −63.19 | −61.27 | −62.08 | −62.96 |
| 26.10 | 24.91 | 27.42 | −63.85 | −64.27 | −63.93 | −65.67 | −68.31 | −65.66 | −62.92 | −61.47 | −61.50 | −61.56 |
| 28.73 | 27.42 | 30.18 | −59.08 | −57.22 | −56.28 | −58.49 | −65.79 | −62.95 | −60.19 | −57.66 | −56.03 | −56.20 |
| 31.62 | 30.18 | 33.21 | −58.78 | −57.52 | −55.93 | −57.81 | −69.18 | −63.11 | −59.67 | −56.95 | −55.94 | −56.71 |
| 34.81 | 33.21 | 36.56 | −48.44 | −58.30 | −59.00 | −57.93 | −56.36 | −53.76 | −52.57 | −52.21 | −53.88 | −53.58 |
| 38.31 | 36.56 | 40.24 | −47.52 | −57.72 | −58.84 | −57.96 | −56.47 | −54.60 | −53.04 | −51.81 | −53.03 | −51.89 |
| 42.17 | 40.24 | 44.29 | −44.32 | −42.92 | −45.45 | −47.29 | −52.53 | −53.33 | −50.61 | −51.29 | −56.06 | −58.44 |
| 46.42 | 44.29 | 48.75 | −49.55 | −52.17 | −53.52 | −54.10 | −57.40 | −53.07 | −47.35 | −46.60 | −50.84 | −61.26 |
| 51.09 | 48.75 | 53.66 | −47.25 | −58.34 | −49.08 | −49.32 | −54.75 | −49.10 | −42.56 | −41.24 | −44.60 | −60.61 |
| 56.23 | 53.66 | 59.07 | −46.55 | −43.47 | −41.89 | −44.01 | −45.82 | −42.34 | −39.78 | −39.91 | −42.46 | −49.87 |
| 61.90 | 59.07 | 65.01 | −49.62 | −49.57 | −49.86 | −46.79 | −42.89 | −42.08 | −42.12 | −42.23 | −44.79 | −56.31 |
| 68.13 | 65.01 | 71.56 | −44.92 | −44.77 | −44.63 | −44.98 | −42.16 | −40.67 | −39.69 | −39.53 | −42.94 | −52.38 |
| 74.99 | 71.56 | 78.76 | −43.10 | −43.07 | −42.61 | −42.25 | −38.64 | −38.65 | −37.90 | −36.23 | −38.77 | −49.55 |
| 82.54 | 78.76 | 86.70 | −42.80 | −42.20 | −46.64 | −53.35 | −49.74 | −46.03 | −41.92 | −42.44 | −48.95 | −57.49 |
| 90.85 | 86.70 | 95.43 | −53.21 | −50.68 | −52.62 | −53.47 | −45.59 | −43.93 | −42.35 | −42.63 | −46.54 | −58.58 |
| 100.00 | 95.43 | 105.03 | −49.01 | −44.91 | −44.66 | −50.84 | −42.83 | −40.70 | −38.99 | −39.42 | −44.22 | −48.34 |
| 110.07 | 105.03 | 115.61 | −47.45 | −43.87 | −42.62 | −44.77 | −45.21 | −42.89 | −41.11 | −41.51 | −45.06 | −47.28 |
| 121.15 | 115.61 | 127.25 | −53.70 | −53.91 | −52.64 | −50.87 | −47.07 | −43.33 | −41.27 | −42.80 | −48.94 | −55.19 |
| 133.35 | 127.25 | 140.07 | −47.58 | −48.25 | −49.51 | −47.71 | −45.23 | −42.77 | −40.82 | −41.83 | −46.33 | −52.08 |
| 146.78 | 140.07 | 154.17 | −44.51 | −44.11 | −43.61 | −44.73 | −45.19 | −44.37 | −42.34 | −41.15 | −42.79 | −46.39 |

(section 18 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | |
|---|---|---|---|---|---|---|---|---|---|---|---|
| (Hz) | (Hz) | (Hz) | 40.20 | 40.70 | 41.19 | 41.69 | 42.18 | 42.68 | 43.18 | 43.67 | 44.17 | 44.67 |
| 161.56 | 154.17 | 169.69 | −45.50 | −42.56 | −41.43 | −43.10 | −48.55 | −48.46 | −44.91 | −42.83 | −40.07 | −41.06 |
| 177.83 | 169.69 | 186.78 | −44.89 | −43.86 | −42.37 | −42.33 | −41.02 | −41.47 | −42.40 | −42.91 | −46.22 | −53.77 |
| 195.73 | 186.78 | 205.59 | −43.43 | −41.66 | −40.84 | −44.33 | −45.86 | −43.72 | −41.80 | −41.42 | −45.48 | −61.93 |
| 215.44 | 205.59 | 226.29 | −43.36 | −42.45 | −42.03 | −43.69 | −44.41 | −43.49 | −41.40 | −40.76 | −41.91 | −46.44 |
| 237.14 | 226.29 | 249.08 | −56.15 | −53.55 | −53.00 | −53.57 | −48.44 | −46.56 | −47.03 | −48.27 | −49.34 | −54.30 |
| 261.02 | 249.08 | 274.16 | −46.93 | −48.86 | −47.08 | −46.08 | −49.39 | −49.13 | −46.96 | −46.13 | −49.07 | −52.44 |
| 287.30 | 274.16 | 301.76 | −44.81 | −48.35 | −45.76 | −45.01 | −47.15 | −45.29 | −44.14 | −43.75 | −46.31 | −59.81 |
| 316.23 | 301.76 | 332.15 | −48.54 | −46.64 | −44.35 | −46.36 | −52.73 | −49.80 | −48.58 | −49.11 | −54.66 | −53.11 |
| 348.10 | 332.15 | 365.59 | −46.54 | −46.78 | −51.77 | −49.38 | −44.89 | −42.57 | −41.45 | −42.37 | −45.83 | −55.53 |
| 383.12 | 365.59 | 402.41 | −49.58 | −49.33 | −48.48 | −50.62 | −51.89 | −46.02 | −42.57 | −43.85 | −51.23 | −52.70 |
| 421.70 | 402.41 | 442.93 | −47.30 | −46.80 | −52.66 | −51.67 | −48.74 | −46.39 | −45.81 | −47.27 | −51.08 | −58.24 |
| 464.16 | 442.93 | 487.53 | −56.33 | −55.48 | −59.15 | −58.27 | −52.80 | −50.12 | −50.44 | −53.16 | −57.62 | −67.51 |
| 510.90 | 487.53 | 536.62 | −49.00 | −43.39 | −41.58 | −44.70 | −50.44 | −48.14 | −47.39 | −47.36 | −50.50 | −59.03 |
| 562.34 | 536.62 | 590.65 | −49.88 | −54.23 | −54.22 | −54.61 | −56.19 | −49.13 | −46.17 | −46.64 | −49.19 | −59.26 |
| 618.97 | 590.65 | 650.13 | −53.75 | −55.66 | −54.70 | −57.32 | −61.03 | −51.81 | −50.36 | −53.10 | −55.45 | −66.09 |
| 681.29 | 650.13 | 715.59 | −50.08 | −49.08 | −49.25 | −50.62 | −52.84 | −50.72 | −48.01 | −47.97 | −52.01 | −58.00 |
| 749.89 | 715.59 | 787.65 | −54.92 | −53.74 | −54.08 | −56.84 | −55.67 | −52.87 | −51.80 | −52.09 | −56.59 | −61.09 |
| 825.40 | 787.65 | 866.96 | −60.73 | −57.47 | −57.78 | −58.15 | −56.68 | −55.50 | −55.68 | −56.34 | −59.75 | −68.13 |
| 908.52 | 866.96 | 954.26 | −55.74 | −52.51 | −53.19 | −55.51 | −52.49 | −49.78 | −49.92 | −51.76 | −55.48 | −66.16 |
| 1000.00 | 954.26 | 1050.35 | −57.59 | −52.42 | −50.73 | −53.46 | −58.14 | −57.35 | −55.15 | −54.35 | −58.61 | −61.90 |
| 1100.69 | 1050.35 | 1156.11 | −56.14 | −53.93 | −53.75 | −57.59 | −56.51 | −55.50 | −56.83 | −55.66 | −60.74 | −71.69 |
| 1211.53 | 1156.11 | 1272.52 | −61.63 | −62.36 | −60.74 | −61.25 | −63.86 | −58.50 | −57.59 | −60.03 | −63.66 | −63.95 |
| 1333.52 | 1272.52 | 1400.66 | −60.49 | −58.22 | −57.98 | −60.89 | −64.44 | −63.14 | −60.84 | −59.54 | −62.93 | −62.92 |
| 1467.80 | 1400.66 | 1541.70 | −64.69 | −61.48 | −59.96 | −62.69 | −69.84 | −67.41 | −67.72 | −68.68 | −70.37 | −73.28 |
| 1615.60 | 1541.70 | 1696.94 | −63.74 | −60.85 | −59.63 | −62.12 | −69.54 | −69.95 | −69.65 | −71.50 | −66.48 |
| 1778.28 | 1696.94 | 1867.81 | −63.60 | −61.14 | −61.85 | −65.14 | −68.42 | −67.71 | −68.40 | −68.53 | −71.56 | −72.27 |
| 1957.34 | 1867.81 | 2055.89 | −66.50 | −63.32 | −63.01 | −67.33 | −75.42 | −74.18 | −72.37 | −71.04 | −74.40 | −72.77 |
| 2154.43 | 2055.89 | 2262.90 | −68.64 | −67.82 | −67.47 | −69.27 | −72.41 | −72.99 | −73.39 | −73.88 | −74.91 | −73.94 |
| 2371.37 | 2262.90 | 2490.77 | −67.95 | −67.34 | −68.49 | −70.86 | −74.74 | −73.20 | −72.42 | −74.30 | −77.18 | −73.72 |
| 2610.16 | 2490.77 | 2741.57 | −68.15 | −64.65 | −67.29 | −70.29 | −75.96 | −73.56 | −72.71 | −73.97 | −77.76 | −75.88 |
| 2872.98 | 2741.57 | 3017.63 | −70.82 | −70.52 | −71.61 | −74.22 | −77.16 | −76.80 | −75.17 | −75.56 | −79.47 | −76.28 |
| 3162.28 | 3017.63 | 3321.49 | −73.41 | −70.51 | −70.84 | −75.24 | −76.85 | −75.35 | −74.92 | −75.74 | −79.52 | −78.89 |
| 3480.70 | 3321.49 | 3655.94 | −74.87 | −72.24 | −72.88 | −76.69 | −80.12 | −77.83 | −77.31 | −78.74 | −82.97 | −82.00 |
| 3831.19 | 3655.94 | 4024.08 | −74.77 | −73.47 | −74.53 | −78.31 | −80.78 | −77.04 | −77.91 | −77.36 | −82.65 | −81.51 |
| 4216.97 | 4024.08 | 4429.28 | −78.99 | −77.37 | −78.00 | −81.16 | −83.19 | −80.57 | −79.06 | −80.54 | −84.70 | −84.00 |
| 4641.59 | 4429.28 | 4875.28 | −80.08 | −78.27 | −79.21 | −82.71 | −84.79 | −83.43 | −82.87 | −83.63 | −85.88 | −85.38 |
| 5108.97 | 4875.28 | 5366.19 | −81.09 | −79.55 | −80.32 | −84.02 | −85.86 | −84.42 | −83.33 | −83.15 | −86.35 | −86.45 |
| 5623.41 | 5366.19 | 5906.54 | −84.62 | −84.25 | −84.59 | −85.70 | −86.14 | −84.70 | −83.60 | −84.10 | −87.05 | −88.31 |
| 6189.66 | 5906.54 | 6501.29 | −84.05 | −82.90 | −83.30 | −85.42 | −85.99 | −84.56 | −83.69 | −84.39 | −86.81 | −88.39 |
| 6812.92 | 6501.29 | 7155.93 | −84.93 | −83.67 | −83.93 | −86.05 | −86.49 | −85.55 | −84.70 | −84.87 | −86.85 | −89.03 |
| 7498.94 | 7155.93 | 7876.49 | −87.90 | −87.01 | −87.25 | −88.82 | −88.86 | −87.19 | −86.66 | −87.38 | −89.33 | −90.41 |
| 8254.04 | 7876.49 | 8669.61 | −88.44 | −87.47 | −87.80 | −89.45 | −89.58 | −87.80 | −87.99 | −87.99 | −89.10 | −92.15 |
| 9085.18 | 8669.61 | 9542.59 | −89.43 | −85.25 | −85.59 | −90.06 | −90.08 | −88.63 | −87.72 | −88.23 | −90.71 | −93.71 |
| 10000.00 | 9542.59 | 10503.47 | −91.08 | −89.96 | −89.81 | −91.78 | −91.84 | −89.94 | −88.61 | −89.02 | −92.04 | −93.56 |
| 11006.94 | 10503.47 | 11561.11 | −92.48 | −91.88 | −92.03 | −92.95 | −91.42 | −89.27 | −87.41 | −87.84 | −91.90 | −93.08 |
| 12115.28 | 11561.11 | 12725.25 | −93.62 | −93.34 | −93.49 | −93.59 | −89.96 | −86.82 | −84.61 | −85.18 | −90.29 | −92.89 |
| 13335.21 | 12725.25 | 14006.60 | −93.67 | −93.43 | −93.50 | −93.42 | −89.85 | −86.72 | −84.50 | −85.11 | −90.31 | −94.46 |

TABLE 2-continued

| | | | | | | | | | | |
|---|---|---|---|---|---|---|---|---|---|---|
| 14677.99 | 14006.60 | 15416.99 | −95.76 | −95.39 | −95.40 | −94.75 | −90.15 | −86.74 | −84.41 | −85.06 | −90.62 | −97.26 |
| 16155.98 | 15416.99 | 16969.39 | −97.92 | −97.50 | −97.51 | −97.99 | −96.16 | −93.91 | −91.99 | −92.44 | −96.76 | −101.97 |
| 17782.79 | 16969.39 | 18678.11 | −98.81 | −98.30 | −98.33 | −99.39 | −99.70 | −99.77 | −99.30 | −98.96 | −100.37 | −104.22 |
| 19573.42 | 18678.11 | 20558.88 | −102.50 | −102.14 | −102.14 | −103.02 | −103.33 | −103.40 | −102.98 | −102.65 | −103.91 | −106.74 |
| 21544.35 | 20558.88 | 22629.04 | −110.82 | −110.61 | −110.65 | −111.16 | −111.39 | −111.44 | −111.16 | −110.93 | −111.40 | −111.72 |

(section 19 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | | |
|---|---|---|---|---|---|---|---|---|---|---|---|
| (Hz) | (Hz) | (Hz) | 45.16 | 45.66 | 46.15 | 46.65 | 47.15 | 47.64 | 48.14 | 48.64 | 49.13 | 49.63 |
| 1.00 | 1.00 | 1.05 | −80.79 | −91.01 | −89.33 | −89.96 | −89.54 | −88.95 | −87.57 | −85.98 | −87.64 | −93.41 |
| 1.10 | 1.05 | 1.16 | −80.79 | −91.01 | −89.33 | −89.96 | −89.54 | −88.95 | −87.57 | −85.98 | −87.64 | −93.41 |
| 1.21 | 1.16 | 1.27 | −81.11 | −90.81 | −89.33 | −89.81 | −89.50 | −88.83 | −87.31 | −85.69 | −87.40 | −93.38 |
| 1.33 | 1.27 | 1.40 | −82.83 | −90.06 | −88.44 | −89.21 | −89.35 | −88.37 | −86.39 | −84.65 | −86.52 | −93.26 |
| 1.47 | 1.40 | 1.54 | −83.27 | −90.26 | −88.95 | −89.74 | −89.73 | −88.66 | −86.65 | −85.14 | −87.09 | −93.70 |
| 1.62 | 1.54 | 1.70 | −84.55 | −90.76 | −90.46 | −91.35 | −90.83 | −89.47 | −87.34 | −86.61 | −88.87 | −94.99 |
| 1.78 | 1.70 | 1.87 | −84.70 | −91.23 | −91.16 | −91.89 | −91.15 | −89.18 | −88.04 | −87.72 | −89.75 | −94.59 |
| 1.96 | 1.87 | 2.06 | −84.88 | −91.05 | −90.96 | −91.53 | −91.04 | −88.92 | −88.35 | −88.10 | −89.67 | −93.94 |
| 2.15 | 2.06 | 2.26 | −85.27 | −90.16 | −89.81 | −90.30 | −90.43 | −88.60 | −88.16 | −87.58 | −88.56 | −92.92 |
| 2.37 | 2.26 | 2.49 | −86.88 | −89.54 | −88.99 | −89.75 | −90.17 | −88.52 | −87.26 | −87.48 | −87.92 | −91.90 |
| 2.61 | 2.49 | 2.74 | −87.97 | −90.26 | −88.65 | −89.11 | −89.45 | −88.48 | −87.42 | −86.42 | −87.98 | −91.37 |
| 2.87 | 2.74 | 3.02 | −87.77 | −90.30 | −87.74 | −87.22 | −88.09 | −87.54 | −86.05 | −84.99 | −87.05 | −90.08 |
| 3.16 | 3.02 | 3.32 | −87.95 | −90.26 | −88.54 | −87.17 | −86.75 | −86.94 | −84.83 | −84.55 | −86.41 | −88.43 |
| 3.48 | 3.32 | 3.66 | −88.55 | −90.89 | −89.15 | −88.30 | −87.33 | −87.95 | −85.64 | −85.74 | −86.90 | −88.91 |
| 3.83 | 3.66 | 4.02 | −89.14 | −90.33 | −87.79 | −87.35 | −87.66 | −88.46 | −87.43 | −86.16 | −86.64 | −90.22 |
| 4.22 | 4.02 | 4.43 | −89.48 | −89.48 | −86.34 | −86.12 | −86.83 | −87.70 | −88.25 | −86.65 | −86.48 | −89.53 |
| 4.64 | 4.43 | 4.88 | −88.34 | −88.12 | −84.45 | −84.15 | −86.43 | −86.99 | −85.65 | −85.81 | −85.92 | −87.37 |
| 5.11 | 4.88 | 5.37 | −79.82 | −86.21 | −83.24 | −81.41 | −82.68 | −82.47 | −79.29 | −79.83 | −81.78 | −83.10 |
| 5.62 | 5.37 | 5.91 | −79.61 | −86.89 | −84.23 | −80.44 | −80.97 | −81.37 | −79.44 | −80.57 | −81.28 | −82.44 |
| 6.19 | 5.91 | 6.50 | −78.46 | −86.52 | −82.83 | −80.12 | −80.27 | −79.57 | −78.73 | −80.45 | −80.71 | −81.07 |
| 6.81 | 6.50 | 7.16 | −80.02 | −86.30 | −81.59 | −78.10 | −78.59 | −79.93 | −80.02 | −81.29 | −80.03 | −79.98 |
| 7.50 | 7.16 | 7.88 | −79.15 | −84.52 | −80.11 | −77.13 | −76.73 | −77.27 | −78.11 | −78.61 | −76.97 | −77.28 |
| 8.25 | 7.88 | 8.67 | −79.49 | −83.68 | −77.46 | −73.74 | −73.50 | −74.84 | −74.56 | −75.49 | −73.81 | −74.07 |
| 9.09 | 8.67 | 9.54 | −78.28 | −83.12 | −75.52 | −74.12 | −75.51 | −75.26 | −74.67 | −74.66 | −73.90 | −73.75 |
| 10.00 | 9.54 | 10.50 | −74.49 | −80.06 | −74.81 | −73.95 | −73.67 | −72.78 | −73.45 | −73.99 | −72.14 | −71.94 |
| 11.01 | 10.50 | 11.56 | −65.65 | −80.67 | −74.94 | −73.85 | −74.61 | −73.03 | −72.71 | −73.96 | −72.30 | −71.93 |
| 12.12 | 11.56 | 12.73 | −68.30 | −80.59 | −74.80 | −73.82 | −75.16 | −73.55 | −73.74 | −75.29 | −73.10 | −72.14 |
| 13.34 | 12.73 | 14.01 | −67.20 | −80.85 | −75.03 | −73.34 | −74.50 | −73.87 | −73.84 | −74.45 | −73.51 | −72.68 |
| 14.68 | 14.01 | 15.42 | −69.60 | −82.05 | −76.19 | −73.64 | −75.17 | −75.56 | −75.59 | −75.93 | −73.91 | −73.80 |
| 16.16 | 15.42 | 16.97 | −66.51 | −69.41 | −67.68 | −69.07 | −69.29 | −69.99 | −73.17 | −76.41 | −75.78 | −75.26 |
| 17.78 | 16.97 | 18.68 | −65.54 | −73.01 | −71.69 | −72.43 | −71.93 | −71.71 | −72.27 | −74.57 | −73.58 | −73.41 |
| 19.57 | 18.68 | 20.56 | −63.89 | −77.51 | −75.51 | −75.55 | −75.00 | −73.92 | −74.27 | −75.57 | −74.85 | −74.64 |
| 21.54 | 20.56 | 22.63 | −63.30 | −71.50 | −69.39 | −69.84 | −70.31 | −71.30 | −72.12 | −72.98 | −73.91 | −72.71 |
| 23.71 | 22.63 | 24.91 | −65.46 | −68.03 | −64.90 | −66.10 | −67.61 | −67.85 | −69.84 | −73.73 | −73.60 | −72.58 |
| 26.10 | 24.91 | 27.42 | −61.68 | −56.74 | −50.39 | −47.57 | −46.24 | −45.88 | −47.54 | −47.80 | −46.46 | −46.17 |
| 28.73 | 27.42 | 30.18 | −60.24 | −64.64 | −52.44 | −48.87 | −47.63 | −47.58 | −46.40 | −49.34 | −48.20 | −47.38 |
| 31.62 | 30.18 | 33.21 | −60.95 | −78.04 | −73.60 | −71.34 | −69.51 | −68.52 | −68.69 | −69.49 | −69.55 | −69.41 |
| 34.81 | 33.21 | 36.56 | −57.41 | −67.42 | −65.77 | −66.16 | −65.38 | −65.21 | −63.89 | −62.28 | −65.54 | −68.61 |
| 38.31 | 36.56 | 40.24 | −55.51 | −62.92 | −61.34 | −61.93 | −61.91 | −60.04 | −60.08 | −61.21 | −62.14 | −63.63 |
| 42.17 | 40.24 | 44.29 | −53.00 | −48.58 | −46.94 | −48.10 | −46.53 | −44.75 | −46.15 | −49.50 | −52.56 | −58.46 |
| 46.42 | 44.29 | 48.75 | −64.18 | −71.41 | −69.36 | −70.36 | −66.50 | −63.75 | −63.12 | −62.15 | −60.75 | −60.84 |
| 51.09 | 48.75 | 53.66 | −63.86 | −73.81 | −68.90 | −66.24 | −58.04 | −53.69 | −53.47 | −54.45 | −55.35 | −55.87 |
| 56.23 | 53.66 | 59.07 | −63.43 | −68.92 | −50.75 | −46.22 | −45.28 | −45.15 | −45.48 | −45.34 | −44.88 | −44.81 |
| 61.90 | 59.07 | 65.01 | −64.63 | −61.25 | −57.87 | −58.00 | −56.88 | −55.55 | −55.11 | −55.45 | −53.15 | −53.56 |
| 68.13 | 65.01 | 71.56 | −62.68 | −57.37 | −55.59 | −58.93 | −55.22 | −53.10 | −53.31 | −53.14 | −53.73 | −54.54 |
| 74.99 | 71.56 | 78.76 | −54.09 | −49.83 | −47.18 | −44.86 | −43.75 | −45.23 | −44.90 | −44.90 | −47.67 | −49.04 |
| 82.54 | 78.76 | 86.70 | −47.20 | −39.02 | −38.10 | −42.95 | −38.85 | −36.93 | −38.29 | −40.91 | −43.13 | −46.66 |
| 90.85 | 86.70 | 95.43 | −59.30 | −56.13 | −52.71 | −51.00 | −52.07 | −53.39 | −56.70 | −51.91 | −47.50 | −48.05 |
| 100.00 | 95.43 | 105.03 | −50.27 | −45.31 | −43.76 | −46.28 | −44.47 | −42.98 | −44.45 | −45.49 | −49.38 | −51.74 |
| 110.07 | 105.03 | 115.61 | −50.28 | −51.17 | −47.20 | −45.47 | −43.95 | −43.23 | −42.62 | −42.58 | −43.15 | −43.29 |
| 121.15 | 115.61 | 127.25 | −52.88 | −52.79 | −51.07 | −48.74 | −47.69 | −47.82 | −48.99 | −49.38 | −49.66 | −51.30 |
| 133.35 | 127.25 | 140.07 | −54.31 | −57.63 | −56.47 | −56.59 | −54.53 | −54.05 | −53.69 | −51.75 | −50.72 | −54.03 |
| 146.78 | 140.07 | 154.17 | −52.16 | −52.01 | −49.66 | −48.91 | −48.05 | −46.77 | −45.93 | −46.19 | −48.03 | −49.15 |

(section 20 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | | |
|---|---|---|---|---|---|---|---|---|---|---|---|
| (Hz) | (Hz) | (Hz) | 45.16 | 45.66 | 46.15 | 46.65 | 47.15 | 47.64 | 48.14 | 48.64 | 49.13 | 49.63 |
| 161.56 | 154.17 | 169.69 | −46.22 | −44.42 | −43.60 | −44.89 | −42.34 | −41.75 | −42.37 | −43.40 | −44.71 | −45.05 |
| 177.83 | 169.69 | 186.78 | −58.12 | −55.94 | −52.34 | −49.90 | −50.33 | −51.55 | −54.16 | −48.15 | −45.51 | −47.64 |
| 195.73 | 186.78 | 205.59 | −58.22 | −50.24 | −47.66 | −50.17 | −49.01 | −47.66 | −49.58 | −50.24 | −52.79 | −55.12 |
| 215.44 | 205.59 | 226.29 | −50.60 | −52.45 | −49.24 | −47.29 | −46.26 | −44.85 | −44.94 | −46.05 | −46.84 | −46.68 |

TABLE 2-continued

| | | | | | | | | | | | |
|---|---|---|---|---|---|---|---|---|---|---|---|
| 237.14 | 226.29 | 249.08 | −56.06 | −52.46 | −50.97 | −50.87 | −50.52 | −50.20 | −49.48 | −49.49 | −50.07 | −52.36 |
| 261.02 | 249.08 | 274.16 | −53.10 | −52.49 | −51.81 | −50.50 | −48.62 | −48.46 | −49.02 | −49.11 | −51.15 | −53.19 |
| 287.30 | 274.16 | 301.76 | −62.88 | −56.34 | −53.35 | −50.12 | −50.18 | −51.26 | −49.26 | −49.51 | −51.20 | −50.76 |
| 316.23 | 301.76 | 332.15 | −49.80 | −45.07 | −46.45 | −52.75 | −46.99 | −44.66 | −44.87 | −45.81 | −48.72 | −50.79 |
| 348.07 | 332.15 | 365.59 | −55.51 | −52.30 | −50.54 | −48.50 | −47.96 | −48.43 | −51.33 | −53.33 | −56.25 | −56.53 |
| 383.12 | 365.59 | 402.41 | −47.50 | −43.23 | −45.26 | −52.25 | −45.32 | −43.12 | −44.75 | −46.20 | −47.90 | −51.47 |
| 421.70 | 402.41 | 442.93 | −57.97 | −56.18 | −54.67 | −54.21 | −52.46 | −51.44 | −49.56 | −47.75 | −50.23 | −51.60 |
| 464.16 | 442.93 | 487.53 | −67.42 | −62.88 | −56.98 | −54.19 | −56.66 | −58.64 | −56.68 | −55.59 | −54.14 | −53.20 |
| 510.90 | 487.53 | 536.62 | −52.27 | −46.38 | −46.71 | −52.62 | −47.56 | −45.82 | −46.40 | −46.38 | −48.07 | −51.89 |
| 562.34 | 536.62 | 590.65 | −67.64 | −57.27 | −57.56 | −56.00 | −55.75 | −55.51 | −54.57 | −54.23 | −54.24 | −54.31 |
| 618.97 | 590.65 | 650.13 | −73.09 | −65.86 | −63.87 | −59.68 | −59.81 | −60.02 | −57.73 | −58.07 | −58.97 | −56.75 |
| 681.29 | 650.13 | 715.59 | −57.20 | −54.05 | −54.98 | −58.34 | −53.99 | −51.76 | −52.10 | −53.55 | −55.90 | −57.05 |
| 749.89 | 715.59 | 787.65 | −56.71 | −52.96 | −55.05 | −58.79 | −54.14 | −52.93 | −54.95 | −54.54 | −53.87 | −57.22 |
| 825.40 | 787.65 | 866.96 | −67.39 | −64.58 | −65.10 | −61.37 | −59.72 | −60.14 | −61.60 | −63.06 | −63.11 | −59.98 |
| 908.52 | 866.96 | 954.26 | −67.90 | −70.39 | −65.77 | −58.10 | −57.02 | −57.51 | −55.86 | −57.17 | −58.96 | −56.06 |
| 1000.00 | 954.26 | 1050.35 | −60.81 | −59.29 | −60.08 | −62.06 | −57.43 | −54.18 | −53.84 | −55.41 | −56.40 | −56.20 |
| 1100.69 | 1050.35 | 1156.11 | −72.26 | −69.62 | −66.86 | −64.38 | −62.34 | −60.48 | −60.95 | −63.10 | −63.89 | −61.14 |
| 1211.53 | 1156.11 | 1272.52 | −64.28 | −67.18 | −68.42 | −63.17 | −62.30 | −61.68 | −59.87 | −60.88 | −64.38 | −66.50 |
| 1333.52 | 1272.52 | 1400.66 | −62.93 | −68.36 | −68.08 | −64.99 | −60.75 | −59.59 | −60.64 | −61.17 | −59.58 | −58.79 |
| 1467.80 | 1400.66 | 1541.70 | −74.37 | −71.78 | −71.06 | −71.58 | −68.58 | −62.66 | −63.01 | −68.93 | −69.94 | −63.39 |
| 1615.60 | 1541.70 | 1696.94 | −66.13 | −71.84 | −74.38 | −72.90 | −71.58 | −63.06 | −62.52 | −67.09 | −65.76 | −62.52 |
| 1778.28 | 1696.94 | 1867.81 | −72.50 | −76.97 | −77.47 | −75.96 | −66.94 | −66.40 | −71.44 | −72.36 | −66.76 | −64.13 |
| 1957.34 | 1867.81 | 2055.89 | −72.40 | −75.62 | −76.81 | −76.50 | −76.36 | −67.28 | −66.54 | −71.40 | −74.05 | −67.98 |
| 2154.43 | 2055.89 | 2262.90 | −74.21 | −79.26 | −77.87 | −75.97 | −76.96 | −67.89 | −67.58 | −72.88 | −73.83 | −67.78 |
| 2371.37 | 2262.90 | 2490.77 | −73.56 | −78.56 | −76.72 | −74.58 | −76.49 | −74.54 | −72.81 | −73.04 | −73.53 | −75.56 |
| 2610.16 | 2490.77 | 2741.57 | −75.40 | −80.96 | −79.95 | −76.44 | −76.65 | −75.09 | −74.31 | −75.05 | −76.42 | −76.43 |
| 2872.98 | 2741.57 | 3017.63 | −76.48 | −86.60 | −81.47 | −76.82 | −78.23 | −77.37 | −75.34 | −76.69 | −77.79 | −76.87 |
| 3162.28 | 3017.63 | 3321.49 | −78.69 | −85.16 | −85.20 | −81.43 | −80.62 | −77.79 | −76.38 | −76.97 | −77.57 | −78.89 |
| 3480.70 | 3321.49 | 3655.94 | −82.41 | −89.12 | −87.50 | −82.10 | −79.89 | −78.77 | −79.12 | −80.05 | −81.28 | −81.57 |
| 3831.19 | 3655.94 | 4024.08 | −82.37 | −92.27 | −85.62 | −82.05 | −82.64 | −81.71 | −80.56 | −81.87 | −81.88 | −81.15 |
| 4216.97 | 4024.08 | 4429.28 | −86.07 | −95.56 | −91.85 | −88.72 | −84.43 | −82.58 | −82.89 | −83.91 | −82.70 | −81.63 |
| 4641.59 | 4429.28 | 4875.28 | −87.64 | −97.75 | −92.85 | −89.71 | −85.60 | −83.70 | −85.67 | −89.41 | −86.97 | −83.72 |
| 5108.97 | 4875.28 | 5366.19 | −88.91 | −100.88 | −96.81 | −93.55 | −91.26 | −84.04 | −84.43 | −92.01 | −90.64 | −83.87 |
| 5623.41 | 5366.19 | 5906.54 | −91.66 | −104.32 | −99.10 | −95.76 | −91.65 | −89.38 | −91.14 | −94.48 | −91.48 | −88.25 |
| 6189.66 | 5906.54 | 6501.29 | −91.31 | −105.26 | −101.46 | −97.73 | −97.42 | −91.93 | −91.67 | −95.76 | −96.37 | −91.82 |
| 6812.92 | 6501.29 | 7155.93 | −92.65 | −107.00 | −101.56 | −98.73 | −99.37 | −95.47 | −94.66 | −97.34 | −97.48 | −94.14 |
| 7498.94 | 7155.93 | 7876.49 | −92.88 | −107.58 | −102.65 | −100.12 | −100.76 | −98.98 | −97.57 | −98.64 | −99.52 | −97.65 |
| 8254.04 | 7876.49 | 8669.61 | −95.06 | −107.69 | −102.12 | −102.45 | −102.25 | −100.09 | −98.86 | −100.27 | −101.43 | −99.36 |
| 9085.18 | 8669.61 | 9542.59 | −97.23 | −109.52 | −104.40 | −102.28 | −103.41 | −101.57 | −100.35 | −101.48 | −101.51 | −99.50 |
| 10000.00 | 9542.59 | 10503.47 | −95.74 | −111.86 | −107.51 | −105.45 | −105.61 | −103.54 | −102.32 | −103.52 | −104.42 | −102.27 |
| 11006.94 | 10503.47 | 11561.11 | −94.57 | −114.29 | −108.18 | −106.06 | −108.05 | −106.92 | −105.58 | −106.41 | −106.41 | −104.88 |
| 12115.28 | 11561.11 | 12725.25 | −93.88 | −115.30 | −111.48 | −109.45 | −110.41 | −109.08 | −107.65 | −108.32 | −107.78 | −105.95 |
| 13335.21 | 12725.25 | 14006.60 | −96.04 | −117.80 | −112.86 | −110.91 | −112.32 | −111.42 | −110.08 | −110.39 | −109.70 | −108.02 |
| 14677.99 | 14006.60 | 15416.99 | −99.18 | −118.98 | −114.45 | −112.27 | −113.27 | −113.52 | −112.54 | −112.81 | −112.67 | −111.23 |
| 16155.98 | 15416.99 | 16969.39 | −105.74 | −120.58 | −119.12 | −118.56 | −118.45 | −117.05 | −116.34 | −116.55 | −116.46 | −113.82 |
| 17782.79 | 16969.39 | 18678.11 | −109.74 | −121.55 | −120.56 | −120.44 | −119.88 | −118.91 | −118.68 | −119.08 | −119.21 | −116.68 |
| 19573.42 | 18678.11 | 20558.88 | −110.91 | −122.09 | −121.25 | −121.16 | −120.68 | −119.93 | −119.81 | −120.22 | −120.41 | −118.36 |
| 21544.35 | 20558.88 | 22629.04 | −113.65 | −116.97 | −116.66 | −116.83 | −116.45 | −115.61 | −115.71 | −116.65 | −116.62 | −115.76 |

(section 21 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | | |
|---|---|---|---|---|---|---|---|---|---|---|---|---|
| (Hz) | (Hz) | (Hz) | 50.13 | 50.62 | 51.12 | 51.61 | 52.11 | 52.61 | 53.10 | 53.60 | 54.10 | 54.59 |
| 1.00 | 1.00 | 1.05 | −96.37 | −95.36 | −84.86 | −94.37 | −95.10 | −92.90 | −93.86 | −92.45 | −90.68 | −84.34 |
| 1.10 | 1.05 | 1.16 | −96.37 | −95.36 | −84.86 | −94.37 | −95.10 | −92.90 | −93.86 | −92.45 | −90.68 | −84.34 |
| 1.21 | 1.16 | 1.27 | −96.51 | −95.45 | −84.72 | −94.24 | −94.97 | −92.98 | −93.71 | −92.49 | −90.71 | −84.17 |
| 1.33 | 1.27 | 1.40 | −97.18 | −95.85 | −84.18 | −93.74 | −94.47 | −93.34 | −93.13 | −92.67 | −90.86 | −83.52 |
| 1.47 | 1.40 | 1.54 | −97.20 | −95.74 | −84.02 | −93.53 | −94.06 | −92.96 | −92.86 | −92.72 | −90.46 | −83.34 |
| 1.62 | 1.54 | 1.70 | −97.23 | −95.48 | −83.66 | −93.05 | −93.22 | −92.18 | −92.26 | −92.82 | −89.65 | −82.96 |
| 1.78 | 1.70 | 1.87 | −95.92 | −94.39 | −83.36 | −93.07 | −92.74 | −91.97 | −92.94 | −91.88 | −89.27 | −82.89 |
| 1.96 | 1.87 | 2.06 | −95.40 | −94.13 | −83.22 | −93.09 | −92.58 | −92.20 | −93.34 | −91.54 | −89.29 | −82.85 |
| 2.15 | 2.06 | 2.26 | −95.39 | −94.53 | −83.20 | −93.03 | −92.83 | −92.98 | −93.31 | −91.63 | −89.77 | −82.80 |
| 2.37 | 2.26 | 2.49 | −97.06 | −94.66 | −83.21 | −92.00 | −93.09 | −91.88 | −91.68 | −92.17 | −89.83 | −82.80 |
| 2.61 | 2.49 | 2.74 | −95.54 | −92.77 | −83.40 | −91.41 | −91.92 | −89.86 | −89.80 | −90.36 | −89.16 | −82.51 |
| 2.87 | 2.74 | 3.02 | −90.53 | −89.52 | −82.99 | −89.09 | −89.54 | −86.87 | −86.35 | −86.99 | −86.70 | −81.54 |
| 3.16 | 3.02 | 3.32 | −88.27 | −88.14 | −82.55 | −87.53 | −87.94 | −86.50 | −85.21 | −85.66 | −85.28 | −81.36 |
| 3.48 | 3.32 | 3.66 | −89.41 | −88.77 | −83.06 | −88.49 | −88.85 | −87.71 | −87.16 | −87.14 | −86.52 | −82.01 |
| 3.83 | 3.66 | 4.02 | −91.95 | −90.20 | −83.82 | −90.45 | −90.74 | −89.94 | −89.11 | −88.52 | −87.70 | −82.35 |
| 4.22 | 4.02 | 4.43 | −91.58 | −91.34 | −84.27 | −89.55 | −90.59 | −90.29 | −88.87 | −88.66 | −87.23 | −82.29 |
| 4.64 | 4.43 | 4.88 | −90.39 | −89.86 | −84.31 | −89.01 | −89.88 | −89.46 | −88.99 | −88.18 | −86.93 | −82.26 |
| 5.11 | 4.88 | 5.37 | −85.60 | −83.71 | −82.07 | −84.79 | −84.55 | −84.92 | −84.75 | −83.97 | −83.07 | −81.41 |
| 5.62 | 5.37 | 5.91 | −84.75 | −83.41 | −82.08 | −84.01 | −83.66 | −83.51 | −84.15 | −83.60 | −82.00 | −80.89 |
| 6.19 | 5.91 | 6.50 | −82.09 | −82.24 | −82.31 | −81.69 | −81.65 | −81.68 | −81.56 | −82.76 | −82.03 | −81.10 |
| 6.81 | 6.50 | 7.16 | −81.11 | −81.88 | −82.80 | −81.55 | −82.37 | −82.87 | −82.55 | −83.00 | −82.14 | −80.42 |
| 7.50 | 7.16 | 7.88 | −77.63 | −78.31 | −78.78 | −77.28 | −77.93 | −79.10 | −79.20 | −79.00 | −77.58 | −76.72 |
| 8.25 | 7.88 | 8.67 | −73.70 | −74.87 | −75.16 | −73.71 | −74.64 | −74.80 | −74.71 | −75.83 | −74.10 | −72.01 |
| 9.09 | 8.67 | 9.54 | −74.93 | −75.50 | −74.87 | −75.46 | −75.34 | −75.18 | −75.14 | −75.21 | −73.70 | −73.49 |

TABLE 2-continued

| | | | | | | | | | | |
|---|---|---|---|---|---|---|---|---|---|---|
| 10.00 | 9.54 | 10.50 | -73.70 | -73.75 | -73.73 | -74.23 | -73.15 | -73.76 | -74.70 | -74.46 72.54 -72.25 |
| 11.01 | 10.50 | 11.56 | -72.69 | -72.59 | -73.12 | -73.95 | -74.28 | -72.99 | -72.96 | -74.27 72.74 -71.49 |
| 12.12 | 11.56 | 12.73 | -72.35 | -72.96 | -73.70 | -74.76 | -74.65 | -73.67 | -73.91 | -75.10 73.04 -71.72 |
| 13.34 | 12.73 | 14.01 | -72.05 | -73.43 | -74.53 | -74.99 | -74.49 | -74.10 | -74.95 | -75.29 73.92 -71.95 |
| 14.68 | 14.01 | 15.42 | -74.64 | -75.93 | -76.49 | -76.02 | -75.47 | -75.70 | -76.47 | -76.53 74.88 -74.00 |
| 16.16 | 15.42 | 16.97 | -75.38 | -76.32 | -76.60 | -75.91 | -75.34 | -75.13 | -76.37 | -77.52 74.71 -72.92 |
| 17.78 | 16.97 | 18.68 | -74.34 | -75.20 | -75.64 | -74.27 | -73.28 | -74.11 | -74.76 | -76.04 73.90 -72.85 |
| 19.57 | 18.68 | 20.56 | -75.23 | -75.72 | -75.74 | -74.47 | -74.63 | -74.91 | -75.05 | -75.95 75.39 -73.50 |
| 21.54 | 20.56 | 22.63 | -72.34 | -73.11 | -73.72 | -72.98 | -72.90 | -72.63 | -73.03 | -72.68 72.25 -72.34 |
| 23.71 | 22.63 | 24.91 | -72.89 | -73.71 | -74.97 | -74.27 | -73.57 | -73.70 | -73.85 | -72.41 71.63 -71.95 |
| 26.10 | 24.91 | 27.42 | -45.77 | -45.20 | -45.35 | -44.82 | -44.01 | -45.30 | -45.87 | -45.69 45.37 -44.28 |
| 28.73 | 27.42 | 30.18 | -47.12 | -46.57 | -46.91 | -46.14 | -45.17 | -46.02 | -47.33 | -47.38 46.91 -45.38 |
| 31.62 | 30.18 | 33.21 | -68.84 | -68.73 | -70.25 | -69.41 | -54.71 | -54.88 | -69.23 | -53.82 49.49 -53.14 |
| 34.81 | 33.21 | 36.56 | -63.99 | -62.72 | -63.17 | -67.14 | -66.22 | -66.19 | -69.39 | -64.45 62.39 -63.85 |
| 38.31 | 36.56 | 40.24 | -61.79 | -60.91 | -62.32 | -63.51 | -62.89 | -62.75 | -63.83 | -63.96 62.46 -62.11 |
| 42.17 | 40.24 | 44.29 | -58.31 | -53.12 | -54.49 | -64.97 | -52.96 | -51.36 | -56.33 | -55.99 52.86 -52.07 |
| 46.42 | 44.29 | 48.75 | -60.89 | -58.63 | -59.19 | -62.46 | -59.18 | -57.46 | -59.16 | -51.80 51.84 -57.60 |
| 51.09 | 48.75 | 53.66 | -53.26 | -50.41 | -51.49 | -57.03 | -53.55 | -50.10 | -51.86 | -43.37 42.69 -48.14 |
| 56.23 | 53.66 | 59.07 | -44.56 | -43.84 | -43.99 | -44.41 | -43.58 | -43.11 | -43.72 | -43.85 42.73 -42.56 |
| 61.90 | 59.07 | 65.01 | -55.77 | -55.33 | -54.81 | -53.35 | -38.18 | -36.70 | -36.79 | -36.51 39.67 -44.98 |
| 68.13 | 65.01 | 71.56 | -53.08 | -51.23 | -49.95 | -48.82 | -48.57 | -47.91 | -48.11 | -49.84 46.34 -46.02 |
| 74.99 | 71.56 | 78.76 | -46.95 | -46.84 | -47.90 | -40.40 | -40.36 | -47.83 | -49.02 | -50.51 41.00 -39.29 |
| 82.54 | 78.76 | 86.70 | -48.44 | -49.01 | -48.86 | -48.37 | -48.34 | -48.57 | -48.66 | -49.29 49.28 -48.95 |
| 90.85 | 86.70 | 95.43 | -57.54 | -53.52 | -52.12 | -52.40 | -50.77 | -50.26 | -49.35 | -49.83 54.53 -53.92 |
| 100.00 | 95.43 | 105.03 | -51.29 | -49.73 | -49.44 | -49.03 | -49.39 | -49.18 | -48.55 | -44.57 44.70 -49.86 |
| 110.07 | 105.03 | 115.61 | -42.99 | -42.72 | -42.38 | -42.31 | -42.67 | -43.18 | -43.09 | -42.93 42.20 -42.21 |
| 121.15 | 115.61 | 127.25 | -52.25 | -50.49 | -50.55 | -49.26 | -49.75 | -49.66 | -48.89 | -48.35 45.59 -47.15 |
| 133.35 | 127.25 | 140.07 | -55.91 | -53.21 | -50.61 | -50.41 | -50.32 | -49.50 | -51.07 | -53.34 52.74 -51.85 |
| 146.78 | 140.07 | 154.17 | -48.05 | -47.20 | -46.99 | -47.92 | -48.55 | -49.80 | -50.43 | -49.33 47.72 -43.46 |

(section 22 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | | |
|---|---|---|---|---|---|---|---|---|---|---|---|---|
| (Hz) | (Hz) | (Hz) | 50.13 | 50.62 | 51.12 | 51.61 | 52.11 | 52.61 | 53.10 | 53.60 | 54.10 | 54.59 |
| 161.56 | 154.17 | 169.69 | 3145.15 | -44.88 | -44.61 | -44.91 | -44.90 | -45.20 | -45.47 | -45.19 | 3143.46 | -42.53 |
| 177.83 | 169.69 | 186.78 | -55.14 | -51.52 | -51.09 | -52.05 | -50.94 | -51.76 | -50.97 | -49.63 | 49.08 | -52.01 |
| 195.73 | 186.78 | 205.59 | -55.79 | -55.16 | -50.33 | -48.97 | -50.27 | -51.98 | -51.47 | -49.44 | 48.01 | -48.49 |
| 215.44 | 205.59 | 226.29 | -45.51 | -45.51 | -45.89 | -46.79 | -47.07 | -47.37 | -46.86 | -45.92 | 45.55 | -45.72 |
| 237.14 | 226.29 | 249.08 | -56.95 | -57.06 | -57.05 | -56.36 | -55.58 | -53.52 | -52.75 | -50.26 | 49.15 | -51.35 |
| 261.02 | 249.08 | 274.16 | -54.44 | -53.95 | -51.45 | -49.75 | -49.30 | -51.86 | -52.69 | -46.82 | 45.47 | -47.11 |
| 287.30 | 274.16 | 301.76 | -50.64 | -51.94 | -51.01 | -51.35 | -51.85 | -51.08 | -50.43 | -50.48 | 48.05 | -47.91 |
| 316.23 | 301.76 | 332.15 | -52.67 | -54.37 | -51.10 | -49.25 | -49.78 | -51.70 | -50.20 | -50.19 | 52.14 | -51.53 |
| 348.07 | 332.15 | 365.59 | -54.53 | -49.85 | -50.25 | -52.46 | -53.31 | -53.91 | -53.85 | -50.88 | 50.25 | -51.33 |
| 383.12 | 365.59 | 402.41 | -54.83 | -51.74 | -50.57 | -50.97 | -53.78 | -51.28 | -48.63 | -48.61 | 49.13 | -49.34 |
| 421.70 | 402.41 | 442.93 | -49.26 | -47.71 | -48.63 | -56.12 | -58.97 | -55.57 | -53.81 | -55.10 | 52.71 | -48.94 |
| 464.16 | 442.93 | 487.53 | -52.51 | -50.77 | -52.02 | -57.56 | -59.64 | -57.24 | -56.72 | -58.87 | 57.58 | -51.37 |
| 510.90 | 487.53 | 536.62 | -51.18 | -46.69 | -47.68 | -55.33 | -53.84 | -51.52 | -55.52 | -51.23 | 49.90 | -48.17 |
| 562.34 | 536.62 | 590.65 | -55.39 | -56.14 | -53.70 | -53.92 | -55.86 | -56.11 | -55.52 | -56.05 | 53.18 | -51.59 |
| 618.97 | 590.65 | 650.13 | -54.74 | -55.26 | -55.42 | -56.48 | -58.05 | -57.40 | -56.56 | -57.63 | 56.67 | -55.36 |
| 681.29 | 650.13 | 715.59 | -57.37 | -53.46 | -53.24 | -54.51 | -56.66 | -55.08 | -53.08 | -53.83 | 58.63 | -55.36 |
| 749.89 | 715.59 | 787.65 | -63.05 | -62.89 | -58.90 | -57.03 | -59.40 | -57.11 | -54.32 | -53.64 | 53.99 | -54.53 |
| 825.40 | 787.65 | 866.96 | -59.66 | -58.22 | -57.30 | -57.81 | -61.24 | -59.83 | -57.32 | -58.30 | 58.25 | -57.37 |
| 908.52 | 866.96 | 954.26 | -56.06 | -56.45 | -55.45 | -56.57 | -57.04 | -55.81 | -55.23 | -55.80 | 55.56 | -54.67 |
| 1000.00 | 954.26 | 1050.35 | -58.78 | -61.32 | -58.59 | -57.22 | -59.99 | -62.05 | -58.22 | -57.89 | 59.16 | -56.91 |
| 1100.69 | 1050.35 | 1156.11 | -63.49 | -62.26 | -61.19 | -63.68 | -65.10 | -64.04 | -67.12 | -66.97 | 63.16 | -59.51 |
| 1211.53 | 1156.11 | 1272.52 | -65.22 | -62.69 | -61.70 | -62.32 | -61.52 | -61.55 | -60.83 | -59.17 | 59.97 | -62.22 |
| 1333.52 | 1272.52 | 1400.66 | -62.74 | -64.84 | -62.56 | -62.59 | -65.94 | -61.39 | -61.29 | -61.32 | 62.47 | -60.30 |
| 1467.80 | 1400.66 | 1541.70 | -63.56 | -69.09 | -68.31 | -69.52 | -70.27 | -68.69 | -63.47 | -63.47 | 67.68 | -66.75 |
| 1615.60 | 1541.70 | 1696.94 | -64.66 | -66.96 | -67.20 | -69.34 | -70.70 | -68.10 | -65.90 | -64.98 | 67.37 | -62.81 |
| 1778.28 | 1696.94 | 1867.81 | -66.27 | -69.44 | -68.79 | -70.39 | -73.38 | -67.00 | -66.71 | -66.68 | 66.86 | -65.63 |
| 1957.34 | 1867.81 | 2055.89 | -68.12 | -70.91 | -70.77 | -73.19 | -74.29 | -73.22 | -66.51 | -67.07 | 74.31 | -72.63 |
| 2154.43 | 2055.89 | 2262.90 | -68.18 | -69.26 | -70.33 | -75.15 | -76.48 | -75.81 | -72.97 | -71.52 | 73.88 | -67.57 |
| 2371.37 | 2262.90 | 2490.77 | -76.97 | -74.88 | -74.20 | -74.13 | -75.62 | -74.07 | -73.13 | -75.91 | 76.62 | -74.53 |
| 2610.16 | 2490.77 | 2741.57 | -75.70 | -69.38 | -69.17 | -73.87 | -75.72 | -76.31 | -73.68 | -74.52 | 74.90 | -71.12 |
| 2872.98 | 2741.57 | 3017.63 | -75.96 | -71.48 | -72.41 | -76.88 | -77.23 | -77.11 | -76.14 | -75.25 | 75.33 | -73.03 |
| 3162.28 | 3017.63 | 3321.49 | -78.78 | -72.52 | -72.97 | -78.25 | -79.64 | -78.35 | -76.98 | -78.65 | 79.18 | -72.83 |
| 3480.70 | 3321.49 | 3655.94 | -82.51 | -76.33 | -74.57 | -77.03 | -79.51 | -79.96 | -80.34 | -79.05 | 78.97 | -74.99 |
| 3831.19 | 3655.94 | 4024.08 | -82.49 | -78.97 | -79.10 | -81.95 | -82.42 | -81.06 | -80.10 | -79.59 | 79.66 | -77.01 |
| 4216.97 | 4024.08 | 4429.28 | -82.03 | -76.48 | -76.59 | -82.61 | -86.53 | -84.00 | -83.54 | -82.79 | 82.73 | -79.11 |
| 4641.59 | 4429.28 | 4875.28 | -84.02 | -81.64 | -81.38 | -85.89 | -87.66 | -85.20 | -84.81 | -84.78 | 85.35 | -81.78 |
| 5108.97 | 4875.28 | 5366.19 | -84.14 | -83.59 | -82.98 | -87.08 | -92.30 | -90.47 | -85.92 | -85.15 | 89.02 | -83.13 |
| 5623.41 | 5366.19 | 5906.54 | -88.80 | -87.96 | -87.73 | -90.90 | -94.36 | -91.48 | -89.92 | -89.58 | 90.03 | -86.62 |
| 6189.66 | 5906.54 | 6501.29 | -91.78 | -86.84 | -85.91 | -91.73 | -95.08 | -94.79 | -91.68 | -92.04 | 94.89 | -87.95 |
| 6812.92 | 6501.29 | 7155.93 | -93.18 | -88.00 | -88.18 | -94.31 | -96.34 | -96.23 | -94.64 | -94.86 | 94.56 | -88.28 |
| 7498.94 | 7155.93 | 7876.49 | -96.57 | -91.52 | -91.60 | -97.06 | -98.80 | -98.38 | -97.11 | -97.21 | 97.84 | -92.81 |
| 8254.04 | 7876.49 | 8669.61 | -99.00 | -93.81 | -93.69 | -98.82 | -100.23 | -99.36 | -98.27 | -98.63 | 98.66 | -93.44 |
| 9085.18 | 8669.61 | 9542.59 | -99.56 | -93.70 | -93.53 | -98.91 | -101.24 | -100.65 | -99.98 | -99.90 | 99.99 | -94.67 |

TABLE 2-continued

| | | | | | | | | | | | |
|---|---|---|---|---|---|---|---|---|---|---|---|
| 10000.00 | 9542.59 | 10503.47 | −102.13 | −97.48 | −97.21 | −101.06 | −102.46 | −102.39 | −101.89 | −101.55 | −101.32 | −97.26 |
| 11006.94 | 10503.47 | 11561.11 | −104.04 | −97.70 | −97.91 | −103.27 | −105.03 | −105.28 | −104.64 | −104.22 | −103.96 | −96.62 |
| 12115.28 | 11561.11 | 12725.25 | −104.93 | −98.22 | −98.21 | −104.58 | −106.10 | −107.10 | −106.61 | −105.99 | −105.43 | −97.70 |
| 13335.21 | 12725.25 | 14006.60 | −106.92 | −101.08 | −101.13 | −105.61 | −106.91 | −108.92 | −108.56 | −107.65 | −106.82 | −100.95 |
| 14677.99 | 14006.60 | 15416.99 | −109.73 | −103.44 | −103.26 | −107.83 | −109.28 | −110.91 | −110.56 | −109.94 | −109.69 | −102.77 |
| 16155.98 | 15416.99 | 16969.39 | −111.40 | −103.73 | −103.61 | −108.79 | −112.27 | −114.04 | −113.85 | −113.21 | −112.23 | −103.73 |
| 17782.79 | 16969.39 | 18678.11 | −114.46 | −107.77 | −107.61 | −113.43 | −115.73 | −116.30 | −116.23 | −115.68 | −114.79 | −108.14 |
| 19573.42 | 18678.11 | 20558.88 | −116.49 | −109.87 | −109.61 | −115.34 | −117.56 | −117.54 | −117.46 | −116.98 | −116.06 | −108.83 |
| 21544.35 | 20558.88 | 22629.04 | −115.91 | −115.10 | −114.99 | −116.14 | −116.33 | −116.15 | −115.97 | −115.63 | −115.69 | −114.11 |

(section 23 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | |
|---|---|---|---|---|---|---|---|---|---|---|---|
| (Hz) | (Hz) | (Hz) | 55.09 | 55.58 | B56.08 | 56.58 | 57.07 | 57.57 | 58.07 | 58.56 | 59.06 | 59.55 |
| 1.00 | 1.00 | 1.05 | −70.28 | −70.26 | −85.94 | −73.55 | −74.20 | −90.87 | −88.60 | −89.26 | −75.71 | −76.01 |
| 1.10 | 1.05 | 1.16 | −70.28 | −70.26 | −85.94 | −73.55 | −74.20 | −90.87 | −88.60 | −89.26 | −75.71 | −76.01 |
| 1.21 | 1.16 | 1.27 | −70.32 | −70.34 | −85.40 | −73.57 | −74.30 | −89.90 | −87.68 | −88.67 | −75.98 | −76.29 |
| 1.33 | 1.27 | 1.40 | −70.48 | −70.69 | −83.67 | −73.62 | −74.74 | −87.25 | −85.13 | −86.83 | −77.33 | −77.73 |
| 1.47 | 1.40 | 1.54 | −71.03 | −71.34 | −83.45 | −73.51 | −74.88 | −86.69 | −84.35 | −86.00 | −77.67 | −78.05 |
| 1.62 | 1.54 | 1.70 | −72.70 | −73.43 | −82.97 | −73.26 | −75.26 | −85.60 | −82.91 | −84.49 | −78.59 | −78.93 |
| 1.78 | 1.70 | 1.87 | −72.28 | −72.90 | −83.42 | −73.49 | −75.83 | −86.55 | −82.32 | −83.03 | −78.87 | −79.59 |
| 1.96 | 1.87 | 2.06 | −72.10 | −72.63 | −83.83 | −73.71 | −76.14 | −87.45 | −82.23 | −82.50 | −79.19 | −80.04 |
| 2.15 | 2.06 | 2.26 | −72.11 | −72.53 | −84.36 | −74.07 | −76.18 | −88.49 | −82.70 | −82.58 | −79.74 | −80.40 |
| 2.37 | 2.26 | 2.49 | −72.39 | −72.70 | −84.95 | −74.75 | −76.00 | −87.63 | −84.37 | −84.14 | −80.58 | −81.50 |
| 2.61 | 2.49 | 2.74 | −71.92 | −72.34 | −85.48 | −75.54 | −76.20 | −86.19 | −85.07 | −84.28 | −81.20 | −81.85 |
| 2.87 | 2.74 | 3.02 | −71.22 | −71.60 | −84.35 | −75.46 | −76.31 | −84.87 | −81.44 | −83.69 | −81.62 | −81.80 |
| 3.16 | 3.02 | 3.32 | −71.84 | −72.24 | −82.56 | −73.93 | −76.50 | −81.16 | −79.98 | −83.46 | −82.33 | −82.14 |
| 3.48 | 3.32 | 3.66 | −74.06 | −74.69 | −83.05 | −73.87 | −77.47 | −83.55 | −81.51 | −83.05 | −83.09 | −82.96 |
| 3.83 | 3.66 | 4.02 | −74.44 | −74.85 | −83.69 | −74.82 | −76.53 | −87.48 | −81.31 | −81.01 | −84.72 | −83.95 |
| 4.22 | 4.02 | 4.43 | −72.57 | −72.32 | −80.44 | −73.77 | −74.60 | −86.65 | −75.88 | −75.94 | −85.39 | −83.79 |
| 4.64 | 4.43 | 4.88 | −73.22 | −72.84 | −75.95 | −72.36 | −74.24 | −81.98 | −71.05 | −71.15 | −83.92 | −82.61 |
| 5.11 | 4.88 | 5.37 | −74.26 | −73.12 | −74.03 | −71.31 | −74.02 | −76.79 | −70.99 | −71.62 | −81.07 | −80.90 |
| 5.62 | 5.37 | 5.91 | −74.13 | −71.34 | −72.25 | −71.07 | −73.47 | −72.97 | −69.51 | −71.43 | −80.30 | −80.82 |
| 6.19 | 5.91 | 6.50 | −76.92 | −71.06 | −71.60 | −72.62 | −73.15 | −72.66 | −67.88 | −69.15 | −81.09 | −81.58 |
| 6.81 | 6.50 | 7.16 | −77.79 | −76.18 | −77.88 | −72.93 | −73.10 | −74.67 | −70.38 | −70.55 | −80.73 | −80.93 |
| 7.50 | 7.16 | 7.88 | −75.51 | −74.63 | −76.02 | −72.80 | −72.70 | −72.84 | −70.37 | −72.31 | −77.61 | −77.42 |
| 8.25 | 7.88 | 8.67 | −72.13 | −73.79 | −74.38 | −70.98 | −72.02 | −72.70 | −71.20 | −73.31 | −75.33 | −73.97 |
| 9.09 | 8.67 | 9.54 | −73.96 | −72.32 | −73.40 | −73.20 | −73.20 | −69.70 | −68.78 | −71.85 | −74.82 | −75.95 |
| 10.00 | 9.54 | 10.50 | −72.07 | −71.12 | −72.57 | −71.72 | −71.60 | −69.20 | −67.73 | −70.55 | −73.19 | −74.52 |
| 11.01 | 10.50 | 11.56 | −71.47 | −71.87 | −73.47 | −72.73 | −72.30 | −70.30 | −69.06 | −70.65 | −73.35 | −73.34 |
| 12.12 | 11.56 | 12.73 | −72.29 | −71.44 | −72.94 | −74.05 | −72.81 | −69.78 | −67.88 | −70.51 | −73.54 | −73.96 |
| 13.34 | 12.73 | 14.01 | −71.85 | −72.96 | −74.74 | −74.25 | −74.07 | −71.86 | −72.03 | −73.56 | −73.66 | −72.83 |
| 14.68 | 14.01 | 15.42 | −75.01 | −74.64 | −74.98 | −74.23 | −73.57 | −72.98 | −72.77 | −74.18 | −74.69 | −75.14 |
| 16.16 | 15.42 | 16.97 | −74.17 | −74.89 | −75.55 | −74.24 | −74.52 | −74.58 | −73.37 | −73.69 | −74.68 | −75.93 |
| 17.78 | 16.97 | 18.68 | −73.76 | −74.44 | −75.48 | −74.79 | −76.01 | −74.16 | −72.58 | −73.68 | −74.49 | −75.23 |
| 19.57 | 18.68 | 20.56 | −73.92 | −75.71 | −76.49 | −76.55 | −76.76 | −75.45 | −74.86 | −75.40 | −75.26 | −75.99 |
| 21.54 | 20.56 | 22.63 | −72.88 | −73.34 | −73.32 | −73.56 | −74.90 | −73.70 | −74.50 | −73.56 | −73.35 | −75.61 |
| 23.71 | 22.63 | 24.91 | −71.02 | −71.89 | −73.85 | −74.08 | −73.88 | −70.74 | −69.62 | −68.88 | −69.83 | −74.55 |
| 26.10 | 24.91 | 27.42 | −42.40 | −41.65 | −43.68 | −43.90 | −44.68 | −46.65 | −47.52 | −49.27 | −48.98 | −47.63 |
| 28.73 | 27.42 | 30.18 | −43.47 | −42.97 | −45.18 | −45.68 | −46.31 | −47.88 | −48.80 | −50.06 | −49.87 | −48.97 |
| 31.62 | 30.18 | 33.21 | −57.62 | −69.54 | −70.49 | −69.21 | −53.47 | −53.29 | −52.96 | −46.85 | −42.27 | −42.96 | −48.57 |
| 34.81 | 33.21 | 36.56 | −65.66 | −69.97 | −70.63 | −70.50 | −67.11 | −52.86 | −46.93 | −46.14 | −48.18 | −55.46 |
| 38.31 | 36.56 | 40.24 | −63.76 | −65.29 | −65.59 | −65.67 | −65.78 | −46.32 | −43.41 | −47.20 | −60.82 | −62.71 |
| 42.17 | 40.24 | 44.29 | −50.36 | −49.83 | −57.26 | −64.04 | −52.38 | −50.99 | −46.27 | −43.86 | −44.52 | −47.78 |
| 46.42 | 44.29 | 48.75 | −57.48 | −55.84 | −52.25 | −50.71 | −54.39 | −57.74 | −52.26 | −45.54 | −45.33 | −52.07 |
| 51.09 | 48.75 | 53.66 | −50.05 | −51.07 | −52.74 | −56.58 | −50.68 | −49.28 | −53.22 | −36.05 | −36.00 | −49.91 |
| 56.23 | 53.66 | 59.07 | −43.53 | −44.17 | −44.70 | −44.64 | −43.94 | −44.72 | −46.66 | −47.42 | −46.96 | −46.89 |
| 61.90 | 59.07 | 65.01 | −54.20 | −54.80 | −56.14 | −55.92 | −56.94 | −57.46 | −55.69 | −55.26 | −53.89 | −55.33 |
| 68.13 | 65.01 | 71.56 | −48.43 | −50.10 | −50.16 | −50.35 | −48.59 | −46.47 | −40.93 | −41.00 | −47.27 | −48.58 |
| 74.99 | 71.56 | 78.76 | −40.64 | −42.22 | −50.34 | −51.79 | −48.20 | −46.36 | −48.77 | −49.41 | −52.00 |
| 82.54 | 78.76 | 86.70 | −47.63 | −47.25 | −48.71 | −49.64 | −49.64 | −49.31 | −48.56 | −49.78 | −49.73 | −49.89 |
| 90.85 | 86.70 | 95.43 | −50.68 | −47.58 | −44.56 | −43.46 | −46.30 | −47.25 | −39.79 | −39.86 | −49.38 | −50.71 |
| 100.00 | 95.43 | 105.03 | −50.89 | −49.97 | −49.34 | −46.35 | −47.21 | −49.19 | −45.43 | −39.33 | −40.27 | −52.68 |
| 110.07 | 105.03 | 115.61 | −42.03 | −42.03 | −42.14 | −42.62 | −42.69 | −42.61 | −39.88 | −41.41 | −43.74 | −47.01 |
| 121.15 | 115.61 | 127.25 | −50.53 | −51.12 | −50.15 | −47.96 | −50.35 | −53.31 | −52.38 | −51.00 | −51.62 | −66.51 |
| 133.35 | 127.25 | 140.07 | −49.43 | −48.85 | −48.53 | −46.45 | −47.07 | −48.23 | −48.57 | −49.20 | −49.53 | −50.09 |
| 146.78 | 140.07 | 154.17 | −43.03 | −47.00 | −51.00 | −51.07 | −53.15 | −54.09 | −53.75 | −52.32 | −51.64 | −52.47 |

(section 24 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | |
|---|---|---|---|---|---|---|---|---|---|---|---|
| (Hz) | (Hz) | (Hz) | 55.09 | 55.58 | 56.08 | 56.58 | 57.07 | 57.57 | 58.07 | 58.56 | 59.06 | 59.55 |
| 161.56 | 154.17 | 169.69 | −42.89 | −43.67 | −44.49 | −43.42 | −44.28 | −45.61 | −44.80 | −45.22 | −45.66 | −47.76 |
| 177.83 | 169.69 | 186.78 | −50.74 | −44.43 | −42.66 | −45.94 | −51.25 | −51.05 | −43.09 | −43.04 | −50.39 | −53.60 |

TABLE 2-continued

| | | | | | | | | | | | |
|---|---|---|---|---|---|---|---|---|---|---|---|
| 195.73 | 186.78 | 205.59 | −50.39 | −50.74 | −50.17 | −51.13 | −49.86 | −47.33 | −44.90 | −43.18 | −44.18 | −48.27 |
| 215.44 | 205.59 | 226.29 | −46.25 | −45.94 | −46.60 | −46.27 | −46.05 | −45.44 | −41.84 | −41.58 | −45.47 | −47.93 |
| 237.14 | 226.29 | 249.08 | −54.51 | −53.83 | −53.46 | −54.20 | −55.05 | −53.87 | −52.00 | −49.87 | −49.52 | −53.94 |
| 261.02 | 249.08 | 274.16 | −51.10 | −50.33 | −45.83 | −45.95 | −45.94 | −45.92 | −47.03 | −42.23 | −42.31 | −46.77 |
| 287.30 | 274.16 | 301.76 | −47.75 | −46.34 | −46.53 | −47.07 | −49.83 | −54.78 | −49.64 | −48.94 | −52.12 | −57.60 |
| 316.23 | 301.76 | 332.15 | −50.42 | −50.83 | −48.60 | −46.66 | −49.42 | −50.14 | −46.95 | −48.15 | −51.85 | −56.31 |
| 348.07 | 332.15 | 365.59 | −52.54 | −54.17 | −54.34 | −52.65 | −53.08 | −49.60 | −48.00 | −48.00 | −51.14 | −56.74 |
| 383.12 | 365.59 | 402.41 | −49.88 | −49.03 | −49.01 | −50.16 | −50.81 | −47.72 | −44.85 | −47.17 | −52.61 | −56.73 |
| 421.70 | 402.41 | 442.93 | −48.64 | −51.45 | −53.40 | −53.08 | −55.28 | −50.23 | −49.83 | −50.17 | −53.29 | −58.62 |
| 464.16 | 442.93 | 487.53 | −51.62 | −54.24 | −52.55 | −50.87 | −52.20 | −55.74 | −53.30 | −55.00 | −56.11 | −61.25 |
| 510.90 | 487.53 | 536.62 | −49.31 | −49.56 | −50.28 | −48.99 | −49.56 | −52.18 | −50.59 | −49.46 | −51.13 | −54.18 |
| 562.34 | 536.62 | 590.65 | −50.43 | −50.32 | −51.65 | −50.90 | −53.01 | −53.08 | −51.19 | −50.00 | −51.65 | −62.27 |
| 618.97 | 590.65 | 650.13 | −48.07 | −47.87 | −52.86 | −52.06 | −56.24 | −61.93 | −53.79 | −54.25 | −62.16 | −66.44 |
| 681.29 | 650.13 | 715.59 | −54.99 | −54.09 | −52.83 | −53.89 | −54.52 | −51.56 | −49.25 | −50.07 | −56.36 | −58.98 |
| 749.89 | 715.59 | 787.65 | −55.81 | −53.21 | −54.06 | −52.61 | −52.50 | −53.04 | −52.98 | −53.03 | −54.11 | −58.65 |
| 825.40 | 787.65 | 866.96 | −54.61 | −54.29 | −57.66 | −56.10 | −56.09 | −58.02 | −57.58 | −58.58 | −62.01 | −67.85 |
| 908.52 | 866.96 | 954.26 | −52.59 | −52.00 | −52.75 | −54.47 | −58.23 | −59.61 | −57.15 | −56.02 | −60.33 | −62.04 |
| 1000.00 | 954.26 | 1050.35 | −54.13 | −55.10 | −57.92 | −56.80 | −57.75 | −55.85 | −54.89 | −55.93 | −57.62 | −57.72 |
| 1100.69 | 1050.35 | 1156.11 | −57.98 | −58.66 | −60.92 | −60.06 | −60.68 | −60.57 | −60.96 | −63.24 | −66.99 | −65.14 |
| 1211.53 | 1156.11 | 1272.52 | −58.96 | −58.39 | −59.84 | −58.99 | −62.28 | −64.27 | −59.66 | −60.93 | −67.10 | −71.38 |
| 1333.52 | 1272.52 | 1400.66 | −58.37 | −61.39 | −55.88 | −62.10 | −60.18 | −60.70 | −60.98 | −61.45 | −62.61 |
| 1467.80 | 1400.66 | 1541.70 | −69.23 | −66.89 | −59.43 | −58.49 | −63.54 | −63.95 | −63.96 | −69.75 | −72.57 | −65.45 |
| 1615.60 | 1541.70 | 1696.94 | −61.35 | −64.59 | −65.17 | −63.32 | −64.20 | −62.21 | −61.10 | −65.15 | −68.68 | −65.38 |
| 1778.28 | 1696.94 | 1867.81 | −60.50 | −61.99 | −70.28 | −66.84 | −67.40 | −66.61 | −70.99 | −69.80 | −67.00 | −68.31 |
| 1957.34 | 1867.81 | 2055.89 | −72.27 | −71.87 | −71.88 | −70.87 | −71.43 | −67.14 | −65.56 | −69.62 | −74.65 | −69.50 |
| 2154.43 | 2055.89 | 2262.90 | −67.04 | −72.24 | −71.46 | −68.23 | −69.83 | −68.05 | −67.51 | −71.43 | −74.21 | −69.62 |
| 2371.37 | 2262.90 | 2490.77 | −66.74 | −67.11 | −73.54 | −70.82 | −73.07 | −72.28 | −71.68 | −74.32 | −75.38 | −77.84 |
| 2610.16 | 2490.77 | 2741.57 | −69.22 | −71.64 | −74.69 | −71.44 | −72.14 | −75.43 | −73.31 | −74.02 | −76.69 | −79.34 |
| 2872.98 | 2741.57 | 3017.63 | −70.16 | −71.88 | −70.48 | −64.67 | −66.28 | −79.29 | −75.35 | −75.85 | −79.46 | −81.37 |
| 3162.28 | 3017.63 | 3321.49 | −71.20 | −78.15 | −73.64 | −70.10 | −72.18 | −76.86 | −75.80 | −77.35 | −79.30 | −80.98 |
| 3480.70 | 3321.49 | 3655.94 | −71.65 | −73.84 | −76.32 | −73.55 | −75.86 | −79.15 | −78.89 | −79.82 | −83.24 | −84.26 |
| 3831.19 | 3655.94 | 4024.08 | −76.48 | −80.33 | −76.67 | −74.47 | −77.75 | −82.34 | −80.67 | −81.94 | −84.74 | −85.43 |
| 4216.97 | 4024.08 | 4429.28 | −75.63 | −80.50 | −80.04 | −75.32 | −77.48 | −83.14 | −82.95 | −83.27 | −84.39 | −85.07 |
| 4641.59 | 4429.28 | 4875.28 | −76.35 | −77.99 | −81.84 | −77.42 | −79.44 | −84.29 | −85.31 | −88.51 | −88.72 | −86.97 |
| 5108.97 | 4875.28 | 5366.19 | −78.87 | −81.75 | −86.48 | −80.69 | −82.15 | −85.46 | −85.30 | −92.03 | −92.56 | −86.06 |
| 5623.41 | 5366.19 | 5906.54 | −80.60 | −82.22 | −85.83 | −83.58 | −87.30 | −90.53 | −91.86 | −95.33 | −93.46 | −91.73 |
| 6189.66 | 5906.54 | 6501.29 | −81.20 | −83.90 | −87.32 | −84.39 | −87.73 | −93.10 | −92.72 | −97.37 | −98.65 | −93.90 |
| 6812.92 | 6501.29 | 7155.93 | −82.94 | −86.51 | −87.89 | −83.84 | −86.33 | −96.41 | −95.52 | −98.45 | −100.47 | −97.50 |
| 7498.94 | 7155.93 | 7876.49 | −86.49 | −87.76 | −90.89 | −88.21 | −91.17 | −99.45 | −98.38 | −99.98 | −102.23 | −101.36 |
| 8254.04 | 7876.49 | 8669.61 | −89.45 | −92.90 | −94.10 | −91.03 | −93.59 | −100.69 | −99.74 | −100.94 | −103.00 | −102.66 |
| 9085.18 | 8669.61 | 9542.59 | −89.62 | −92.23 | −94.06 | −90.44 | −92.85 | −101.15 | −100.02 | −102.23 | −104.42 | −104.00 |
| 10000.00 | 9542.59 | 10503.47 | −92.75 | −95.39 | −95.78 | −93.34 | −96.66 | −101.59 | −99.57 | −102.23 | −106.43 | −105.99 |
| 11006.94 | 10503.47 | 11561.11 | −91.27 | −94.86 | −96.64 | −93.81 | −97.33 | −107.15 | −106.10 | −107.94 | −109.41 | −109.19 |
| 12115.28 | 11561.11 | 12725.25 | −91.49 | −95.22 | −98.36 | −95.57 | −98.81 | −111.17 | −110.04 | −111.34 | −112.44 | −112.04 |
| 13335.21 | 12725.25 | 14006.60 | −96.86 | −100.99 | −100.33 | −97.55 | −101.10 | −113.06 | −111.28 | −112.87 | −115.48 | −114.30 |
| 14677.99 | 14006.60 | 15416.99 | −96.25 | −98.95 | −102.56 | −99.45 | −102.78 | −115.86 | −115.01 | −116.03 | −116.62 | −115.48 |
| 16155.98 | 15416.99 | 16969.39 | −97.93 | −102.16 | −102.92 | −99.29 | −102.10 | −118.40 | −116.75 | −117.22 | −118.19 | −117.62 |
| 17782.79 | 16969.39 | 18678.11 | −102.77 | −106.23 | −108.15 | −105.09 | −108.37 | −120.85 | −119.32 | −119.90 | −120.61 | −118.19 |
| 19573.42 | 18678.11 | 20558.88 | −103.67 | −107.08 | −108.55 | −106.44 | −110.55 | −121.51 | −120.29 | −120.66 | −121.07 | −117.59 |
| 21544.35 | 20558.88 | 22629.04 | −111.11 | −112.56 | −113.61 | −112.94 | −115.08 | −116.57 | −116.45 | −117.22 | −117.51 | −115.50 |

(section 25 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | | | | |
|---|---|---|---|---|---|---|---|---|---|---|---|
| (Hz) | (Hz) | (Hz) | 60.05 | 60.55 | 61.04 | 61.54 | 62.04 | 62.53 | 63.03 | 63.52 | 64.02 | 64.52 |
| 1.00 | 1.00 | 1.05 | −87.00 | −87.25 | −85.06 | −83.90 | −86.50 | −88.74 | −85.75 | −86.50 | −90.34 | −90.38 |
| 1.10 | 1.05 | 1.16 | −87.00 | −87.25 | −85.06 | −83.90 | −86.50 | −88.74 | −85.75 | −86.50 | −90.34 | −90.38 |
| 1.21 | 1.16 | 1.27 | −86.92 | −87.10 | −84.88 | −83.74 | −86.28 | −88.68 | −85.62 | −86.52 | −90.37 | −90.23 |
| 1.33 | 1.27 | 1.40 | −86.60 | −86.52 | −84.18 | −83.13 | −85.47 | −88.46 | −85.10 | −86.63 | −90.50 | −89.67 |
| 1.47 | 1.40 | 1.54 | −86.88 | −86.53 | −84.00 | −83.00 | −85.23 | −88.00 | −85.06 | −86.66 | −90.24 | −89.41 |
| 1.62 | 1.54 | 1.70 | −87.63 | −86.57 | −83.59 | −82.69 | −84.70 | −87.09 | −84.96 | −86.74 | −89.67 | −88.86 |
| 1.78 | 1.70 | 1.87 | −87.60 | −86.06 | −83.16 | −81.86 | −84.08 | −85.81 | −84.26 | −86.05 | −89.17 | −89.40 |
| 1.96 | 1.87 | 2.06 | −87.03 | −85.37 | −82.84 | −81.55 | −83.76 | −84.96 | −83.64 | −85.51 | −88.64 | −89.63 |
| 2.15 | 2.06 | 2.26 | −85.85 | −84.38 | −82.52 | −81.63 | −83.60 | −84.31 | −82.90 | −84.89 | −87.90 | −89.44 |
| 2.37 | 2.26 | 2.49 | −84.76 | −83.86 | −82.47 | −82.23 | −83.61 | −83.88 | −82.26 | −83.91 | −87.16 | −88.13 |
| 2.61 | 2.49 | 2.74 | −83.81 | −83.01 | −82.44 | −82.71 | −84.24 | −84.52 | −82.91 | −84.35 | −87.51 | −88.42 |
| 2.87 | 2.74 | 3.02 | −82.93 | −82.06 | −82.26 | −82.83 | −83.71 | −84.74 | −84.30 | −85.33 | −87.86 | −89.72 |
| 3.16 | 3.02 | 3.32 | −82.13 | −81.63 | −82.47 | −83.08 | −82.99 | −83.55 | −84.79 | −85.57 | −86.90 | −88.47 |
| 3.48 | 3.32 | 3.66 | −82.15 | −81.62 | −82.42 | −82.95 | −82.17 | −82.50 | −83.96 | −84.40 | −85.45 | −88.85 |
| 3.83 | 3.66 | 4.02 | −82.14 | −82.13 | −83.11 | −82.04 | −81.02 | −82.64 | −83.36 | −82.46 | −83.06 | −87.94 |
| 4.22 | 4.02 | 4.43 | −81.15 | −80.99 | −81.99 | −81.37 | −80.80 | −81.24 | −82.18 | −82.56 | −83.86 | −88.04 |
| 4.64 | 4.43 | 4.88 | −81.32 | −80.53 | −80.43 | −80.51 | −80.08 | −81.23 | −82.42 | −82.03 | −84.34 | −87.75 |
| 5.11 | 4.88 | 5.37 | −79.42 | −78.72 | −79.68 | −79.49 | −78.54 | −79.70 | −82.41 | −82.53 | −83.22 | −87.50 |
| 5.62 | 5.37 | 5.91 | −79.19 | −77.64 | −79.28 | −79.31 | −77.90 | −78.71 | −81.34 | −76.20 | −76.45 | −85.85 |
| 6.19 | 5.91 | 6.50 | −79.04 | −73.96 | −73.30 | −72.89 | −72.44 | −74.58 | −77.54 | −72.13 | −72.76 | −85.48 |
| 6.81 | 6.50 | 7.16 | −76.69 | −72.58 | −71.33 | −70.35 | −70.09 | −71.80 | −75.33 | −71.91 | −73.09 | −85.66 |
| 7.50 | 7.16 | 7.88 | −76.21 | −73.33 | −74.35 | −74.03 | −73.74 | −74.02 | −76.83 | −76.31 | −78.21 | −85.77 |

TABLE 2-continued

| Bin Frequency (Hz) | Bin Start Frequency (Hz) | Bin Stop Frequency (Hz) | | | | | | | | | |
|---|---|---|---|---|---|---|---|---|---|---|---|
| 8.25 | 7.88 | 8.67 | −73.45 | −70.78 | −72.05 | −72.23 | −71.68 | −71.83 | −75.06 | −75.23 | −78.97 | −85.81 |
| 9.09 | 8.67 | 9.54 | −75.59 | −71.24 | −74.31 | −74.48 | −74.47 | −74.99 | −77.97 | −75.84 | −77.23 | −85.31 |
| 10.00 | 9.54 | 10.50 | −74.22 | −71.31 | −73.76 | −73.99 | −74.15 | −75.78 | −76.26 | −75.72 | −78.10 | −84.03 |
| 11.01 | 10.50 | 11.56 | −73.44 | −71.89 | −74.33 | −74.34 | −74.51 | −75.78 | −76.77 | −77.53 | −79.79 | −85.39 |
| 12.12 | 11.56 | 12.73 | −74.61 | −70.46 | −74.13 | −74.44 | −74.51 | −75.75 | −77.86 | −77.57 | −78.59 | −86.16 |
| 13.34 | 12.73 | 14.01 | −74.18 | −70.27 | −74.48 | −74.73 | −74.81 | −76.16 | −78.23 | −77.37 | −79.41 | −83.59 |
| 14.68 | 14.01 | 15.42 | −76.28 | −68.01 | −74.29 | −74.25 | −74.51 | −75.80 | −78.00 | −77.16 | −78.79 | −83.34 |
| 16.16 | 15.42 | 16.97 | −75.60 | −67.91 | −72.63 | −72.75 | −72.30 | −73.62 | −71.58 | −67.26 | −69.16 | −78.88 |
| 17.78 | 16.97 | 18.68 | −74.90 | −70.96 | −72.45 | −72.99 | −73.07 | −74.52 | −77.95 | −74.61 | −75.09 | −75.82 |
| 19.57 | 18.68 | 20.56 | −76.13 | −71.53 | −76.22 | −74.64 | −74.54 | −76.85 | −80.03 | −78.19 | −72.85 | −70.00 |
| 21.54 | 20.56 | 22.63 | −75.98 | −71.10 | −76.28 | −76.21 | −75.70 | −76.90 | −79.52 | −78.58 | −71.53 | −68.37 |
| 23.71 | 22.63 | 24.91 | −74.13 | −66.77 | −69.17 | −68.80 | −68.24 | −69.57 | −72.51 | −69.67 | −67.85 | −66.61 |
| 26.10 | 24.91 | 27.42 | −46.96 | −46.96 | −47.31 | −47.43 | −46.72 | −48.33 | −53.04 | −60.07 | −65.42 | −64.72 |
| 28.73 | 27.42 | 30.18 | −48.33 | −48.46 | −48.74 | −48.92 | −47.63 | −49.21 | −53.89 | −59.98 | −63.93 | −62.45 |
| 31.62 | 30.18 | 33.21 | −57.65 | −68.33 | −69.48 | −69.10 | −55.77 | −56.92 | −50.77 | −50.09 | −53.91 | −59.84 |
| 34.81 | 33.21 | 36.56 | −71.10 | −70.45 | −71.02 | −70.95 | −63.97 | −53.96 | −51.52 | −54.53 | −59.25 | −57.64 |
| 38.31 | 36.56 | 40.24 | −65.12 | −64.21 | −64.60 | −65.97 | −65.79 | −65.88 | −65.88 | −69.03 | −58.37 | −54.85 |
| 42.17 | 40.24 | 44.29 | −50.85 | −50.79 | −56.25 | −70.87 | −53.03 | −50.67 | −52.93 | −56.24 | −54.43 | −51.96 |
| 46.42 | 44.29 | 48.75 | −59.51 | −59.79 | −64.50 | −69.49 | −60.08 | −59.98 | −63.13 | −50.80 | −48.17 | −48.07 |
| 51.09 | 48.75 | 53.66 | −52.47 | −52.88 | −57.49 | −59.27 | −52.83 | −54.42 | −61.49 | −44.26 | −43.31 | −47.47 |
| 56.23 | 53.66 | 59.07 | −46.50 | −46.26 | −46.83 | −46.75 | −46.76 | −48.21 | −51.77 | −56.68 | −54.08 | −48.92 |
| 61.90 | 59.07 | 65.01 | −58.11 | −53.49 | −51.93 | −52.72 | −53.02 | −51.92 | −52.98 | −49.34 | −49.57 | −51.14 |
| 68.13 | 65.01 | 71.56 | −50.60 | −52.72 | −51.43 | −52.42 | −49.89 | −48.60 | −50.97 | −53.84 | −51.97 | −50.16 |
| 74.99 | 71.56 | 78.76 | −50.34 | −50.29 | −52.15 | −51.62 | −51.07 | −51.82 | −55.06 | −59.27 | −54.18 | −51.24 |
| 82.54 | 78.76 | 86.70 | −49.86 | −48.15 | −47.74 | −49.35 | −49.89 | −48.55 | −49.54 | −51.11 | −48.56 | −43.44 |
| 90.85 | 86.70 | 95.43 | −52.91 | −51.51 | −50.93 | −51.14 | −51.48 | −50.10 | −48.59 | −49.19 | −52.11 | −51.11 |
| 100.00 | 95.43 | 105.03 | −51.59 | −50.61 | −52.51 | −49.49 | −49.38 | −51.50 | −49.63 | −46.37 | −46.21 | −48.50 |
| 110.07 | 105.03 | 115.61 | −45.97 | −45.17 | −45.47 | −45.03 | −44.99 | −46.47 | −47.76 | −50.36 | −51.53 | −47.86 |
| 121.15 | 115.61 | 127.25 | −54.40 | −48.72 | −47.11 | −47.03 | −48.19 | −49.55 | −50.95 | −49.27 | −48.12 | −47.27 |
| 133.35 | 127.25 | 140.07 | −50.73 | −51.39 | −50.80 | −49.73 | −49.66 | −49.56 | −51.80 | −55.83 | −57.17 | −56.80 |
| 146.78 | 140.07 | 154.17 | −55.18 | −55.25 | −56.71 | −56.07 | −55.23 | −56.52 | −60.57 | −60.07 | −58.76 | −58.36 |

(section 26 of 28): Time-Frequency Spectral Analysis Results

| Bin Frequency (Hz) | Bin Start Frequency (Hz) | Bin Stop Frequency (Hz) | Average Signal Power Density per Bin Width (dBfs/Hz) vs Time and Frequency Time (min): | | | | | | | | | |
|---|---|---|---|---|---|---|---|---|---|---|---|
| | | | 60.05 | 60.55 | 61.04 | 61.54 | 62.04 | 62.53 | 63.03 | 63.52 | 64.02 | 64.52 |
| 161.56 | 154.17 | 169.69 | −47.24 | −46.36 | −46.15 | −47.45 | −47.99 | −47.42 | −47.93 | −49.37 | −51.30 | −51.17 |
| 177.83 | 169.69 | 186.78 | −57.25 | −50.33 | −48.50 | −49.15 | −49.67 | −50.32 | −47.74 | −47.53 | −53.63 | −57.09 |
| 195.73 | 186.78 | 205.59 | −51.18 | −55.47 | −51.91 | −49.48 | −50.25 | −51.33 | −49.94 | −49.39 | −50.64 | −53.10 |
| 215.44 | 205.59 | 226.29 | −49.26 | −47.47 | −46.94 | −47.86 | −48.31 | −47.81 | −45.93 | −47.28 | −53.19 | −50.01 |
| 237.14 | 226.29 | 249.08 | −57.64 | −54.19 | −52.40 | −52.58 | −53.16 | −54.02 | −54.34 | −54.64 | −54.27 | −53.16 |
| 261.02 | 249.08 | 274.16 | −51.05 | −53.61 | −49.99 | −49.95 | −49.99 | −50.96 | −52.39 | −49.97 | −51.45 | −55.53 |
| 287.30 | 274.16 | 301.76 | −57.15 | −55.62 | −52.44 | −51.37 | −51.99 | −52.46 | −53.01 | −53.97 | −57.05 | −57.98 |
| 316.23 | 301.76 | 332.15 | −55.76 | −54.48 | −50.95 | −48.88 | −49.59 | −52.81 | −53.25 | −54.53 | −53.97 | −55.30 |
| 348.07 | 332.15 | 365.59 | −59.06 | −50.84 | −49.10 | −50.60 | −52.20 | −54.62 | −51.80 | −51.74 | −56.17 | −58.46 |
| 383.12 | 365.59 | 402.41 | −55.15 | −54.94 | −54.75 | −51.65 | −53.80 | −50.70 | −50.16 | −54.05 | −58.42 | −61.55 |
| 421.70 | 402.41 | 442.93 | −57.78 | −55.51 | −56.18 | −60.23 | −56.20 | −54.43 | −54.71 | −55.40 | −61.18 | −58.20 |
| 464.16 | 442.93 | 487.53 | −60.81 | −57.51 | −58.00 | −64.17 | −62.40 | −60.89 | −61.12 | −61.51 | −66.86 | −63.53 |
| 510.90 | 487.53 | 536.62 | −54.51 | −53.29 | −53.70 | −54.66 | −55.96 | −59.00 | −55.72 | −55.92 | −60.38 | −61.55 |
| 562.34 | 536.62 | 590.65 | −63.34 | −61.45 | −54.76 | −54.31 | −57.62 | −58.63 | −58.77 | −60.07 | −63.30 | −62.20 |
| 618.97 | 590.65 | 650.13 | −67.01 | −66.30 | −59.09 | −58.53 | −60.45 | −60.58 | −59.41 | −60.73 | −66.38 | −66.03 |
| 681.29 | 650.13 | 715.59 | −54.84 | −53.28 | −54.42 | −54.21 | −55.86 | −55.88 | −51.22 | −54.23 | −63.18 | −65.37 |
| 749.89 | 715.59 | 787.65 | −63.75 | −61.78 | −62.22 | −57.76 | −58.16 | −54.75 | −57.28 | −60.99 | −63.90 | −70.21 |
| 825.40 | 787.65 | 866.96 | −67.48 | −66.45 | −64.54 | −62.85 | −62.65 | −60.09 | −61.43 | −63.00 | −67.18 | −71.26 |
| 908.52 | 866.96 | 954.26 | −62.10 | −61.33 | −60.61 | −61.55 | −59.61 | −58.68 | −61.74 | −65.32 | −70.00 | −73.44 |
| 1000.00 | 954.26 | 1050.35 | −58.28 | −62.91 | −60.33 | −56.58 | −57.07 | −61.61 | −60.12 | −60.63 | −64.34 | −71.53 |
| 1100.69 | 1050.35 | 1156.11 | −64.17 | −67.01 | −67.09 | −62.10 | −63.18 | −65.33 | −63.94 | −66.74 | −72.43 | −73.37 |
| 1211.53 | 1156.11 | 1272.52 | −66.29 | −65.86 | −63.14 | −62.44 | −64.46 | −59.71 | −59.78 | −64.29 | −71.47 | −72.01 |
| 1333.52 | 1272.52 | 1400.66 | −61.11 | −63.16 | −68.80 | −63.37 | −63.95 | −63.25 | −59.98 | −64.60 | −71.54 | −71.78 |
| 1467.80 | 1400.66 | 1541.70 | −65.52 | −76.56 | −75.22 | −71.10 | −71.77 | −68.63 | −67.18 | −68.97 | −75.91 | −72.63 |
| 1615.60 | 1541.70 | 1696.94 | −65.36 | −73.93 | −75.42 | −73.42 | −71.40 | −63.97 | −67.08 | −75.02 | −77.41 | −72.40 |
| 1778.28 | 1696.94 | 1867.81 | −68.91 | −70.99 | −75.40 | −77.04 | −78.06 | −74.94 | −73.67 | −80.50 | −78.67 | −76.49 |
| 1957.34 | 1867.81 | 2055.89 | −69.50 | −77.38 | −76.78 | −76.54 | −78.91 | −78.50 | −75.41 | −78.01 | −81.21 | −78.47 |
| 2154.43 | 2055.89 | 2262.90 | −69.90 | −77.39 | −77.67 | −77.80 | −77.67 | −81.68 | −79.57 | −80.78 | −83.11 | −79.59 |
| 2371.37 | 2262.90 | 2490.77 | −80.74 | −80.65 | −79.94 | −80.86 | −80.96 | −79.11 | −81.85 | −86.17 | −79.46 | −76.18 |
| 2610.16 | 2490.77 | 2741.57 | −81.27 | −82.39 | −80.46 | −78.74 | −78.97 | −81.57 | −81.95 | −83.76 | −81.26 | −78.19 |
| 2872.98 | 2741.57 | 3017.63 | −82.86 | −81.92 | −79.56 | −78.84 | −78.72 | −80.03 | −80.98 | −81.93 | −83.57 | −81.65 |
| 3162.28 | 3017.63 | 3321.49 | −82.51 | −83.85 | −83.03 | −80.44 | −80.71 | −82.32 | −81.99 | −82.44 | −83.87 | −84.27 |
| 3480.70 | 3321.49 | 3655.94 | −84.42 | −85.12 | −83.91 | −80.35 | −81.70 | −81.92 | −81.69 | −83.48 | −85.07 | −83.37 |
| 3831.19 | 3655.94 | 4024.08 | −85.75 | −86.81 | −85.20 | −84.08 | −83.91 | −83.49 | −84.10 | −85.52 | −85.53 | −82.57 |
| 4216.97 | 4024.08 | 4429.28 | −85.48 | −88.97 | −88.39 | −85.16 | −85.26 | −86.75 | −87.33 | −88.54 | −88.17 | −86.00 |
| 4641.59 | 4429.28 | 4875.28 | −87.21 | −91.68 | −91.28 | −88.58 | −90.54 | −88.96 | −89.07 | −91.94 | −88.26 | −84.70 |
| 5108.97 | 4875.28 | 5366.19 | −85.97 | −92.79 | −91.47 | −91.60 | −93.17 | −93.54 | −92.83 | −93.25 | −86.77 | −82.00 |
| 5623.41 | 5366.19 | 5906.54 | −91.08 | −93.28 | −92.11 | −91.73 | −94.20 | −93.84 | −93.50 | −94.42 | −88.10 | −82.49 |
| 6189.66 | 5906.54 | 6501.29 | −93.39 | −94.90 | −92.84 | −91.75 | −94.26 | −96.04 | −94.64 | −94.27 | −86.47 | −81.27 |
| 6812.92 | 6501.29 | 7155.93 | −96.61 | −96.35 | −94.39 | −92.83 | −94.78 | −96.23 | −95.25 | −94.69 | −87.37 | −81.91 |
| 7498.94 | 7155.93 | 7876.49 | −99.61 | −97.51 | −95.02 | −93.92 | −96.20 | −97.30 | −96.12 | −95.33 | −90.81 | −84.90 |

TABLE 2-continued

| | | | | | | | | | | |
|---|---|---|---|---|---|---|---|---|---|---|
| 8254.04 | 7876.49 | 8669.61 | −99.76 | −97.37 | −95.07 | −93.89 | −96.23 | −96.92 | −96.23 | −95.52 | −88.78 | −83.90 |
| 9085.18 | 8669.61 | 9542.59 | −100.40 | −98.51 | −96.17 | −94.39 | −95.48 | −96.41 | −95.84 | −95.71 | −89.08 | −82.97 |
| 10000.00 | 9542.59 | 10503.47 | −101.51 | −99.96 | −98.24 | −96.46 | −96.80 | −97.41 | −96.56 | −97.22 | −91.31 | −84.42 |
| 11006.94 | 10503.47 | 11561.11 | −101.96 | −100.57 | −99.97 | −98.40 | −100.04 | −97.94 | −96.82 | −98.77 | −92.89 | −86.29 |
| 12115.28 | 11561.11 | 12725.25 | −104.18 | −103.13 | −102.77 | −100.89 | −102.76 | −100.59 | −99.47 | −101.96 | −93.85 | −88.39 |
| 13335.21 | 12725.25 | 14006.60 | −107.49 | −106.20 | −105.90 | −104.34 | −105.81 | −103.77 | −102.54 | −104.90 | −94.52 | −89.39 |
| 14677.99 | 14006.60 | 15416.99 | −109.98 | −108.72 | −108.68 | −107.43 | −108.89 | −106.12 | −105.98 | −108.36 | −96.60 | −90.63 |
| 16155.98 | 15416.99 | 16969.39 | −113.91 | −111.75 | −111.37 | −110.41 | −111.95 | −112.37 | −112.33 | −112.26 | −98.15 | −91.45 |
| 17782.79 | 16969.39 | 18678.11 | −115.76 | −113.58 | −112.74 | −112.58 | −113.71 | −115.48 | −115.43 | −114.96 | −101.19 | −94.51 |
| 19573.42 | 18678.11 | 20558.88 | −115.62 | −114.47 | −114.08 | −113.91 | −114.35 | −115.57 | −115.90 | −115.92 | −103.27 | −96.77 |
| 21544.35 | 20558.88 | 22629.04 | −114.72 | −115.01 | −114.91 | −115.06 | −115.32 | −115.84 | −116.86 | −118.11 | −107.81 | −99.87 |

(section 27 of 28): Time-Frequency Spectral Analysis Results

| Bin Frequency | Bin Start Frequency | Bin Stop Frequency | Average Signal Power Density per Bin Width (dBfs/Hz) vs Time and Frequency Time (min): | | | | | |
|---|---|---|---|---|---|---|---|---|
| (Hz) | (Hz) | (Hz) | 65.01 | 65.51 | 66.01 | 66.50 | 67.00 | 67.50 |
| 1.00 | 1.00 | 1.05 | −88.28 | −86.11 | −86.34 | −84.17 | −84.83 | −88.16 |
| 1.10 | 1.05 | 1.16 | −88.28 | −86.11 | −86.34 | −84.17 | −84.83 | −88.16 |
| 1.21 | 1.16 | 1.27 | −88.26 | −86.08 | −86.35 | −84.27 | −84.99 | −88.11 |
| 1.33 | 1.27 | 1.40 | −88.14 | −85.94 | −86.36 | −84.69 | −85.69 | −87.92 |
| 1.47 | 1.40 | 1.54 | −88.02 | −85.93 | −86.10 | −84.53 | −85.54 | −87.77 |
| 1.62 | 1.54 | 1.70 | −87.74 | −85.90 | −85.53 | −84.19 | −85.20 | −87.43 |
| 1.78 | 1.70 | 1.87 | −87.65 | −85.95 | −86.09 | −84.40 | −85.41 | −87.93 |
| 1.96 | 1.87 | 2.06 | −87.61 | −85.81 | −86.36 | −84.16 | −85.17 | −88.21 |
| 2.15 | 2.06 | 2.26 | −87.59 | −85.43 | −86.20 | −83.36 | −84.36 | −88.20 |
| 2.37 | 2.26 | 2.49 | −87.14 | −84.92 | −84.67 | −82.33 | −83.16 | −87.04 |
| 2.61 | 2.49 | 2.74 | −87.16 | −84.94 | −84.91 | −83.42 | −84.77 | −87.79 |
| 2.87 | 2.74 | 3.02 | −87.52 | −85.37 | −86.28 | −84.95 | −85.85 | −88.25 |
| 3.16 | 3.02 | 3.32 | −86.60 | −84.88 | −84.81 | −82.89 | −83.20 | −85.73 |
| 3.48 | 3.32 | 3.66 | −87.24 | −85.48 | −85.35 | −83.69 | −84.61 | −87.11 |
| 3.83 | 3.66 | 4.02 | −87.40 | −85.31 | −84.92 | −83.49 | −84.40 | −87.59 |
| 4.22 | 4.02 | 4.43 | −87.25 | −84.70 | −84.51 | −82.77 | −83.75 | −87.39 |
| 4.64 | 4.43 | 4.88 | −86.20 | −83.70 | −84.00 | −82.97 | −84.69 | −87.54 |
| 5.11 | 4.88 | 5.37 | −86.40 | −84.06 | −83.77 | −81.82 | −83.42 | −87.34 |
| 5.62 | 5.37 | 5.91 | −84.95 | −83.26 | −83.23 | −81.03 | −82.31 | −86.45 |
| 6.19 | 5.91 | 6.50 | −83.08 | −81.09 | −81.55 | −80.79 | −81.98 | −84.77 |
| 6.81 | 6.50 | 7.16 | −83.24 | −81.12 | −80.86 | −80.71 | −82.12 | −85.07 |
| 7.50 | 7.16 | 7.88 | −84.14 | −81.38 | −80.04 | −80.19 | −82.11 | −85.45 |
| 8.25 | 7.88 | 8.67 | −83.08 | −80.76 | −80.52 | −80.99 | −82.55 | −84.77 |
| 9.09 | 8.67 | 9.54 | −80.33 | −77.08 | −77.69 | −79.31 | −80.84 | −84.18 |
| 10.00 | 9.54 | 10.50 | −77.57 | −75.09 | −74.66 | −75.46 | −78.92 | −83.45 |
| 11.01 | 10.50 | 11.56 | −77.96 | −73.29 | −73.95 | −76.87 | −78.60 | −83.64 |
| 12.12 | 11.56 | 12.73 | −81.14 | −77.23 | −76.18 | −77.46 | −79.65 | −83.71 |
| 13.34 | 12.73 | 14.01 | −79.67 | −77.14 | −75.83 | −76.48 | −77.98 | −81.03 |
| 14.68 | 14.01 | 15.42 | −80.07 | −78.44 | −77.31 | −76.90 | −78.31 | −81.54 |
| 16.16 | 15.42 | 16.97 | −77.08 | −74.70 | −73.68 | −73.44 | −73.43 | −75.90 |
| 17.78 | 16.97 | 18.68 | −74.09 | −72.94 | −72.57 | −72.50 | −72.20 | −74.21 |
| 19.57 | 18.68 | 20.56 | −68.84 | −67.66 | −67.44 | −68.14 | −68.05 | −69.94 |
| 21.54 | 20.56 | 22.63 | −67.11 | −65.87 | −65.56 | −65.77 | −66.00 | −67.93 |
| 23.71 | 22.63 | 24.91 | −65.23 | −63.79 | −63.59 | −63.88 | −64.14 | −66.22 |
| 26.10 | 24.91 | 27.42 | −63.82 | −62.37 | −61.99 | −62.03 | −62.10 | −64.29 |
| 28.73 | 27.42 | 30.18 | −61.90 | −60.52 | −60.25 | −60.30 | −60.52 | −62.66 |
| 31.62 | 30.18 | 33.21 | −59.67 | −58.68 | −58.69 | −59.36 | −59.74 | −61.93 |
| 34.81 | 33.21 | 36.56 | −56.67 | −56.27 | −56.81 | −58.15 | −58.59 | −59.89 |
| 38.31 | 36.56 | 40.24 | −54.80 | −53.21 | −53.58 | −56.62 | −56.61 | −58.46 |
| 42.17 | 40.24 | 44.29 | −52.16 | −49.70 | −49.61 | −51.96 | −53.02 | −56.30 |
| 46.42 | 44.29 | 48.75 | −46.03 | −46.17 | −48.12 | −47.09 | −47.56 | −51.43 |
| 51.09 | 48.75 | 53.66 | −45.34 | −45.32 | −45.73 | −44.29 | −44.52 | −46.90 |
| 56.23 | 53.66 | 59.07 | −48.18 | −48.59 | −47.70 | −48.43 | −49.17 | −51.01 |
| 61.90 | 59.07 | 65.01 | −50.68 | −50.56 | −50.38 | −49.75 | −50.30 | −52.04 |
| 68.13 | 65.01 | 71.56 | −47.25 | −47.31 | −48.15 | −48.78 | −49.66 | −50.87 |
| 74.99 | 71.56 | 78.76 | −49.07 | −48.63 | −49.10 | −49.36 | −49.30 | −51.04 |
| 82.54 | 78.76 | 86.70 | −43.88 | −45.36 | −45.11 | −46.06 | −47.28 | −47.96 |
| 90.85 | 86.70 | 95.43 | −47.31 | −47.02 | −48.74 | −46.66 | −46.75 | −50.35 |
| 100.00 | 95.43 | 105.03 | −44.60 | −44.30 | −45.35 | −44.06 | −44.06 | −45.26 |
| 110.07 | 105.03 | 115.61 | −47.13 | −47.28 | −46.70 | −48.17 | −48.71 | −48.82 |
| 121.15 | 115.61 | 127.25 | −47.57 | −46.93 | −46.89 | −48.37 | −50.23 | −51.05 |
| 133.35 | 127.25 | 140.07 | −51.66 | −50.39 | −50.14 | −49.99 | −50.99 | −52.88 |
| 146.78 | 140.07 | 154.17 | −56.96 | −54.49 | −53.79 | −54.15 | −55.20 | −56.72 |

TABLE 2-continued (section 28 of 28): Time-Frequency Spectral Analysis Results

| Bin Frequency (Hz) | Bin Start Frequency (Hz) | Bin Stop Frequency (Hz) | Average Signal Power Density per Bin Width (dBfs/Hz) vs Time and Frequency Time (min): | | | | | |
|---|---|---|---|---|---|---|---|---|
| | | | 65.01 | 65.51 | 66.01 | 66.50 | 67.00 | 67.50 |
| 161.56 | 154.17 | 169.69 | −50.60 | −48.37 | −47.87 | −49.98 | −50.91 | −52.38 |
| 177.83 | 169.69 | 186.78 | −54.43 | −53.94 | −53.25 | −53.02 | −53.76 | −54.42 |
| 195.73 | 186.78 | 205.59 | −52.32 | −52.52 | −52.33 | −52.59 | −52.90 | −54.06 |
| 215.44 | 205.59 | 226.29 | −47.15 | −47.34 | −47.32 | −47.91 | −48.80 | −49.55 |
| 237.14 | 226.29 | 249.08 | −51.93 | −51.44 | −50.99 | −50.09 | −50.76 | −52.39 |
| 261.02 | 249.08 | 274.16 | −55.58 | −56.22 | −55.27 | −55.32 | −56.02 | −57.33 |
| 287.30 | 274.16 | 301.76 | −52.79 | −53.31 | −54.87 | −54.82 | −55.31 | −57.28 |
| 316.23 | 301.76 | 332.15 | −52.06 | −51.36 | −53.26 | −52.87 | −53.64 | −55.00 |
| 348.07 | 332.15 | 365.59 | −54.15 | −53.76 | −56.33 | −56.10 | −56.96 | −58.15 |
| 383.12 | 365.59 | 402.41 | −55.51 | −54.20 | −56.85 | −57.22 | −57.67 | −58.43 |
| 421.70 | 402.41 | 442.93 | −56.94 | −56.33 | −55.86 | −57.69 | −58.62 | −59.16 |
| 464.16 | 442.93 | 487.53 | −62.88 | −60.55 | −59.74 | −61.11 | −62.05 | −66.11 |
| 510.90 | 487.53 | 536.62 | −60.18 | −60.33 | −59.91 | −59.49 | −59.87 | −61.36 |
| 562.34 | 536.62 | 590.65 | −60.26 | −60.52 | −59.43 | −59.49 | −59.58 | −61.43 |
| 618.97 | 590.65 | 650.13 | −62.61 | −62.70 | −61.34 | −61.24 | −60.51 | −61.03 |
| 681.29 | 650.13 | 715.59 | −62.18 | −61.34 | −61.49 | −62.20 | −60.03 | −60.86 |
| 749.89 | 715.59 | 787.65 | −66.02 | −65.77 | −65.52 | −65.06 | −64.71 | −65.09 |
| 825.40 | 787.65 | 866.96 | −69.39 | −67.94 | −66.26 | −66.74 | −65.87 | −67.58 |
| 908.52 | 866.96 | 954.26 | −70.49 | −68.04 | −67.44 | −69.07 | −69.08 | −70.32 |
| 1000.00 | 954.26 | 1050.35 | −69.87 | −68.10 | −67.14 | −66.93 | −66.51 | −67.41 |
| 1100.69 | 1050.35 | 1156.11 | −69.41 | −68.37 | −68.22 | −68.84 | −68.57 | −69.35 |
| 1211.53 | 1156.11 | 1272.52 | −68.77 | −68.27 | −68.71 | −68.29 | −66.95 | −68.14 |
| 1333.52 | 1272.52 | 1400.66 | −71.36 | −68.67 | −67.30 | −66.67 | −64.52 | −65.76 |
| 1467.80 | 1400.66 | 1541.70 | −70.54 | −70.03 | −68.25 | −67.00 | −66.45 | −67.71 |
| 1615.60 | 1541.70 | 1696.94 | −70.95 | −72.01 | −70.32 | −70.65 | −68.83 | −68.98 |
| 1778.28 | 1696.94 | 1867.81 | −74.65 | −73.52 | −71.52 | −70.99 | −70.96 | −71.85 |
| 1957.34 | 1867.81 | 2055.89 | −74.37 | −73.78 | −72.45 | −70.41 | −70.28 | −71.55 |
| 2154.43 | 2055.89 | 2262.90 | −76.27 | −75.33 | −74.93 | −75.28 | −74.26 | −74.87 |
| 2371.37 | 2262.90 | 2490.77 | −75.55 | −76.14 | −75.90 | −76.38 | −76.11 | −77.18 |
| 2610.16 | 2490.77 | 2741.57 | −76.12 | −75.70 | −75.59 | −75.68 | −75.30 | −76.75 |
| 2872.98 | 2741.57 | 3017.63 | −78.71 | −77.72 | −77.12 | −76.61 | −76.14 | −77.84 |
| 3162.28 | 3017.63 | 3321.49 | −80.04 | −78.66 | −78.42 | −77.34 | −76.77 | −78.61 |
| 3480.70 | 3321.49 | 3655.94 | −78.85 | −78.72 | −78.77 | −76.97 | −76.49 | −78.58 |
| 3831.19 | 3655.94 | 4024.08 | −80.19 | −79.79 | −77.08 | −75.93 | −75.21 | −76.53 |
| 4216.97 | 4024.08 | 4429.28 | −82.60 | −81.43 | −80.08 | −79.91 | −78.80 | −79.42 |
| 4641.59 | 4429.28 | 4875.28 | −81.06 | −80.41 | −79.76 | −78.93 | −78.32 | −79.83 |
| 5108.97 | 4875.28 | 5366.19 | −79.91 | −80.19 | −79.24 | −79.01 | −78.19 | −79.64 |
| 5623.41 | 5366.19 | 5906.54 | −80.35 | −80.49 | −79.97 | −79.53 | −79.00 | −80.48 |
| 6189.66 | 5906.54 | 6501.29 | −79.43 | −79.45 | −79.19 | −78.86 | −78.51 | −80.06 |
| 6812.92 | 6501.29 | 7155.93 | −80.30 | −80.75 | −80.15 | −79.69 | −79.57 | −81.29 |
| 7498.94 | 7155.93 | 7876.49 | −82.40 | −82.85 | −81.94 | −81.26 | −81.04 | −82.41 |
| 8254.04 | 7876.49 | 8669.61 | −81.73 | −81.65 | −80.74 | −80.56 | −80.11 | −81.18 |
| 9085.18 | 8669.61 | 9542.59 | −81.10 | −81.79 | −80.69 | −80.50 | −80.60 | −82.21 |
| 10000.00 | 9542.59 | 10503.47 | −82.42 | −83.02 | −82.02 | −82.01 | −82.28 | −83.73 |
| 11006.94 | 10503.47 | 11561.11 | −84.21 | −84.45 | −83.61 | −83.33 | −83.14 | −84.66 |
| 12115.28 | 11561.11 | 12725.25 | −86.41 | −85.81 | −85.20 | −84.88 | −84.40 | −86.16 |
| 13335.21 | 12725.25 | 14006.60 | −87.07 | −86.02 | −85.64 | −85.26 | −85.27 | −87.72 |
| 14677.99 | 14006.60 | 15416.99 | −88.15 | −87.41 | −86.95 | −86.72 | −86.43 | −88.77 |
| 16155.98 | 15416.99 | 16969.39 | −88.98 | −88.38 | −87.74 | −87.59 | −87.54 | −89.97 |
| 17782.79 | 16969.39 | 18678.11 | −91.89 | −90.81 | −89.97 | −90.02 | −90.23 | −92.77 |
| 19573.42 | 18678.11 | 20558.88 | −94.60 | −93.90 | −93.17 | −92.80 | −92.51 | −94.88 |
| 21544.35 | 20558.88 | 22629.04 | −96.26 | −94.58 | −94.23 | −94.53 | −94.75 | −97.68 |

TABLE 3

(section 1 of 1): Average Spectral Analysis over Entire Duration

| Bin Frequency (Hz) | Bin Start Frequency (Hz) | Bin Stop Frequency (Hz) | Average Signal Power Density (dBfs/Hz) |
|---|---|---|---|
| 1.00 | 1.00 | 1.05 | −80.09 |
| 1.10 | 1.05 | 1.16 | −80.09 |
| 1.21 | 1.16 | 1.27 | −80.19 |
| 1.33 | 1.27 | 1.40 | −80.60 |
| 1.47 | 1.40 | 1.54 | −80.75 |
| 1.62 | 1.54 | 1.70 | −81.14 |
| 1.78 | 1.70 | 1.87 | −80.51 |
| 1.96 | 1.87 | 2.06 | −79.88 |
| 2.15 | 2.06 | 2.26 | −79.11 |
| 2.37 | 2.26 | 2.49 | −79.14 |
| 2.61 | 2.49 | 2.74 | −79.69 |
| 2.87 | 2.74 | 3.02 | −79.53 |
| 3.16 | 3.02 | 3.32 | −79.09 |
| 3.48 | 3.32 | 3.66 | −78.75 |
| 3.83 | 3.66 | 4.02 | −76.34 |
| 4.22 | 4.02 | 4.43 | −76.27 |

TABLE 3-continued (section 1 of 1): Average Spectral Analysis over Entire Duration

| Bin Frequency (Hz) | Bin Start Frequency (Hz) | Bin Stop Frequency (Hz) | Average Signal Power Density (dBfs/Hz) |
|---|---|---|---|
| 4.64 | 4.43 | 4.88 | −77.85 |
| 5.11 | 4.88 | 5.37 | −77.95 |
| 5.62 | 5.37 | 5.91 | −76.64 |
| 6.19 | 5.91 | 6.50 | −75.33 |
| 6.81 | 6.50 | 7.16 | −75.57 |
| 7.50 | 7.16 | 7.88 | −74.89 |
| 8.25 | 7.88 | 8.67 | −72.78 |
| 9.09 | 8.67 | 9.54 | −72.33 |
| 10.00 | 9.54 | 10.50 | −70.67 |
| 11.01 | 10.50 | 11.56 | −68.66 |
| 12.12 | 11.56 | 12.73 | −68.89 |
| 13.34 | 12.73 | 14.01 | −68.71 |
| 14.68 | 14.01 | 15.42 | −69.48 |
| 16.16 | 15.42 | 16.97 | −67.00 |
| 17.78 | 16.97 | 18.68 | −64.06 |
| 19.57 | 18.68 | 20.56 | −63.47 |
| 21.54 | 20.56 | 22.63 | −64.04 |
| 23.71 | 22.63 | 24.91 | −62.23 |
| 26.10 | 24.91 | 27.42 | −51.31 |
| 28.73 | 27.42 | 30.18 | −52.01 |
| 31.62 | 30.18 | 33.21 | −52.26 |
| 34.81 | 33.21 | 36.56 | −47.22 |
| 38.31 | 36.56 | 40.24 | −44.81 |
| 42.17 | 40.24 | 44.29 | −42.16 |
| 46.42 | 44.29 | 48.75 | −45.11 |
| 51.09 | 48.75 | 53.66 | −41.29 |
| 56.23 | 53.66 | 59.07 | −40.74 |
| 61.90 | 59.07 | 65.01 | −42.91 |
| 68.13 | 65.01 | 71.56 | −40.57 |
| 74.99 | 71.56 | 78.76 | −40.62 |
| 82.54 | 78.76 | 86.70 | −39.79 |
| 90.85 | 86.70 | 95.43 | −46.46 |
| 100.00 | 95.43 | 105.03 | −43.58 |
| 110.07 | 105.03 | 115.61 | −44.12 |
| 121.15 | 115.61 | 127.25 | −48.27 |
| 133.35 | 127.25 | 140.07 | −47.38 |
| 146.78 | 140.07 | 154.17 | −46.99 |
| 161.56 | 154.17 | 169.69 | −45.13 |
| 177.83 | 169.69 | 186.78 | −47.37 |
| 195.73 | 186.78 | 205.59 | −46.92 |
| 215.44 | 205.59 | 226.29 | −46.29 |
| 237.14 | 226.29 | 249.08 | −49.17 |
| 261.02 | 249.08 | 274.16 | −48.11 |
| 287.30 | 274.16 | 301.76 | −48.31 |
| 316.23 | 301.76 | 332.15 | −49.96 |
| 348.07 | 332.15 | 365.59 | −51.23 |
| 383.12 | 365.59 | 402.41 | −50.08 |
| 421.70 | 402.41 | 442.93 | −51.47 |
| 464.16 | 442.93 | 487.53 | −56.34 |
| 510.90 | 487.53 | 536.62 | −50.43 |
| 562.34 | 536.62 | 590.65 | −54.03 |
| 618.97 | 590.65 | 650.13 | −56.39 |
| 681.29 | 650.13 | 715.59 | −52.90 |
| 749.89 | 715.59 | 787.65 | −56.51 |
| 825.40 | 787.65 | 866.96 | −58.43 |
| 908.52 | 866.96 | 954.26 | −56.72 |
| 1000.00 | 954.26 | 1050.35 | −56.86 |
| 1100.69 | 1050.35 | 1156.11 | −60.11 |
| 1211.53 | 1156.11 | 1272.52 | −60.09 |
| 1333.52 | 1272.52 | 1400.66 | −61.26 |
| 1467.80 | 1400.66 | 1541.70 | −64.77 |
| 1615.60 | 1541.70 | 1696.94 | −64.75 |
| 1778.28 | 1696.94 | 1867.81 | −66.00 |
| 1957.34 | 1867.81 | 2055.89 | −68.77 |
| 2154.43 | 2055.89 | 2262.90 | −69.28 |
| 2371.37 | 2262.90 | 2490.77 | −70.37 |
| 2610.16 | 2490.77 | 2741.57 | −70.97 |
| 2872.98 | 2741.57 | 3017.63 | −72.52 |
| 3162.28 | 3017.63 | 3321.49 | −73.85 |
| 3480.70 | 3321.49 | 3655.94 | −75.06 |
| 3831.19 | 3655.94 | 4024.08 | −76.77 |
| 4216.97 | 4024.08 | 4429.28 | −77.91 |
| 4641.59 | 4429.28 | 4875.28 | −79.94 |
| 5108.97 | 4875.28 | 5366.19 | −80.18 |
| 5623.41 | 5366.19 | 5906.54 | −82.39 |
| 6189.66 | 5906.54 | 6501.29 | −83.23 |
| 6812.92 | 6501.29 | 7155.93 | −83.18 |
| 7498.94 | 7155.93 | 7876.49 | −85.97 |
| 8254.04 | 7876.49 | 8669.61 | −86.80 |
| 9085.18 | 8669.61 | 9542.59 | −87.48 |
| 10000.00 | 9542.59 | 10503.47 | −89.28 |
| 11006.94 | 10503.47 | 11561.11 | −90.95 |
| 12115.28 | 11561.11 | 12725.25 | −92.15 |
| 13335.21 | 12725.25 | 14006.60 | −93.97 |
| 14677.99 | 14006.60 | 15416.99 | −95.64 |
| 16155.98 | 15416.99 | 16969.39 | −98.27 |
| 17782.79 | 16969.39 | 18678.11 | −101.21 |
| 19573.42 | 18678.11 | 20558.88 | −104.35 |
| 21544.35 | 20558.88 | 22629.04 | −107.45 |

TABLE 4

(section 1 of 1): Signal Envelope over Time

| Time (min) | Positive Envelope Amplitude | Negative Envelope Amplitude |
|---|---|---|
| 0.50 | 0.7791 | −0.7004 |
| 0.99 | 0.7823 | −0.8595 |
| 1.49 | 0.8426 | −0.8993 |
| 1.99 | 0.8426 | −0.8993 |
| 2.48 | 0.9424 | −0.9486 |
| 2.98 | 0.9424 | −0.9621 |
| 3.47 | 0.8976 | −0.9621 |
| 3.97 | 0.9602 | −1.0000 |
| 4.47 | 0.9602 | −1.0000 |
| 4.96 | 0.9442 | −0.8798 |
| 5.46 | 0.9442 | −0.8991 |
| 5.96 | 0.8430 | −0.8991 |
| 6.45 | 0.8919 | −0.8569 |
| 6.95 | 1.0000 | −1.0000 |
| 7.44 | 1.0000 | −1.0000 |
| 7.94 | 1.0000 | −1.0000 |
| 8.44 | 0.9948 | −1.0000 |
| 8.93 | 0.8536 | −0.8849 |
| 9.43 | 0.8536 | −0.8693 |
| 9.93 | 0.7428 | −0.7696 |
| 10.42 | 0.9570 | −0.9014 |
| 10.92 | 0.9570 | −0.9014 |
| 11.41 | 0.8197 | −0.8453 |
| 11.91 | 0.6930 | −0.7174 |
| 12.41 | 0.9034 | −0.7469 |
| 12.90 | 0.9034 | −0.7613 |
| 13.40 | 0.9062 | −0.9593 |
| 13.90 | 0.9062 | −0.9593 |
| 14.39 | 0.8192 | −0.8081 |
| 14.89 | 0.7234 | −0.6668 |
| 15.38 | 0.7067 | −0.6668 |
| 15.88 | 0.4704 | −0.4312 |
| 16.38 | 0.4556 | −0.4312 |
| 16.87 | 0.5567 | −0.4867 |
| 17.37 | 0.5567 | −0.5208 |
| 17.87 | 0.5445 | −0.5451 |
| 18.36 | 0.5572 | −0.5559 |
| 18.86 | 0.5572 | −0.5559 |
| 19.36 | 0.4006 | −0.4489 |
| 19.85 | 0.6251 | −0.5329 |
| 20.35 | 0.6251 | −0.5329 |
| 20.84 | 0.3935 | −0.3585 |
| 21.34 | 0.4009 | −0.4036 |
| 21.84 | 0.4864 | −0.4232 |
| 22.33 | 0.4864 | −0.4232 |
| 22.83 | 0.4167 | −0.3511 |
| 23.33 | 0.3423 | −0.3352 |

TABLE 4-continued (section 1 of 1): Signal Envelope over Time

| Time (min) | Positive Envelope Amplitude | Negative Envelope Amplitude |
|---|---|---|
| 23.82 | 0.4293 | −0.4452 |
| 24.32 | 0.4293 | −0.4452 |
| 24.81 | 0.2828 | −0.2849 |
| 25.31 | 0.3556 | −0.3471 |
| 25.81 | 0.3556 | −0.3471 |
| 26.30 | 0.3186 | −0.3065 |
| 26.80 | 0.3775 | −0.4193 |
| 27.30 | 0.3775 | −0.4193 |
| 27.79 | 0.4468 | −0.4887 |
| 28.29 | 0.4468 | −0.4887 |
| 28.78 | 0.4134 | −0.4401 |
| 29.28 | 0.4598 | −0.4492 |
| 29.78 | 0.6631 | −0.6218 |
| 30.27 | 0.6631 | −0.6484 |
| 30.77 | 0.6277 | −0.6484 |
| 31.27 | 0.7196 | −0.6131 |
| 31.76 | 0.7196 | −0.6256 |
| 32.26 | 0.5933 | −0.6256 |
| 32.76 | 0.5939 | −0.6139 |
| 33.25 | 0.6447 | −0.6139 |
| 33.75 | 0.6447 | −0.5781 |
| 34.24 | 0.5206 | −0.5522 |
| 34.74 | 0.5120 | −0.4524 |
| 35.24 | 0.5693 | −0.5593 |
| 35.73 | 0.5806 | −0.6281 |
| 36.23 | 0.6353 | −0.6281 |
| 36.73 | 0.6612 | −0.7711 |
| 37.22 | 0.7495 | −0.7711 |
| 37.72 | 0.9033 | −0.7881 |
| 38.21 | 0.9033 | −0.9579 |
| 38.71 | 1.0000 | −0.9579 |
| 39.21 | 1.0000 | −0.9530 |
| 39.70 | 0.7468 | −0.7817 |
| 40.20 | 0.8068 | −0.8533 |
| 40.70 | 0.8068 | −0.8533 |
| 41.19 | 0.8932 | −0.8975 |
| 41.69 | 0.8932 | −0.8975 |
| 42.18 | 0.7447 | −0.8096 |
| 42.68 | 0.8701 | −0.9335 |
| 43.18 | 1.0000 | −1.0000 |
| 43.67 | 1.0000 | −1.0000 |
| 44.17 | 0.8773 | −0.8567 |
| 44.67 | 0.8524 | −0.8567 |
| 45.16 | 0.8223 | −0.7123 |
| 45.66 | 0.6318 | −0.6186 |
| 46.15 | 0.6318 | −0.6186 |
| 46.65 | 0.4771 | −0.4372 |
| 47.15 | 0.6161 | −0.6313 |
| 47.64 | 0.6469 | −0.6586 |
| 48.14 | 0.6469 | −0.6586 |
| 48.64 | 0.5904 | −0.6161 |
| 49.13 | 0.5464 | −0.6161 |
| 49.63 | 0.4828 | −0.4497 |
| 50.13 | 0.5338 | −0.4836 |
| 50.62 | 0.5338 | −0.5249 |
| 51.12 | 0.5274 | −0.5249 |
| 51.61 | 0.5877 | −0.4857 |
| 52.11 | 0.5877 | −0.4857 |
| 52.61 | 0.4704 | −0.4497 |
| 53.10 | 0.5435 | −0.6408 |
| 53.60 | 0.5720 | −0.6408 |
| 54.10 | 0.5720 | −0.5439 |
| 54.59 | 0.5583 | −0.5406 |
| 55.09 | 0.7452 | −0.7463 |
| 55.58 | 0.7452 | −0.7463 |
| 56.08 | 0.6654 | −0.5772 |
| 56.58 | 0.7459 | −0.6972 |
| 57.07 | 0.7459 | −0.6972 |
| 57.57 | 0.6930 | −0.7514 |
| 58.07 | 0.8926 | −0.8716 |
| 58.56 | 0.8926 | −0.8716 |
| 59.06 | 0.7038 | −0.7405 |
| 59.55 | 0.4515 | −0.4581 |
| 60.05 | 0.3385 | −0.3652 |
| 60.55 | 0.3566 | −0.4052 |
| 61.04 | 0.4771 | −0.4472 |
| 61.54 | 0.4771 | −0.4472 |
| 62.04 | 0.4047 | −0.4437 |
| 62.53 | 0.4871 | −0.4492 |
| 63.03 | 0.5495 | −0.4905 |
| 63.52 | 0.5495 | −0.4905 |
| 64.02 | 0.4780 | −0.4269 |
| 64.52 | 0.3985 | −0.4156 |
| 65.01 | 0.3985 | −0.4243 |
| 65.51 | 0.4183 | −0.4243 |
| 66.01 | 0.4183 | −0.4097 |
| 66.50 | 0.4125 | −0.4097 |
| 67.00 | 0.3659 | −0.3626 |
| 67.50 | 0.3156 | −0.3128 |

TABLE 5

Time-Frequency Analysis input Parameters and Settings

Wave File Parameters:

| | | | | |
|---|---|---|---|---|
| Data Length = | 179905656 | (samples) = | 4079.49 | (sec) |
| Sample Rate = | 44100 | (Hz) | | |
| Number of Bits = | 16 | (bits) | | |
| Number of Channels = | 2 | (channels summed into mono signal) | | |

Time Segmentation of Data:

| | | | | |
|---|---|---|---|---|
| Data Segment Length = | 2626359 | (samples) = | 59.55 | (sec) |
| Data Segment Offset = | 1313179 | (samples) = | 29.78 | (sec) |
| Number of Data Segments = | 136 | (segments) | | |

Frequency Segmentation of Data:

| | | |
|---|---|---|
| Nyquist Frequency Limit = | 22050 | (Hz) |
| Frequency Bin Length = | logarithmic (power density averaged over bin) | |
| Frequency Bin Spacing = | logarithmic (equally spaced on log scale) | |
| Number of Frequency Bins = | 24 | (bins/decade) |

TABLE 5-continued

Time-Frequency Analysis input Parameters and Settings

Welch Periodogram Parameters:

| | | | | |
|---|---|---|---|---|
| Data Window Type = | | Hamming | | |
| Resolution Bandwidth = | 1 | (Hz) | | |
| Windowed Segment Length = | 176401 | (samples) = | 4.00 | (sec) |
| Windowed Segment Offset = | 88200 | (samples) = | 2.00 | (sec) |
| Number of Windowed Segments = | 28 | (segments) | | |

What is claimed is:

1. An apparatus capable of transmitting vibrations to a user comprising:
 a support structure configured to support at least a part of the user's body, said support structure including a frame comprising a plurality of frame apertures passing through the frame;
 a transducer located in a seat of the support structure and attached to a board, the board comprising a plurality of board apertures passing through the board and aligned with the plurality of frame apertures, wherein the board is coupled to the frame of the support structure by a plurality of fasteners, and wherein each fastener of the plurality of fasteners passes through a frame aperture and a board aperture such that the transducer and the board are capable of movement in relation to the frame, and vibration generated from the transducer is distributed throughout the frame; and
 an audio signal source, wherein all audio signals from the audio signal source pass through the transducer without filtering out any frequencies when the apparatus is in use, and wherein the audio signals from the audio signal source comprise frequencies greater than approximately 1,000 Hz.

2. The apparatus of claim 1, wherein the audio signals from the audio signal source comprise frequencies in a range from about 20 Hz to about 20,000 Hz.

3. The apparatus of claim 1, wherein the transducer comprises a mass-loaded cone.

4. The apparatus of claim 3, wherein the transducer and the board are capable of moving up to about 0.2 inch in relation to the frame, in a direction parallel to the movement of the mass-loaded cone.

5. The apparatus of claim 3, wherein the transducer and the board are capable of moving up to about 0.1 inch in relation the frame, in a direction parallel to the movement of the mass-loaded cone.

6. The apparatus of claim 1, wherein the transducer comprises a speaker basket containing a permanent magnet, and the transducer is attached to the board via a plurality of fasteners passing through apertures in the speaker basket.

7. The apparatus of claim 1, wherein a foam gasket is positioned between the board and the frame of the support structure, and the foam gasket is in direct contact with the board and the frame.

8. The apparatus of claim 1, wherein the transducer is capable of creating an electromagnetic field sufficient to be perceptible to the user when the apparatus is in use.

9. The apparatus of claim 1, wherein the board is located in a depression in the frame.

10. The apparatus of claim 1, further comprising a speaker located in a back of the support structure.

11. A method of reducing a side effect of chemotherapy experienced by the user, comprising:
 providing the apparatus of claim 10; and
 using the apparatus to administer electromagnetically produced vibration and sound to the user, by transmitting the audio signals to the transducer and the speaker while the user is supported by the support structure.

12. A method of improving the health of the user, comprising:
 providing the apparatus of claim 10; and
 using the apparatus to administer electromagnetically produced vibration and sound to the user, by transmitting the audio signals to the transducer and the speaker while the user is supported by the support structure.

13. The method of claim 12, wherein the electromagnetically produced vibration and sound is administered to the user in sessions conducted up to seven days per week.

* * * * *